United States Patent
Cho et al.

(10) Patent No.: US 11,737,353 B2
(45) Date of Patent: Aug. 22, 2023

(54) PLURALITY OF HOST MATERIALS AND ORGANIC ELECTROLUMINESCENT DEVICE COMPRISING THE SAME

(71) Applicant: Rohm and Haas Electronic Materials Korea LTD., Chungcheongnam-do (KR)

(72) Inventors: Sang-Hee Cho, Gyeonggi-do (KR); Doo-Hyeon Moon, Gyeonggi-do (KR); Bitnari Kim, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 0 days.

(21) Appl. No.: 17/670,572

(22) Filed: Feb. 14, 2022

(65) Prior Publication Data
US 2022/0165956 A1    May 26, 2022

Related U.S. Application Data

(63) Continuation of application No. 16/481,644, filed as application No. PCT/KR2018/002230 on Feb. 23, 2018, now abandoned.

(30) Foreign Application Priority Data

Feb. 27, 2017 (KR) .................. 10-2017-0025749
Feb. 21, 2018 (KR) .................. 10-2018-0020359

(51) Int. Cl.
| | | |
|---|---|---|
| H10K 85/60 | (2023.01) | |
| C09K 11/06 | (2006.01) | |
| H10K 50/11 | (2023.01) | |
| H10K 50/12 | (2023.01) | |
| H10K 101/10 | (2023.01) | |
| H10K 101/00 | (2023.01) | |

(52) U.S. Cl.
CPC ............ *H10K 85/631* (2023.02); *C09K 11/06* (2013.01); *H10K 85/624* (2023.02); *H10K 85/654* (2023.02); *H10K 85/656* (2023.02); *H10K 50/11* (2023.02); *H10K 50/12* (2023.02); *H10K 2101/10* (2023.02); *H10K 2101/90* (2023.02)

(58) Field of Classification Search
CPC .. C07D 263/57; C07D 277/66; C07D 403/04; C07D 403/10; C07D 413/04; C07D 413/10; C07D 413/14; C07D 417/04; C07D 417/14; H01L 2251/5384; H01L 51/0056; H01L 51/0059; H01L 51/006; H01L 51/0062; H01L 51/0067; H01L 51/0069; H01L 51/5016; H01L 51/5024; H10K 85/631; H10K 85/624; H10K 85/654; H10K 85/656; H10K 50/11; H10K 50/12; H10K 2101/10; H10K 2101/90; H10K 85/633; H10K 85/649; C09K 11/06
See application file for complete search history.

(56) References Cited

U.S. PATENT DOCUMENTS

| | | | | |
|---|---|---|---|---|
| 2004/0076853 A1* | 4/2004 | Jarikov | ............... | H01L 51/5012 428/917 |
| 2014/0042370 A1* | 2/2014 | Martynova | ......... | H01L 51/0071 546/37 |
| 2018/0208837 A1* | 7/2018 | Ahn | .................... | H01L 51/0074 |

FOREIGN PATENT DOCUMENTS

WO    WO-2017030283 A1 *  2/2017 ........... C07D 251/12

* cited by examiner

*Primary Examiner* — Dawn L Garrett
(74) *Attorney, Agent, or Firm* — G. Creston Campbell

(57) ABSTRACT

The present disclosure relates to a plurality of host materials and an organic electroluminescent device comprising the same. The organic electroluminescent device of the present disclosure can exhibit excellent lifespan characteristics while maintaining high luminous efficiency by including a specific combination of a plurality of host compounds.

7 Claims, 1 Drawing Sheet

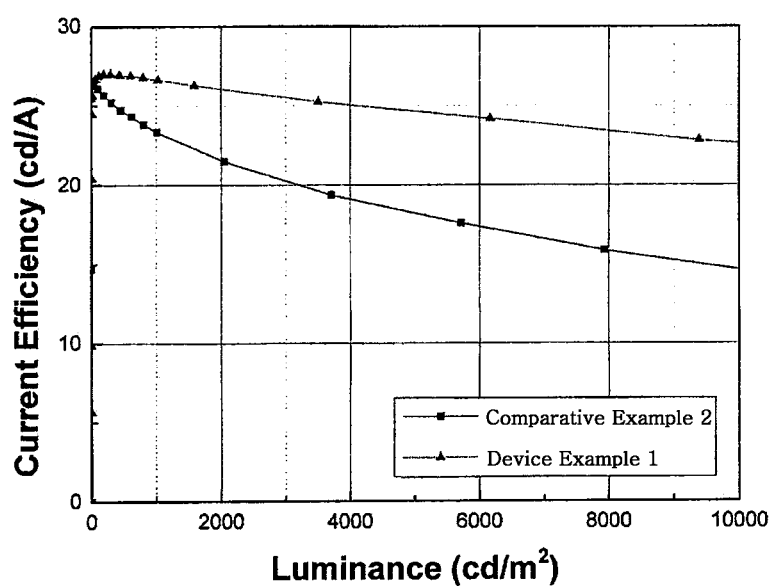

PLURALITY OF HOST MATERIALS AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 16/481,644, filed Jul. 29, 2019, which is the National Stage Entry of PCT/KR2018/002230, filed Feb. 23, 2018, both of which are incorporated by reference herein in their entirety.

TECHNICAL FIELD

The present disclosure relates to a plurality of host materials and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer (see Appl. Phys. Lett. 51, 913, 1987).

An organic EL device (OLED) changes electric energy into light by applying electricity to an organic electroluminescent material, and commonly comprises an anode, a cathode, and an organic layer formed between the two electrodes. The organic layer of the organic EL device may comprise a hole injection layer, a hole transport layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, an electron blocking material, a light-emitting material, an electron buffer material, a hole blocking material, an electron transport material, an electron injection material, etc., depending on their functions. In the organic EL device, holes from the anode and electrons from the cathode are injected into a light-emitting layer by the application of electric voltage, and excitons having high energy are produced by the recombination of the holes and electrons. The organic light-emitting compound moves into an excited state by the energy and emits light from an energy when the organic light-emitting compound returns to the ground state from the excited state.

The most important factor determining luminous efficiency in an organic EL device is light-emitting materials. The light-emitting materials are required to have the following features: high quantum efficiency, high movement degree of an electron and a hole, and uniformality and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an organic EL device having high efficiency and long lifespan. In particular, the development of highly excellent light-emitting material over conventional materials is urgently required, considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature to achieve thermal stability, high electrochemical stability to achieve a long lifespan, easy formability of an amorphous thin film, good adhesion with adjacent layers, and no movement between layers.

A light-emitting material can be used as a combination of a host and a dopant to improve color purity, luminous efficiency, and stability. Generally, an EL device having excellent characteristics has a structure comprising a light-emitting layer formed by doping a dopant to a host. When using such a dopant/host material system as a light-emitting material, their selection is important since host materials greatly influence the efficiency and lifespan of the EL device.

Japanese Patent Application Laid-Open No. 2001-23777 discloses an organic electroluminescent device using as a compound in which a 5-membered heteroaryl containing nitrogen is condensed in an intermediate benzene ring of a phenanthrene backbone, as a host material. The organic electroluminescent device comprising the compound disclosed in said reference exhibits excellent color purity characteristics of blue; however, said reference does not disclose the mixed structure of the phosphorescent light-emitting layer and still needs improvement in driving voltage, current efficiency, and driving lifespan.

DISCLOSURE

Problems to be Solved

The object of the present disclosure is to provide an organic electroluminescent device having a long lifespan while maintaining a high luminous efficiency.

Solution to Problems

As a result of intensive studies to solve the technical problem above, the present inventors found that the aforementioned objective can be achieved by a plurality of host materials comprising at least one first host compound represented by the following formula 1 or 2 and at least one second host compound represented by the following formula 3, and completed the present invention.

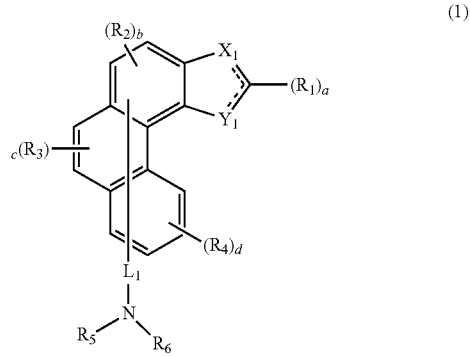

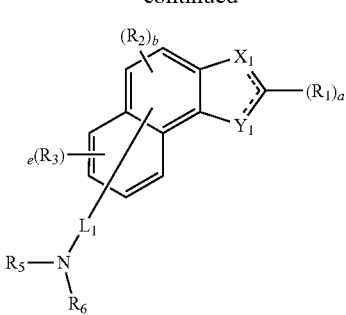

(2)

wherein,

X₁ represents —N═, —NR₇—, —O— or —S—,

Y₁ represents —N═, —NR₈—, —O— or —S—, provided that when X₁ represents —N═, Y₁ represents —NR₈—, —O— or —S—, and when X₁ represents —NR₇—, Y₁ represents —N═, —O— or —S—, R₁ represents a substituted or unsubstituted (C6-C30)aryl, or a substituted or unsubstituted (3- to 30-membered)heteroaryl, R₂ to R₈ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C6-C30)arylamino, or a substituted or unsubstituted (C1-C30)alkyl(C6-C30)arylamino, or may be linked to an adjacent substituent to form a substituted or unsubstituted, (C3-C30) mono- or polycyclic, alicyclic, or aromatic ring, whose carbon atom may be replaced with at least one heteroatom selected from nitrogen, oxygen, and sulfur, L₁ represents a single bond, a substituted or unsubstituted (C6-C30)arylene, or a substituted or unsubstituted (3- to 30-membered)heteroarylene, a represents 1, b and c each independently represent 1 or 2, d and e each independently represent an integer of 1 to 4, and the heteroaryl(ene) contains at least one heteroatom selected from B, N, O, S, Si, and P;

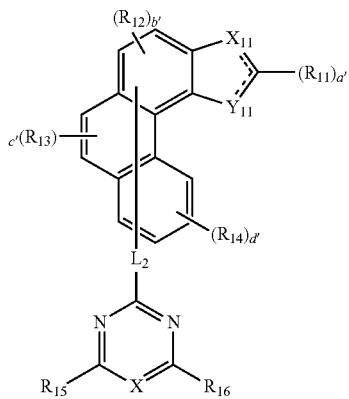

(3)

wherein,

X₁₁ represents —N═, —NR₁₇—, —O— or —S—,

Y₁₁ represents —N═, —NR₁₈—, —O— or —S—, provided that when X₁₁ represents —N═, Y₁₁ represents —NR₁₈—, —O— or —S—, and when X₁₁ represents —NR₁₇—, Y₁₁ represents —N═, —O— or —S—, X represents N or CH, R₁₁ represents a substituted or unsubstituted (C6-C30)aryl, or a substituted or unsubstituted (3- to 30-membered)heteroaryl, R₁₂ to R₁₈ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C6-C30)arylamino, or a substituted or unsubstituted (C1-C30)alkyl(C6-C30)arylamino, or may be linked to an adjacent substituent to form a substituted or unsubstituted, (C3-C30) mono- or polycyclic, alicyclic, or aromatic ring, whose carbon atom may be replaced with at least one heteroatom selected from nitrogen, oxygen, and sulfur, L₂ represents a single bond, a substituted or unsubstituted (C6-C30)arylene, or a substituted or unsubstituted (3- to 30-membered)heteroarylene, a' represents 1, b' and c' each independently represents 1 or 2, d' represents an integer of 1 to 4, and the heteroaryl(ene) contains at least one heteroatom selected from B, N, O, S, Si, and P.

Effects of the Invention

The phenanthro oxazole-based and phenanthro thiazole-based compounds according to the present disclosure have inherently high electronegativity and electron-rich groups, as well as have a rigid property as a structure in which phenanthrene and oxazole, or phenanthrene and thiazole, etc., are fused, so that the above compounds of the present disclosure facilitate intermolecular charge transition. In addition, if such an intermolecular stacking is strengthened, implementation of horizontal molecular orientation is easier, thereby enabling fast electronic current characteristics to be implemented. Accordingly, it is possible to provide an organic electroluminescent device which exhibits a relatively low driving voltage by improving the interfacial characteristics and excellent luminous efficiency such as current efficiency and power efficiency, and a high purity color, while maintaining the intermolecular stacking effect with the electron transport layer by using limited structure such as triazine and pyrimidine derivatives, etc., as a light-emitting material.

In addition, when a light-emitting material is used as mixing the hole-type amine substituted with the phenanthro oxazole-based compounds and the phenanthro thiazole-based compounds as the first host and the electron-type azine material substituted with the phenanthro oxazole-based compounds and the phenanthro thiazole-based compounds as the second host, it is possible to implement an organic electroluminescent device having a high efficiency, long lifespan, and fast driving voltage. Generally, when the phosphorescent light-emitting material is substituted with other substituents such as a carbazole type derivative having a high dihedral angle, the driving voltage increases and the efficiency decreases due to the interruption of the electron current. However, when using the light-emitting compounds according to the present disclosure, it is possible to provide an organic electroluminescent device having a relatively low driving voltage and excellent luminous efficiency such as current efficiency and power efficiency, and a high purity color through fast current injection characteristics and improving the interfacial characteristics by improving the intermolecular stacking and interaction.

BRIEF DESCRIPTION OF THE FIGURES

FIGURE illustrates the current efficiency according to the luminance of the organic electroluminescent device produced in Comparative Example 2 and Device Example 1.

EMBODIMENTS OF THE INVENTION

Hereinafter, the present disclosure will be described in detail. However, the following desception is intended to explain the disclosure, and is not meant in any way to restrict the scope of the disclosure.

The organic electroluminescent device comprising the organic electroluminescent compound represented by formula 1, 2, or 3 above will be described in more detail as follows.

In formulae 1 and 2 above, $X_1$ represents —N=, —$NR_7$—, —O— or —S—, $Y_1$ represents —N=, —$NR_8$—, —O— or —S—, provided that when $X_1$ represents —N=, $Y_1$ represents —$NR_8$—, —O— or —S—, and when $X_1$ represents —$NR_7$—, $Y_1$ represents —N=, —O— or —S—. According to one embodiment of the present disclosure, one of $X_1$ and $Y_1$ may be —N=, and the other may be —$NR_7$—, —O— or —S—. In addition, according to another embodiment of the present disclosure, one of $X_1$ and $Y_1$ may be —N=, and the other may be —O— or —S—. Herein, both of $X_1$ and $Y_1$ may not be —O— or —S—, and when either one of $X_1$ and $Y_1$ may be —O—, the other may not be —S—. For example, $X_1$ may be —N=, and $Y_1$ may be —O—, $X_1$ may be —O—, and $Y_1$ may be —N=, or $X_1$ may be —S—, and $Y_1$ may be —N=.

In formulae 1 and 2 above, $R_1$ represents a substituted or unsubstituted (C6-C30)aryl, or a substituted or unsubstituted (3- to 30-membered)heteroaryl, preferably, a substituted or unsubstituted (C6-C30)aryl, or a substituted or unsubstituted (5- to 25-membered)heteroaryl, more preferably, a substituted or unsubstituted (C6-C30)aryl, or a substituted or unsubstituted (5- to 20-membered)heteroaryl, e.g., may be unsubstituted phenyl, unsubstituted biphenyl, unsubstituted naphthyl, fluorenyl substituted with methyl, benzofluorenyl substituted with methyl, unsubstituted dibenzofuranyl, unsubstituted dibenzothiophenyl, spiro[fluorene-fluorene]yl, or spiro[fluorene-benzofluorene]yl.

In formulae 1 and 2 above, $R_2$ to $R_6$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di-(C6-C30)arylamino, or a substituted or unsubstituted (C1-C30)alkyl(C6-C30)arylamino, or may be linked to an adjacent substituent to form a substituted or unsubstituted, (C3-C30) mono- or polycyclic, alicyclic, or aromatic ring, whose carbon atom may be replaced with at least one heteroatom selected from nitrogen, oxygen, and sulfur, preferably, each independently represent hydrogen, a substituted or unsubstituted (C6-C25)aryl, a substituted or unsubstituted (3- to 25-membered)heteroaryl, a substituted or unsubstituted mono- or di- (C6-C25)arylamino, or may be linked to an adjacent substituent to form a substituted or unsubstituted, (C3-C25) mono- or polycyclic, alicyclic, or aromatic ring, whose carbon atom may be replaced with at least one heteroatom selected from nitrogen, oxygen, and sulfur, more preferably, each independently represent hydrogen, a substituted or unsubstituted (C6-C20)aryl, a substituted or unsubstituted (5- to 25-membered)heteroaryl, a substituted or unsubstituted di(C6-C18)arylamino, or may be linked to an adjacent substituent to form a substituted or unsubstituted, (C3-C25) mono- or polycyclic, alicyclic, or aromatic ring, whose carbon atom may be replaced with at least one heteroatom selected from nitrogen and oxygen, and the heteroaryl may contain at least one heteroatom selected from B, N, O, S, Si, and P. For example, $R_5$ and $R_6$ each independently may be a substituted or unsubstituted phenyl, a substituted or unsubstituted m-biphenyl, a substituted or unsubstituted p-biphenyl, a substituted or unsubstituted fluorenyl, a substituted or unsubstituted naphthyl, a substituted or unsubstituted phenanthrenyl, or a substituted or unsubstituted benzofluorenyl.

In formulae 1 and 2 above, a represents 1 or 2, preferably, 1; b and c each independently represent 1 or 2, preferably, 1; d and e each independently represent an integer of 1 to 4, preferably, 1 or 2.

In formulae 1 and 2 above, $L_1$ represents a single bond, a substituted or unsubstituted (C6-C30)arylene, or a substituted or unsubstituted (3- to 30-membered)heteroarylene, preferably, a single bond, or a substituted or unsubstituted (C6-C18)arylene, more preferably, a single bond, or an unsubstituted (C6-C12)arylene, e.g., may be a single bond, or an unsubstituted phenylene.

The compound represented by the formula 1 or 2 is represented by any one of the following formulae 1-1 to 1-5:

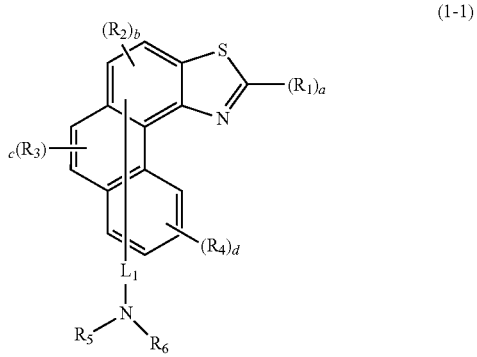

(1-1)

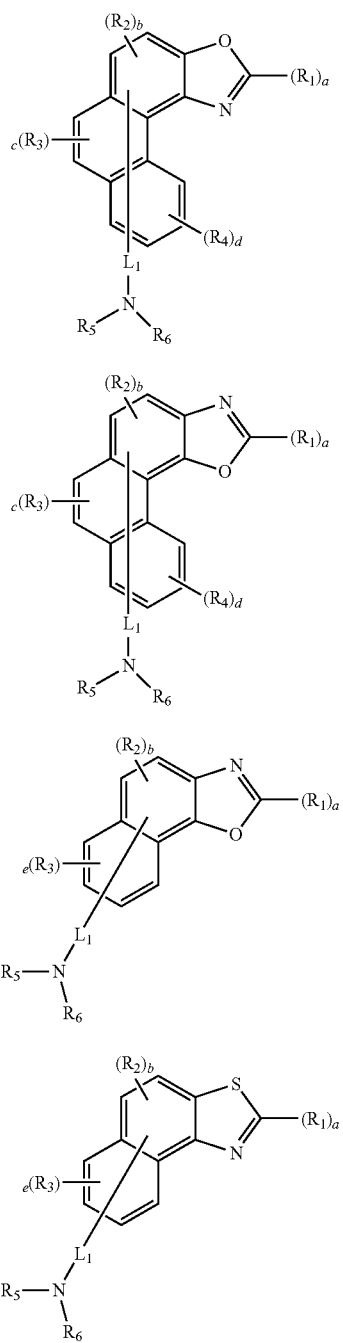

In formulae 1-1 to 1-5 above, $R_1$ to $R_6$, $L_1$ and a to e are as defined in the formulae 1 and 2.

In formula 3 above, $X_{11}$ represents —N═, —$NR_{17}$—, —O— or —S—, $Y_{11}$ represents —N═, —$NR_{18}$—, —O— or —S—, provided that when $X_{11}$ represents —N═, $Y_{11}$ represents —$NR_{18}$—, —O— or —S—, and when $X_{11}$ represents —$NR_{17}$—, $Y_{11}$ represents —N═, —O— or —S—. According to one embodiment of the present disclosure, one of $X_{11}$ and $Y_{11}$ may be —N═, and the other may be —$NR_{17}$—, —O— or —S—. In addition, according to another embodiment of the present disclosure, one of $X_{11}$ and $Y_{11}$ may be —N═, and the other may be —O— or —S—. Herein, both $X_{11}$ and $Y_{11}$ may not be —O— or —S—, and when either one of $X_1$ and $Y_1$ may be —O—, the other may not be —S—.

In formula 3 above, $R_{11}$ represents a substituted or unsubstituted (C6-C30)aryl, or a substituted or unsubstituted (3- to 30-membered)heteroaryl, preferably, a substituted or unsubstituted (C6-C30)aryl, or a substituted or unsubstituted (5- to 25-membered)heteroaryl, more preferably, a substituted or unsubstituted (C6-C30)aryl, or a substituted or unsubstituted (5- to 20-membered)heteroaryl, e.g., may be unsubstituted phenyl, unsubstituted biphenyl, unsubstituted naphthyl, fluorenyl substituted with methyl, a substituted or unsubstituted carbazolyl, benzofluorenyl substituted with methyl, unsubstituted dibenzofuranyl, unsubstituted dibenzothiophenyl, unsubstituted benzonaphthofuranyl, spiro[fluorene-fluorene]yl, or spiro[fluorene-benzofluorene]yl.

In formula 3 above, $R_{12}$ to $R_{18}$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C6-C30)arylamino, or a substituted or unsubstituted (C1-C30) alkyl(C6-C30)arylamino, or may be linked to an adjacent substituent to form a substituted or unsubstituted, (C3-C30) mono- or polycyclic, alicyclic, or aromatic ring, whose carbon atom may be replaced with at least one heteroatom selected from nitrogen, oxygen, and sulfur, preferably, each independently hydrogen, a substituted or unsubstituted (C6-C25)aryl, a substituted or unsubstituted (3- to 25-membered) heteroaryl, a substituted or unsubstituted mono- or di- (C6-C25)arylamino, or may be linked to an adjacent substituent to form a substituted or unsubstituted, (C3-C25) mono- or polycyclic, alicyclic, or aromatic ring, whose carbon atom may be replaced with at least one heteroatom selected from nitrogen, oxygen, and sulfur, more preferably, each independently hydrogen, a substituted or unsubstituted (C6-C20) aryl, a substituted or unsubstituted (5- to 25-membered) heteroaryl, a substituted or unsubstituted di(C6-C18) arylamino, or may be linked to an adjacent substituent to form a substituted or unsubstituted, (C3-C25) mono- or polycyclic, alicyclic, or aromatic ring, whose carbon atom may be replaced with at least one heteroatom selected from nitrogen and sulfur, and the heteroaryl contains at least one heteroatom selected from B, N, O, S, Si, and P. For example, $R_{15}$ and $R_{16}$ each independently may be selected from the group consisting of a substituted or unsubstituted phenyl, a substituted or unsubstituted o-biphenyl, a substituted or unsubstituted m-biphenyl, a substituted or unsubstituted p-biphenyl, a substituted or unsubstituted naphthyl, a substituted or unsubstituted fluorenyl, a substituted or unsubstituted carbazolyl, a substituted or unsubstituted dibenzothiophenyl, a substituted or unsubstituted benzofluorenyl, a substituted or unsubstituted benzocarbazole, and a substituted or unsubstituted benzonaphthothiophene.

In formula 3 above, a' represents 1 or 2, preferably 1; b' and c' each independently represent 1 or 2, preferably 1; d' represents an integer of 1 to 4, preferably, 1 or 2.

In formula 3 above, X represents N or CH.

In formula 3 above, $L_2$ represents a single bond, a substituted or unsubstituted (C6-C30)arylene, or a substituted or unsubstituted (3- to 30-membered)heteroarylene, preferably, a single bond, a substituted or unsubstituted (C6-C18) arylene, more preferably, a single bond, an unsubstituted (C6-C12)arylene, e.g., may be a single bond or unsubstituted phenylene.

The compound represented by the formula 3 is represented by any one of the following formulae 3-1 to 3-6:

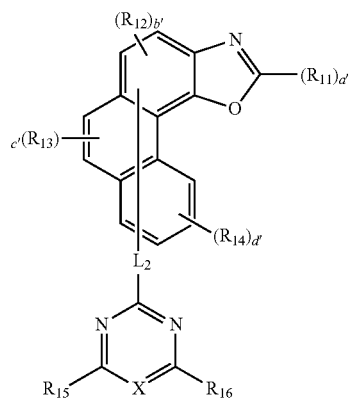
(3-1)

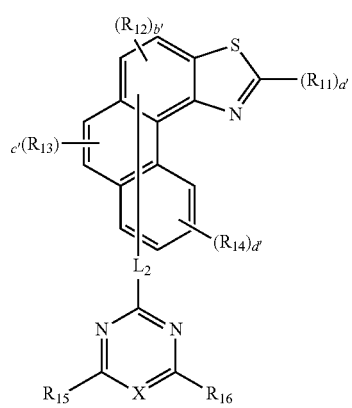
(3-2)

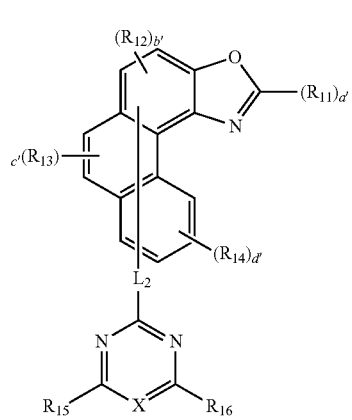
(3-3)

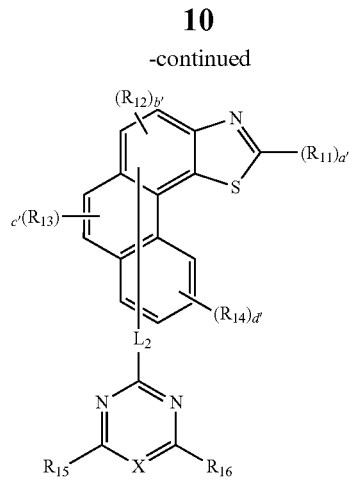
(3-4)

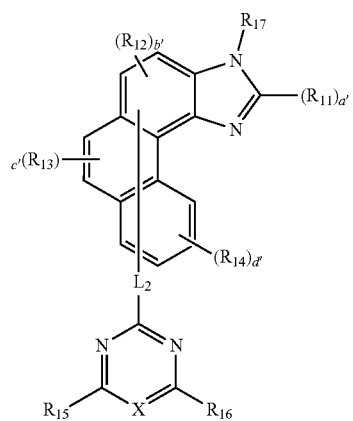
(3-5)

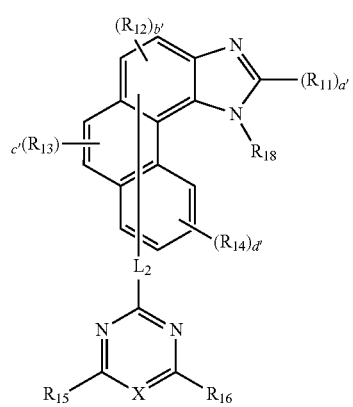
(3-6)

In formulae 3-1 to 3-6 above, $R_{11}$ to $R_{18}$, $L_2$, X and a' to d' are as defined in the formula 3.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, and tert-butyl, etc. "(C2-C30)alkenyl" is meant to be a linear or branched alkenyl having 2 to 30 carbon atoms constituting the chain, in which the number of carbon atoms is preferably 2 to 20, and more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is meant to be a linear or branched alkynyl having 2 to 30 carbon atoms constituting the chain, in which the number of carbon atoms is preferably 2 to 20, and more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7, and includes cyclopropyl, cyclobutyl, cyclopentyl, cyclohexyl, etc. "(3- to 7-membered)heterocycloalkyl" is meant to be a cycloalkyl having 3 to 7, preferably 5 to 7, ring backbone atoms, including at least one heteroatom selected from the group consisting of B, N, O, S, Si, and P, and preferably O, S, and N, and includes tetrahydrofuran, pyrrolidine, thiolan, tetrahydropyran, etc. "(C6-C60)aryl(ene)" is meant to be a monocyclic or fused ring radical derived from an aromatic hydrocarbon having 6 to 60 ring backbone carbon atoms, in which the number of the ring backbone carbon atoms is preferably 6 to 30, more preferably 6 to 20, may be partially saturated, and may comprise a spiro structure. The aryl includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc. "(3- to 30-membered)heteroaryl(ene)" is meant to be an aryl having 3 to 30 ring backbone atoms, including at least one, preferably 1 to 4 heteroatoms selected from the group consisting of B, N, O, S, Si, and P. The heteroaryl may be a monocyclic ring, or a fused ring condensed with at least one benzene ring; may be partially saturated; may be one formed by linking at least one heteroaryl or aryl group to a heteroaryl group via a single bond. The heteroaryl includes a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, naphthyridyl, carbazolyl, phenoxazinyl, phenanthridinyl, benzodioxolyl, etc. "(5- to 30-membered)heteroaryl containing nitrogen" is meant to be an aryl group having at least one N, and 5 to 30 ring backbone atoms, in which the number of ring backbone atoms is preferably 5 to 20, more preferably 5 to 15; having preferably 1 to 4 heteroatoms, and may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including pyrrolyl, imidazolyl, pyrazolyl, triazinyl, tetrazinyl, triazolyl, tetrazolyl, pyridyl, pyrazinyl, pyrimidinyl, pyridazinyl, etc., and a fused ring-type heteroaryl including benzimidazolyl, isoindolyl, indolyl, indazolyl, benzothiadiazolyl, quinolyl, isoquinolyl, cinnolinyl, quinazolinyl, quinoxalinyl, carbazolyl, phenanthridinyl, etc. "Halogen" includes F, Cl, Br, and I.

In addition, "substituted" in the expression "substituted or unsubstituted" means that a hydrogen atom is replaced with another atom or functional group (i.e., a substituent) in a certain functional group. The substituents of the substituted alkyl, the substituted alkoxy, the substituted cycloalkyl, the substituted aryl(ene), the substituted heteroaryl(ene), the substituted trialkylsilyl, the substituted triarylsilyl, the substituted dialkylarylsilyl, the substituted alkyldiarylsilyl, the substituted mono- or di- alkylamino, the substituted mono- or di- arylamino, the substituted alkylarylamino, and the substituted mono- or polycyclic, alicyclic or aromatic ring, in $R_1$ to $R_8$, $R_{11}$ to $R_{18}$, $L_1$, and $L_2$ of formulae 1 to 3, are each independently at least one selected from the group consisting of deuterium; halogen; cyano; carboxyl; nitro; hydroxy; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (3- to 7-membered)heterocycloalkyl; (C6-C30)aryloxy; (C6-C30)arylthio; (C6-C30)aryl- or di(C6-C30)arylamino-substituted or unsubstituted (3- to 30-membered)heteroaryl; cyano-, (3- to 30-membered)heteroaryl-, or tri(C6-C30)arylsilyl-substituted or unsubstituted (C6-C30)aryl; tri(C1-C30)alkylsilyl; tri(C6-C30)arylsilyl; di(C1-C30)alkyl(C6-C30)arylsilyl; (C1-C30)alkyldi(C6-C30)arylsilyl; amino; a mono- or di- (C1-C30)alkylamino; a mono- or di- (C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl, preferably, are each independently at least one selected from the group consisting of (C1-C20)alkyl; (C6-C18)aryl-substituted or unsubstituted (3- to 25-membered)heteroaryl; cyano-, tri(C6-C18)arylsilyl-, or (3- to 20-membered)heteroaryl-, substituted or unsubstituted (C6-C20)aryl; tri(C6-C18)arylsilyl; and (C1-C20)alkyl(C6-C20)aryl.

The compound represented by formula 1 or 2 may be more specifically illustrated by the following compounds, but is not limited thereto:

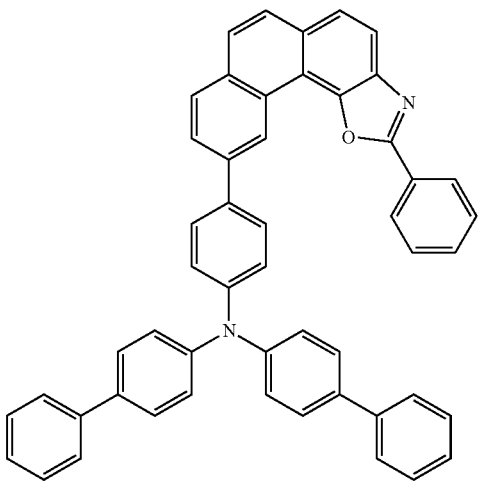

H1-1

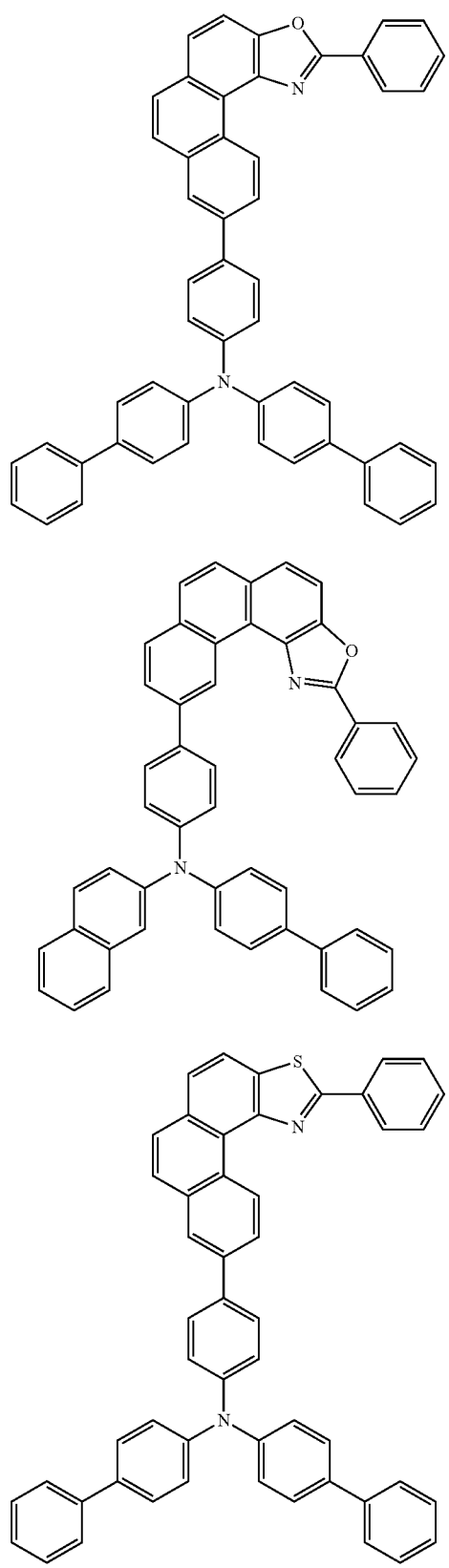
H1-2
H1-3
H1-4
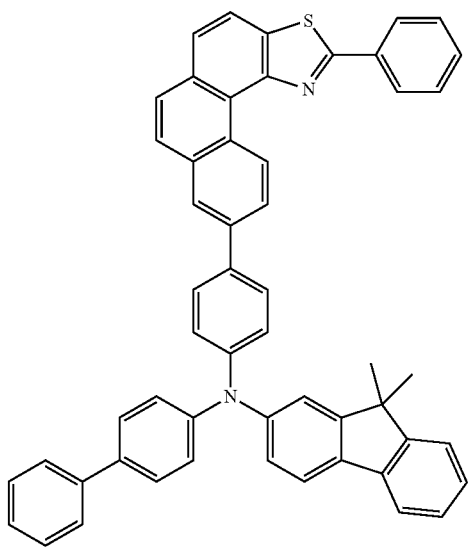
H1-5
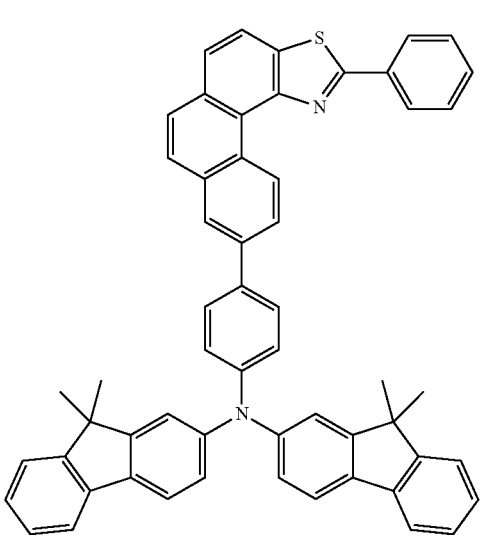
H1-6
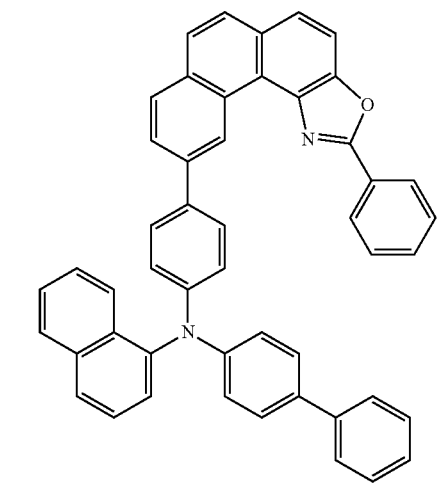
H1-7

H1-8
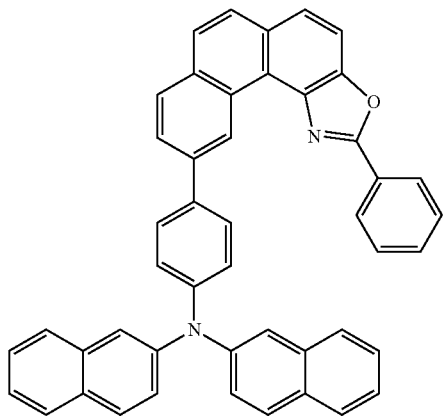
H1-9
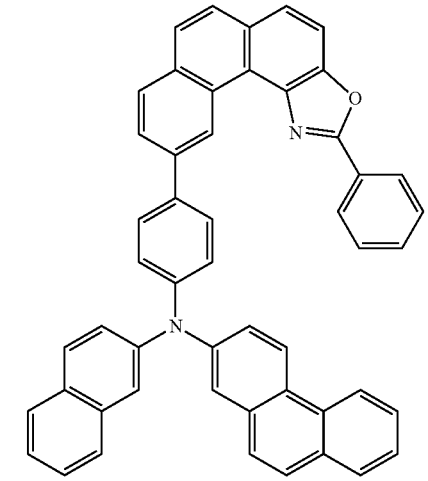
H1-10
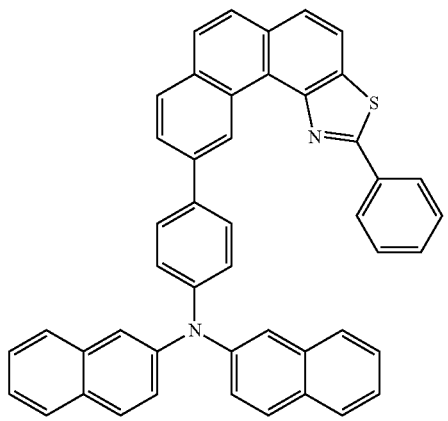
H1-11
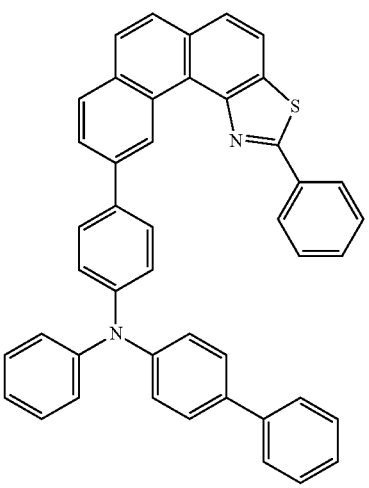
H1-12
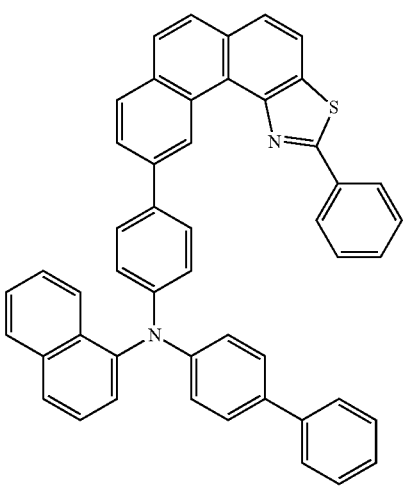
H1-13
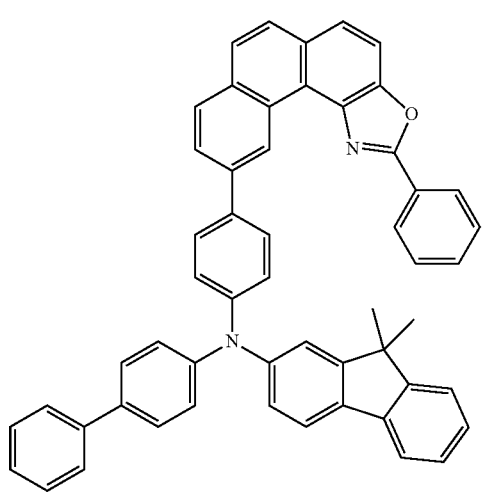

H1-14
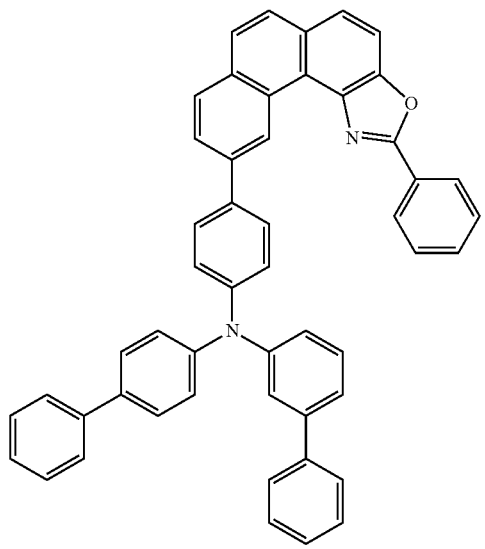
H1-15
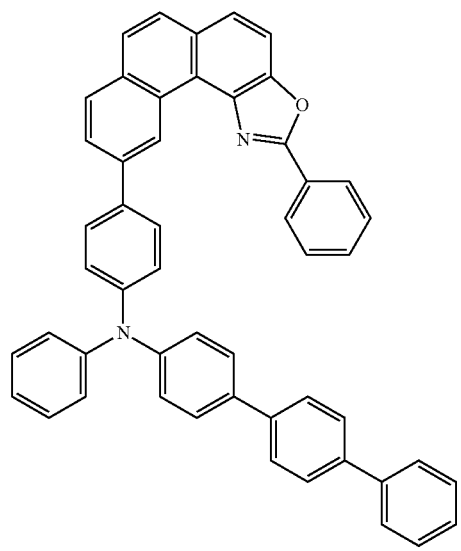
H1-16
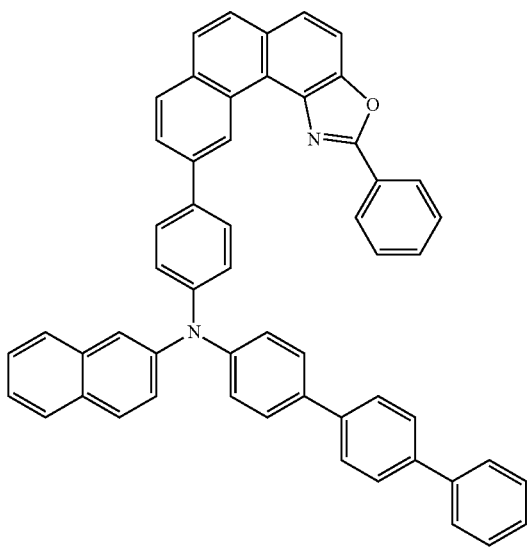
H1-17
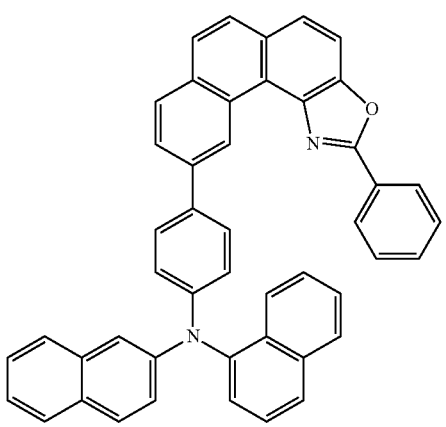
H1-18
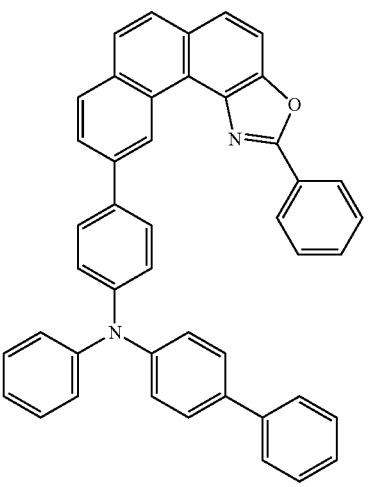
H1-19
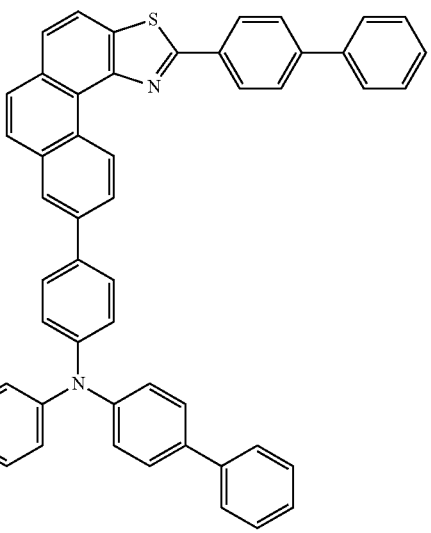

H1-20
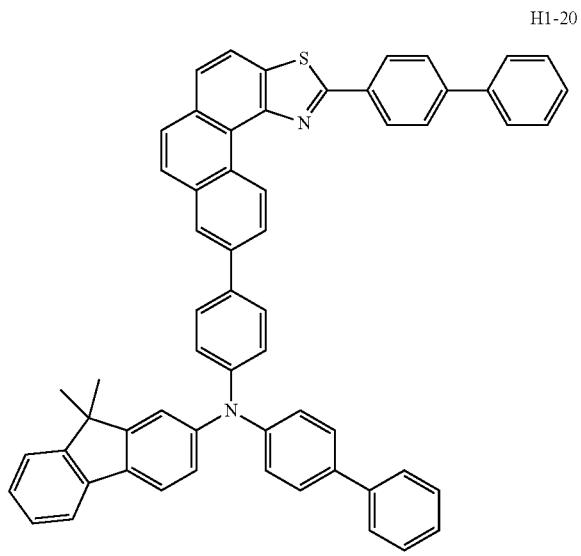
H1-21
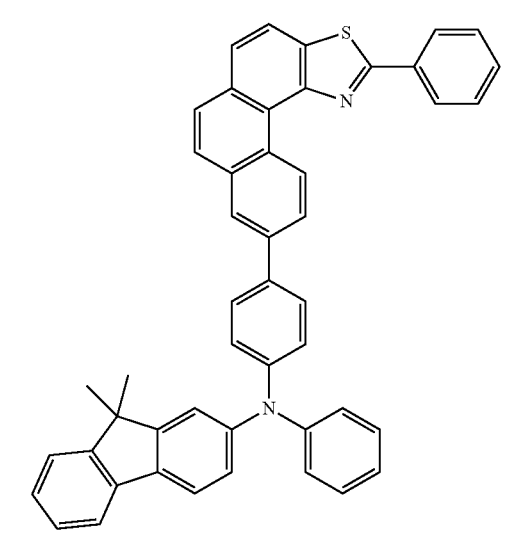
H1-22
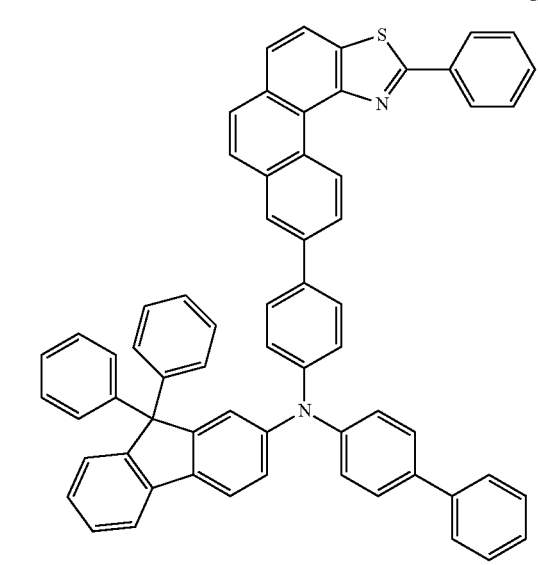
H1-23
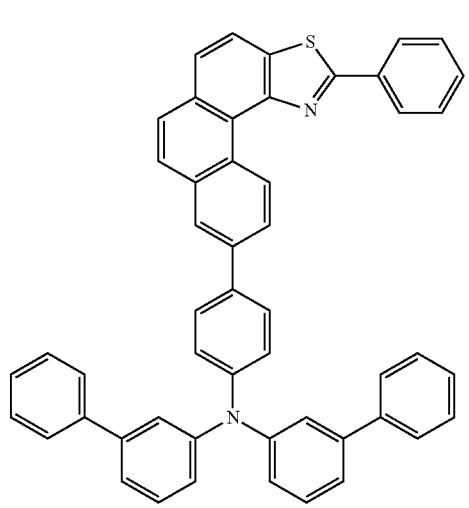
H1-24
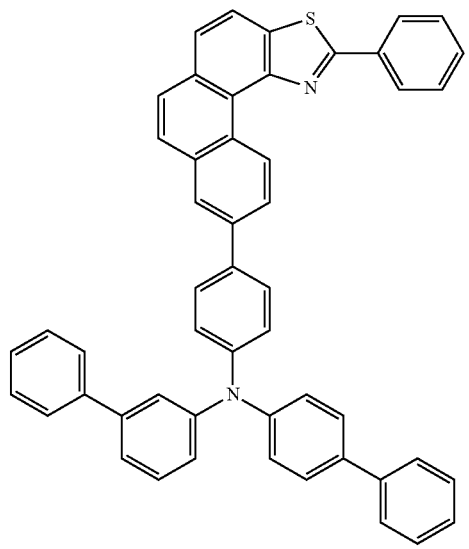
H1-25
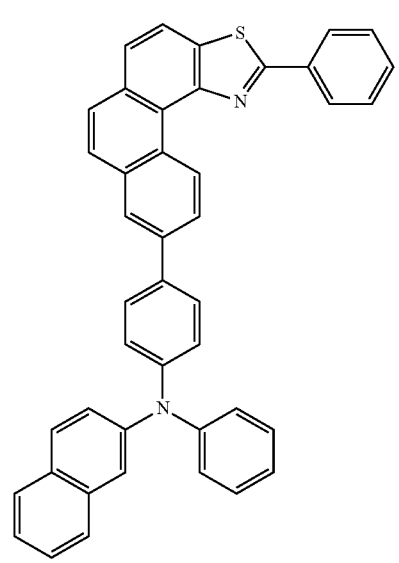

-continued
H1-26
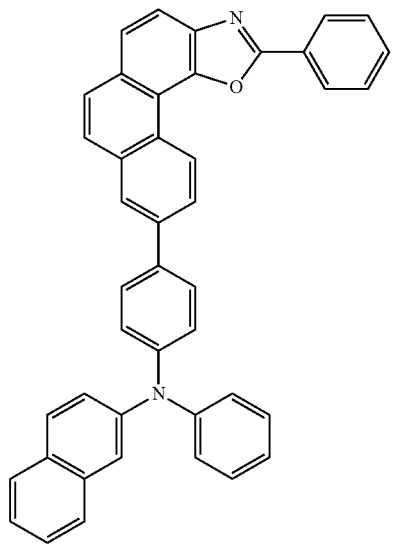
H1-27
H1-28
H1-29
-continued
H1-30
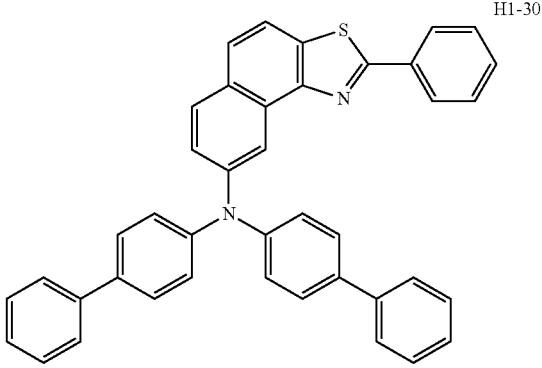
H1-31
H1-32
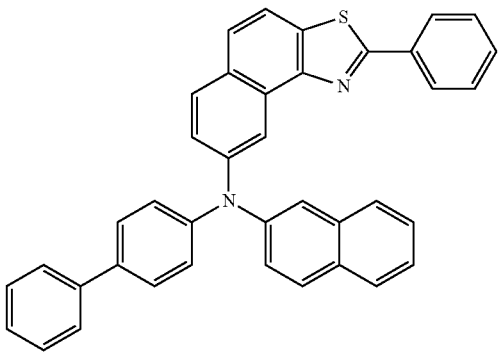
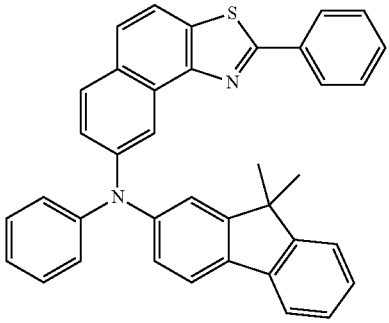
H1-33
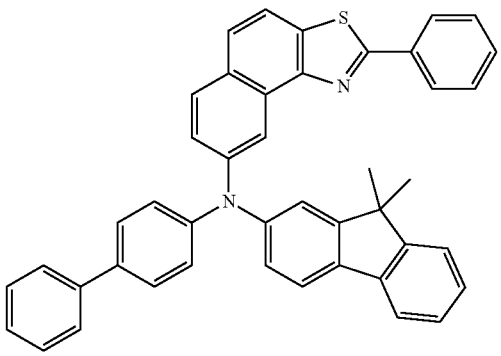

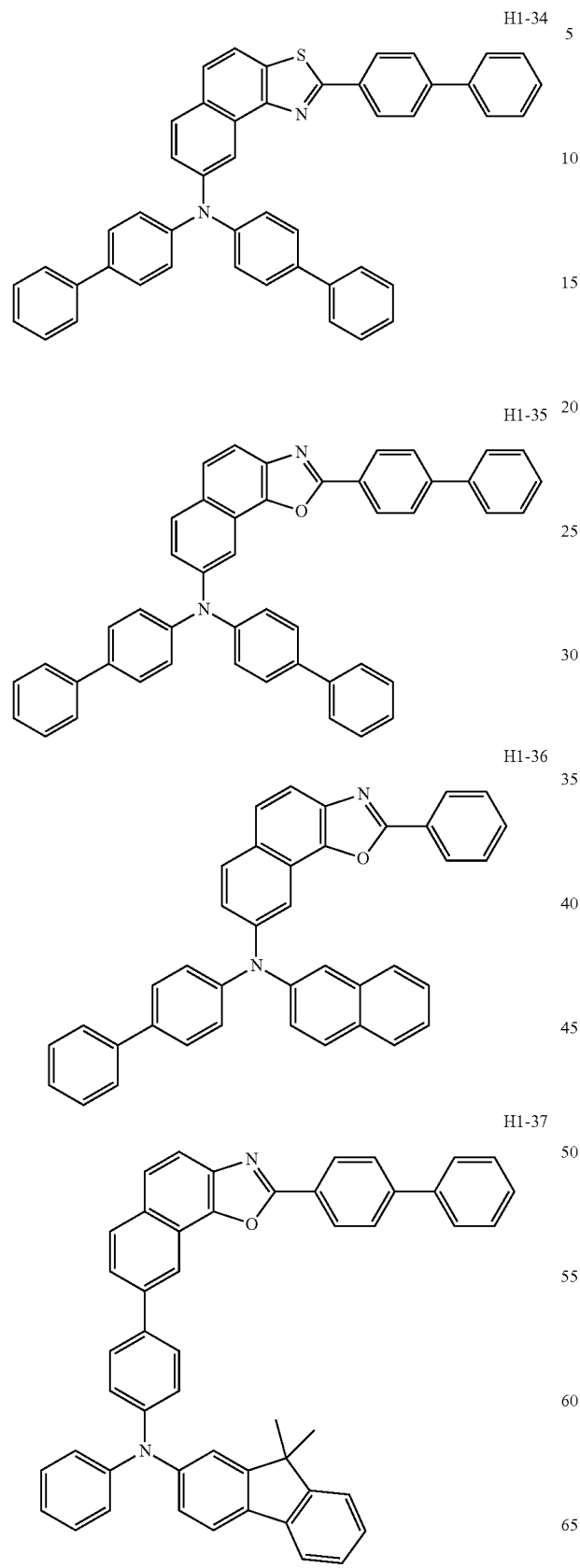
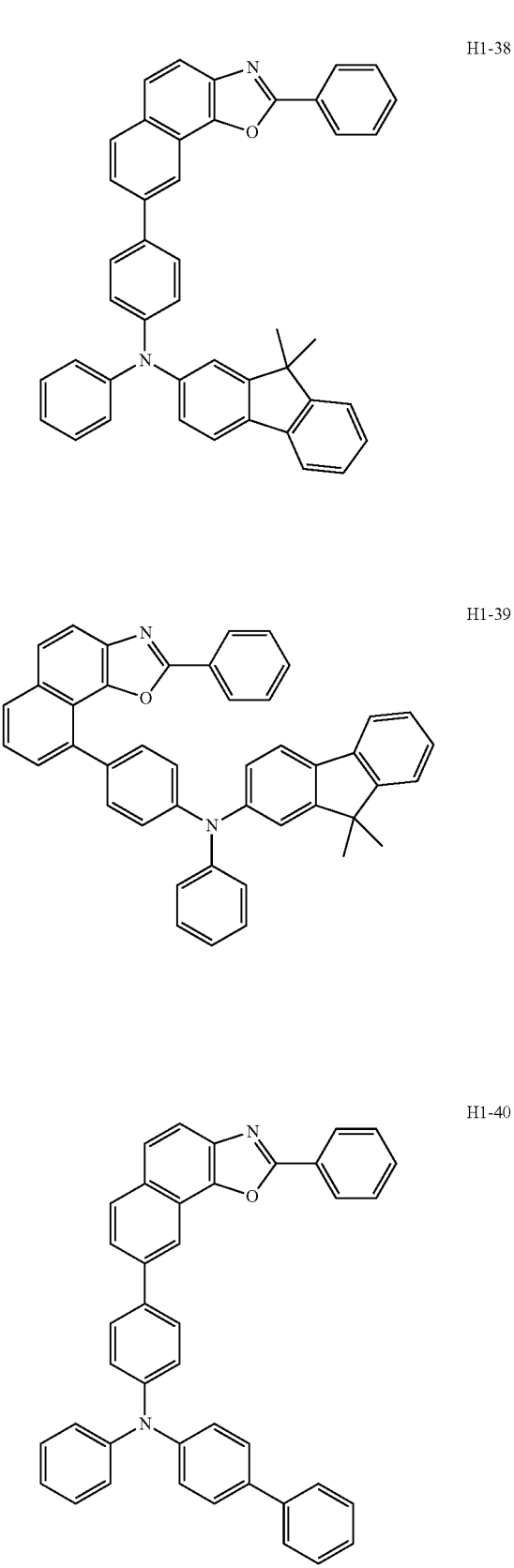

H1-41
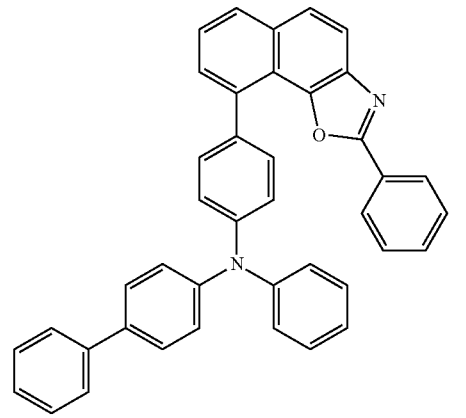
H1-42
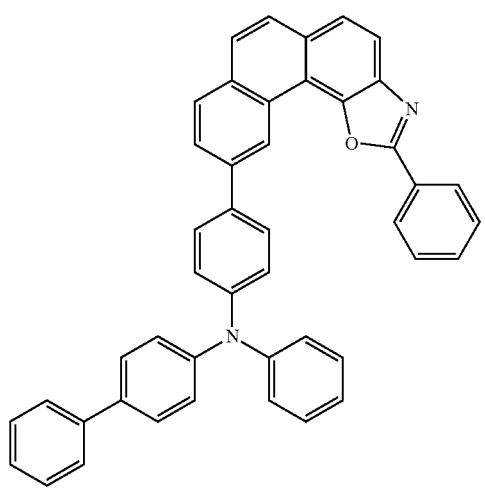
H1-43
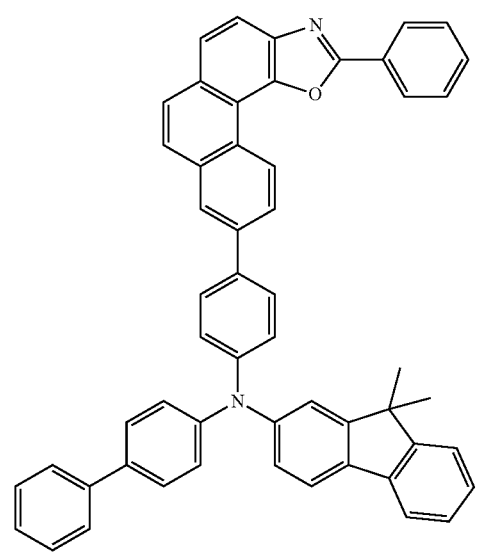
H1-44
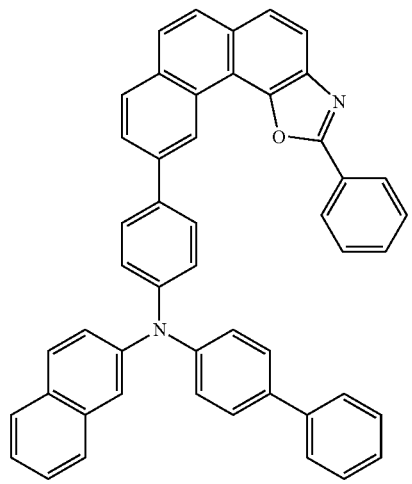
H1-45
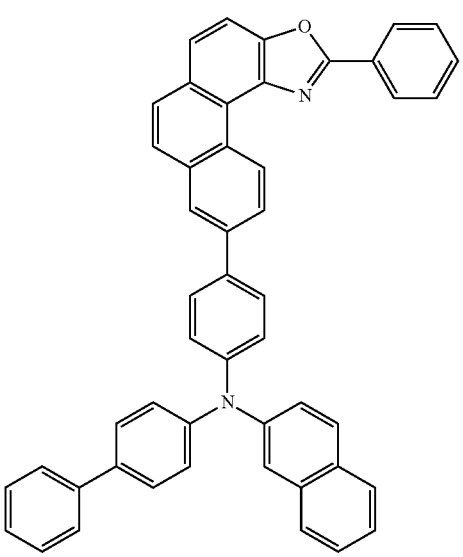
The compound represented by formula 3 may be more specifically illustrated by the following compounds, but is not limited thereto:
H2-1
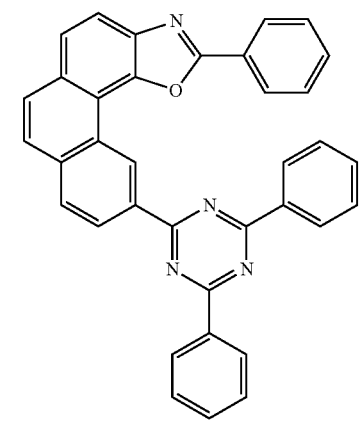

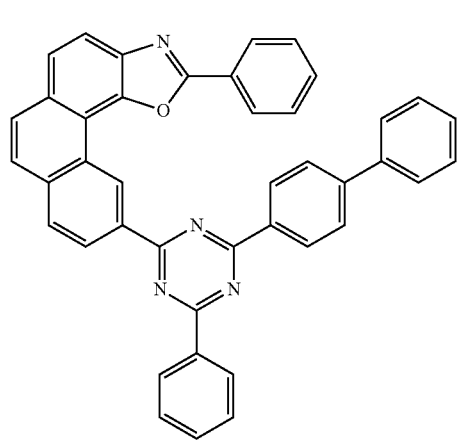
H2-2
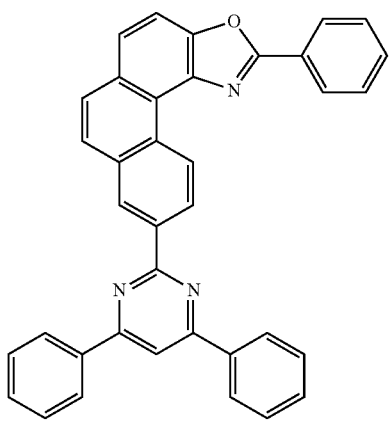
H2-5
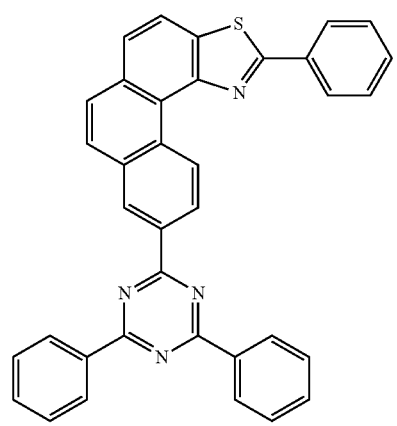
H2-3
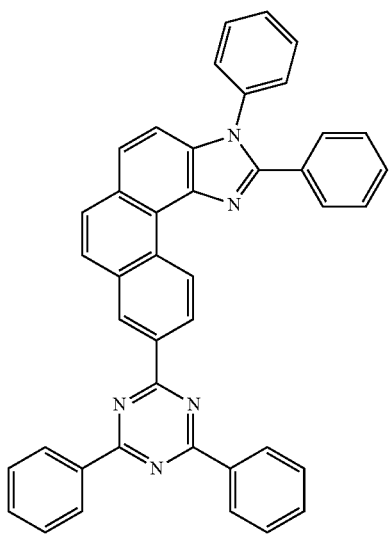
H2-6
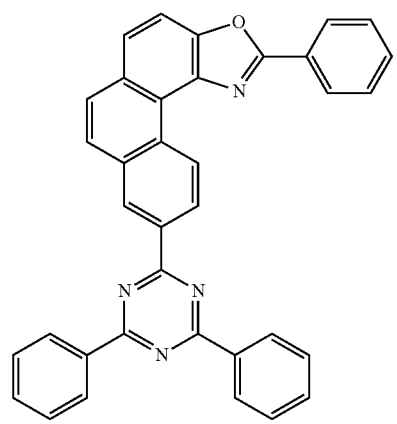
H2-4
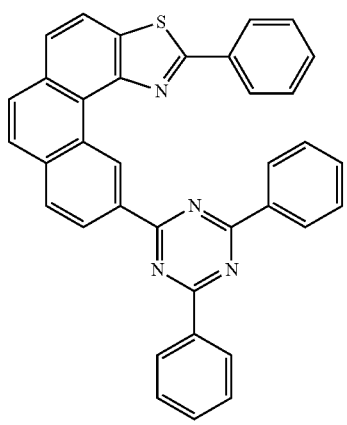
H2-7

-continued
H2-8
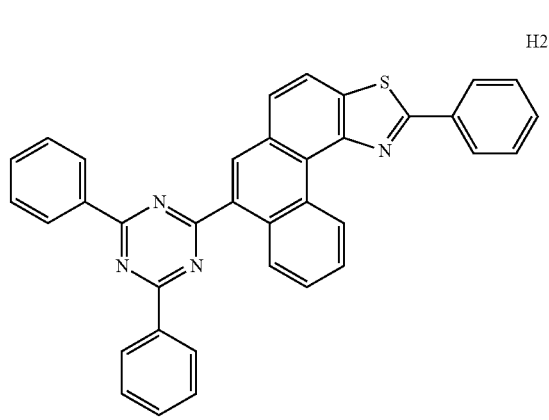
H2-9
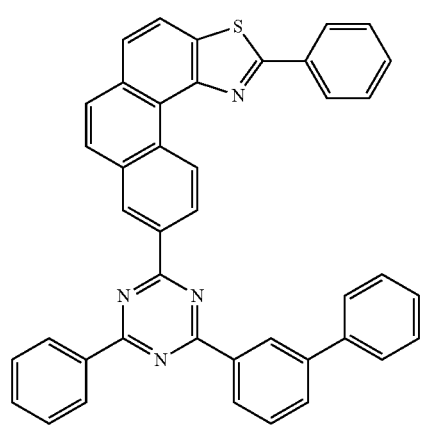
H2-10
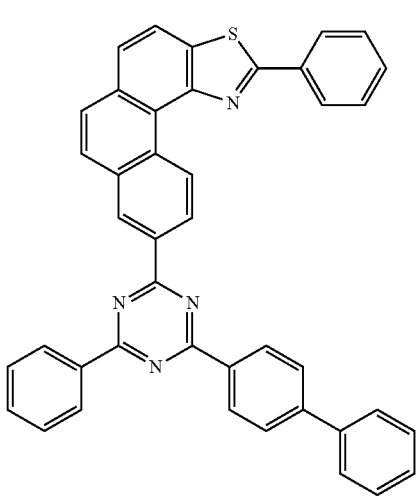
-continued
H2-11
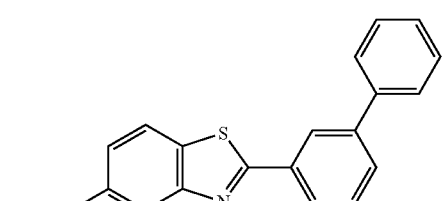
H2-12
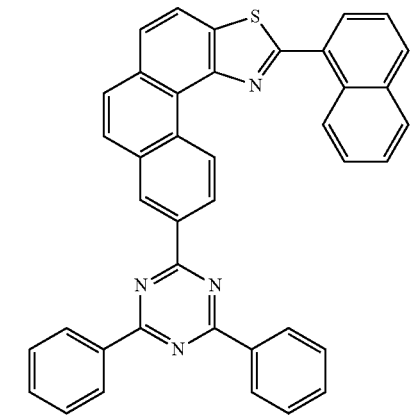
H2-13
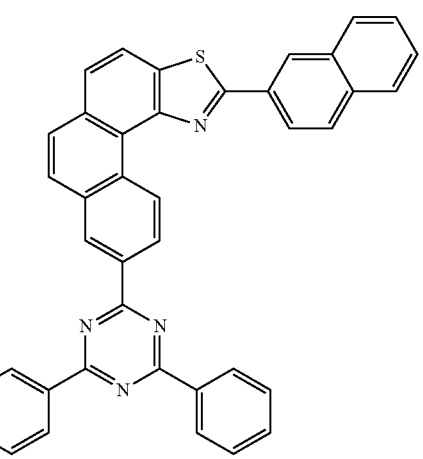

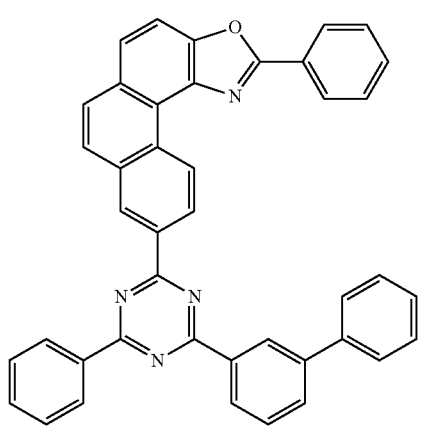
H2-14
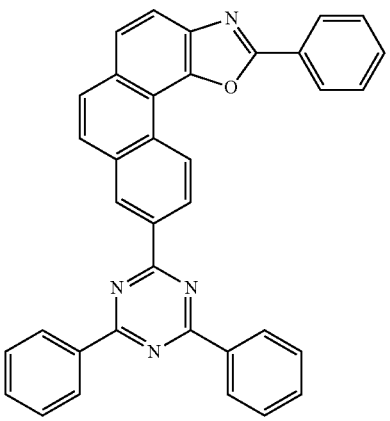
H2-17
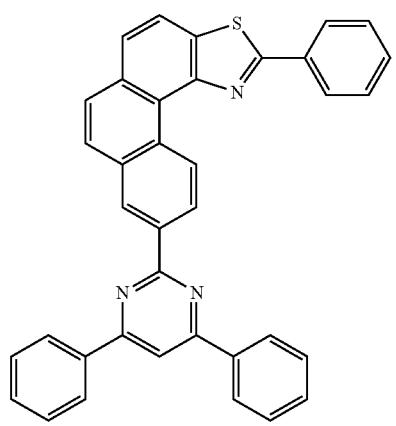
H2-15
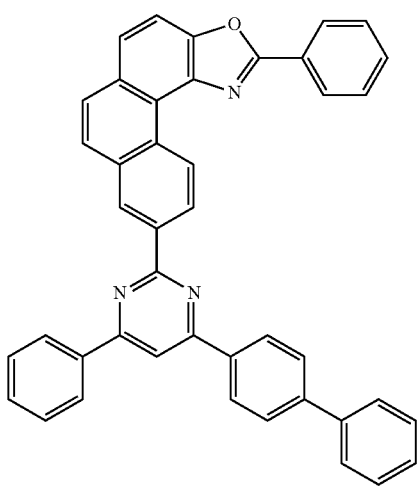
H2-18
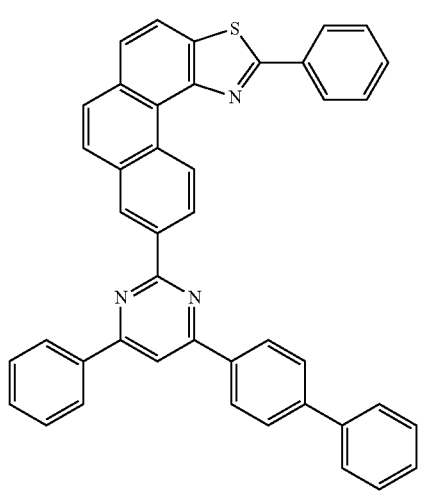
H2-16
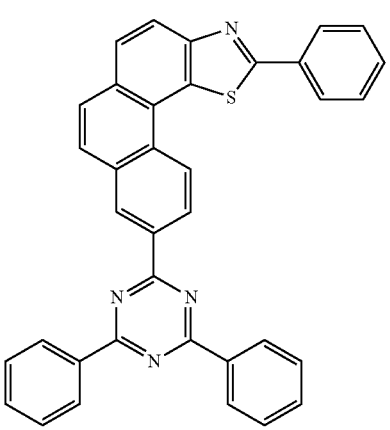
H2-19

H2-20
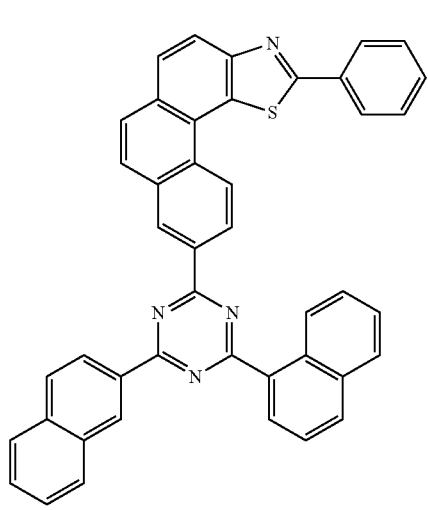
H2-23
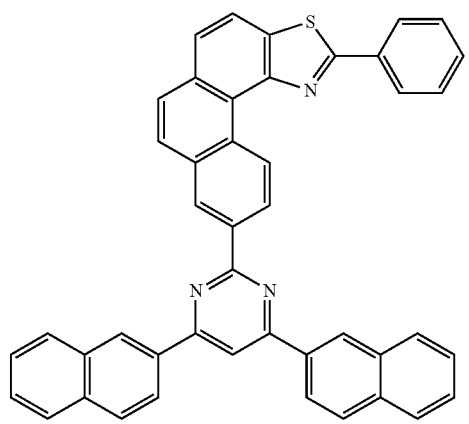
H2-21
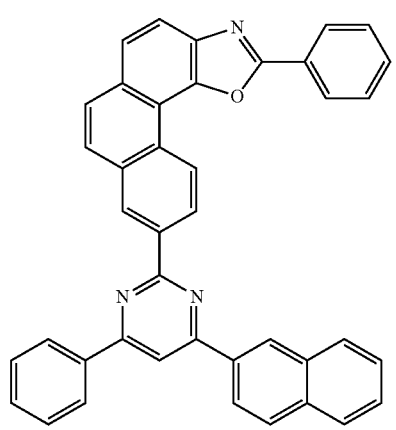
H2-24
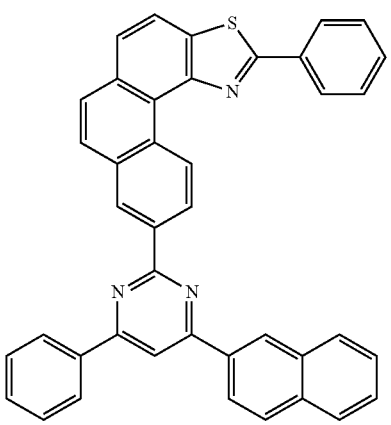
H2-22
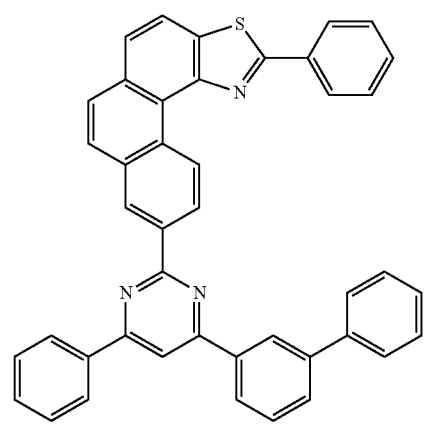
H2-25
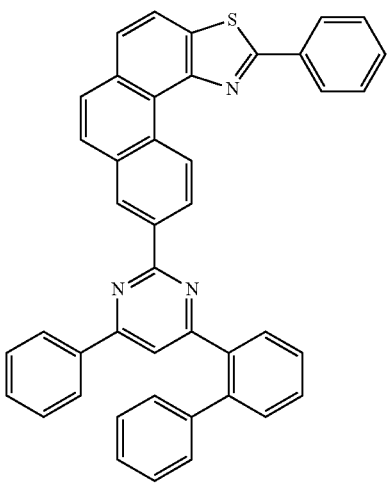

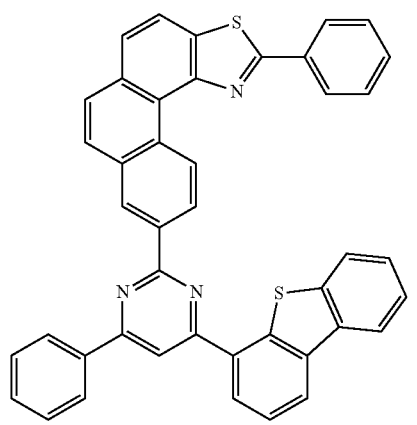
H2-27
H2-28
H2-26
H2-29
H2-30
H2-31

-continued
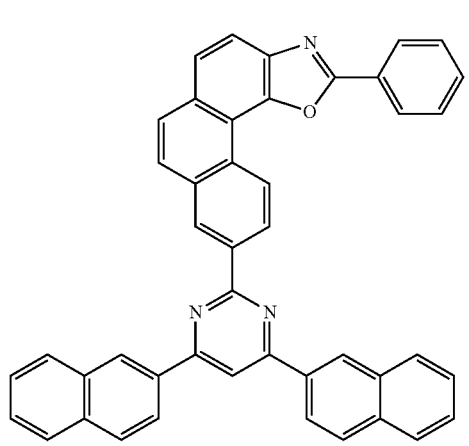
H2-32
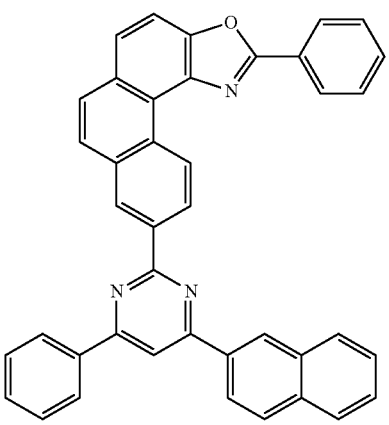
H2-35
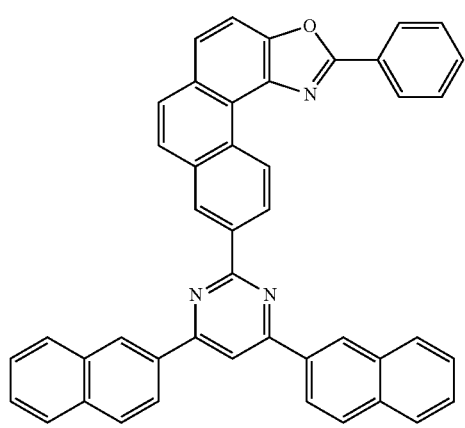
H2-33
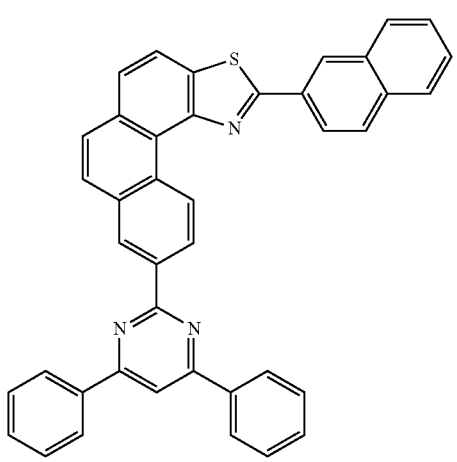
H2-36
H2-34
H2-37

H2-38
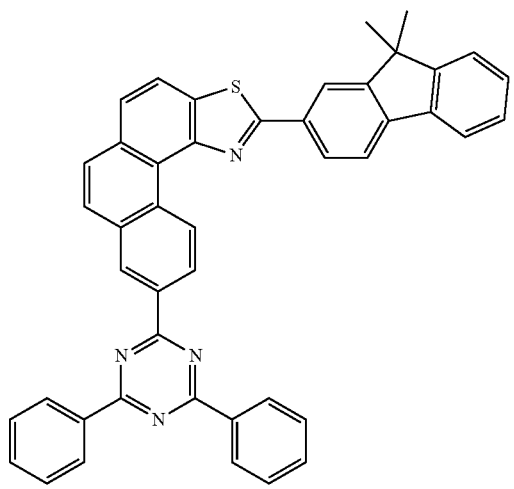
H2-39
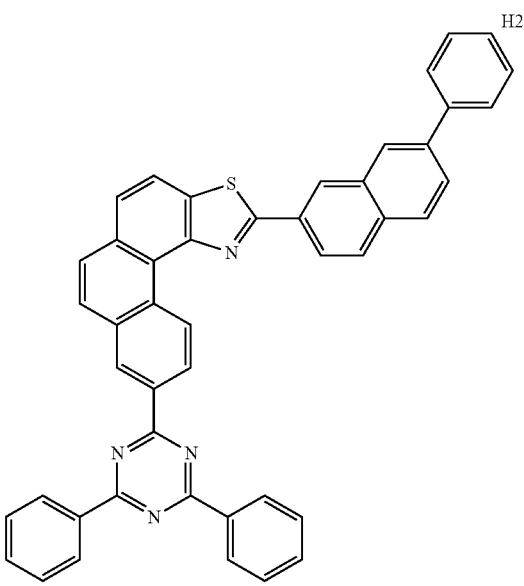
H2-40
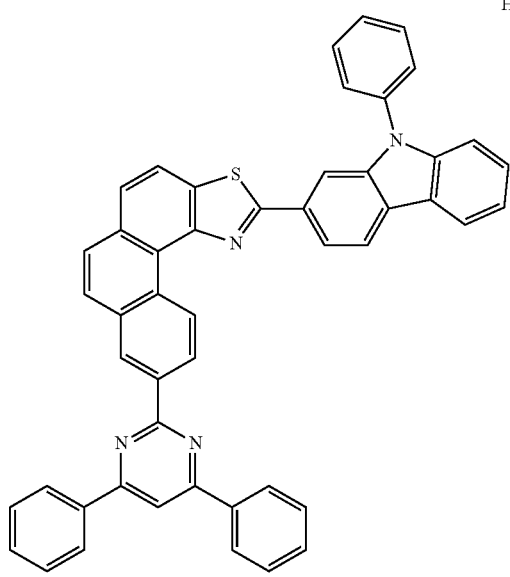
H2-41
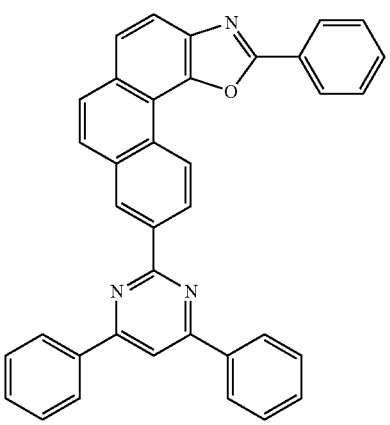
H2-42
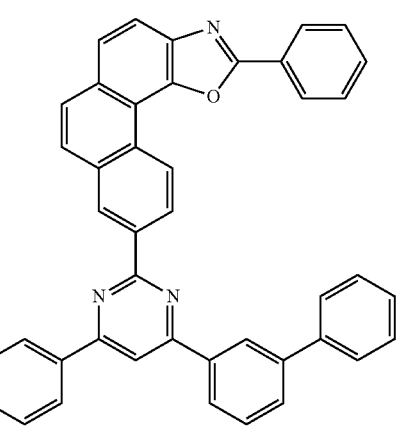
H2-43
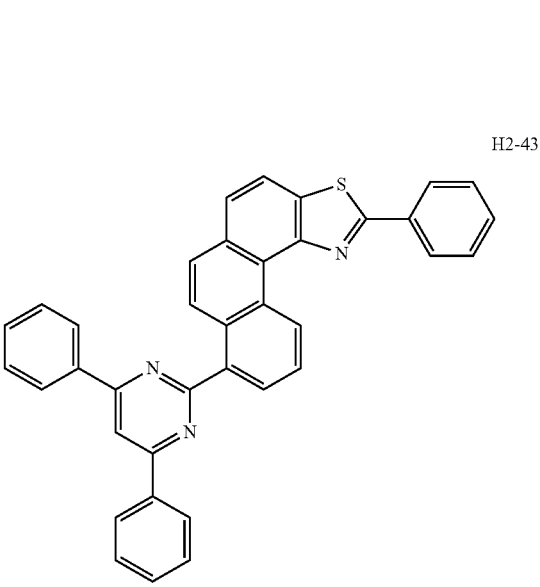

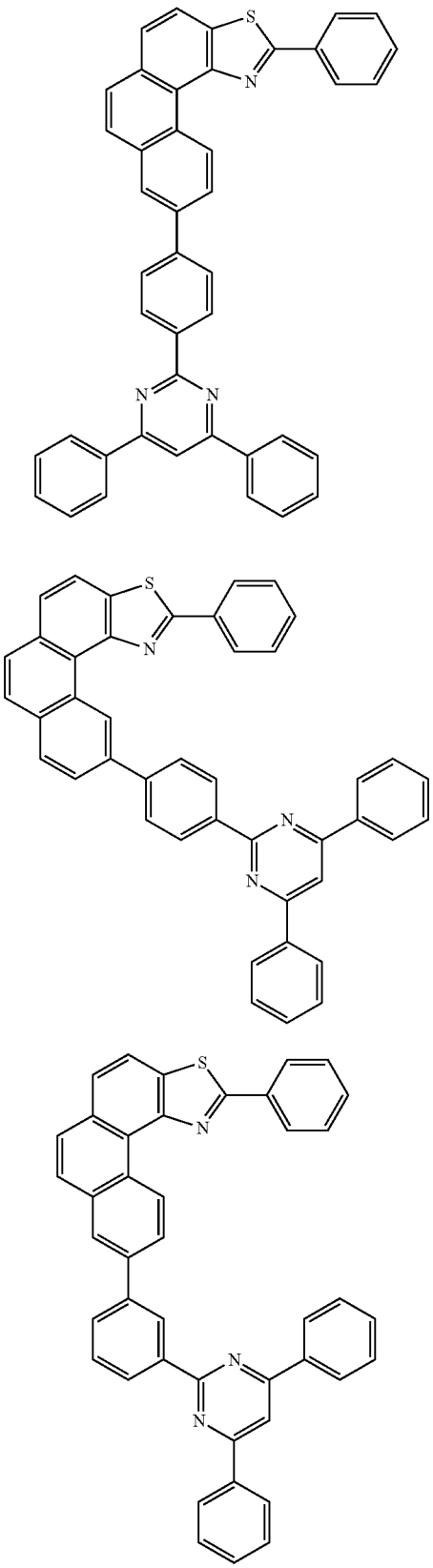
H2-44
H2-45
H2-46
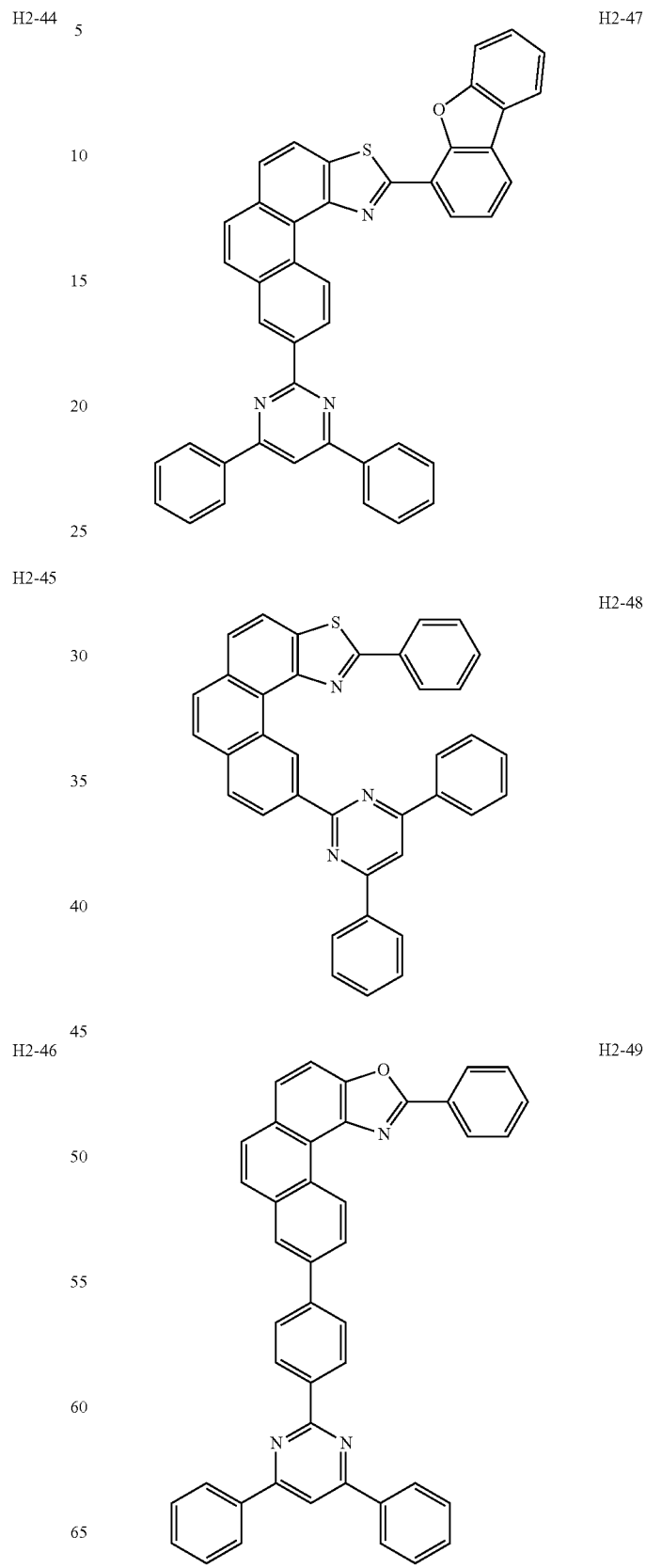
H2-47
H2-48
H2-49

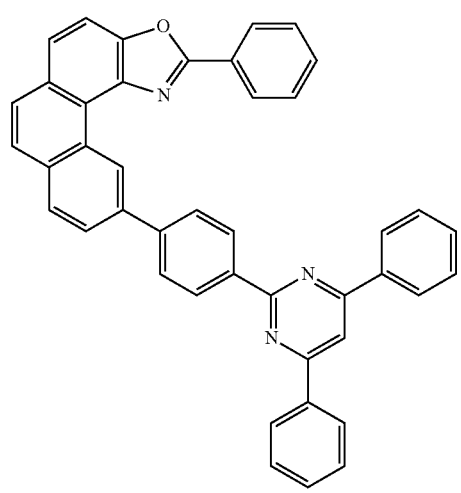
H2-50
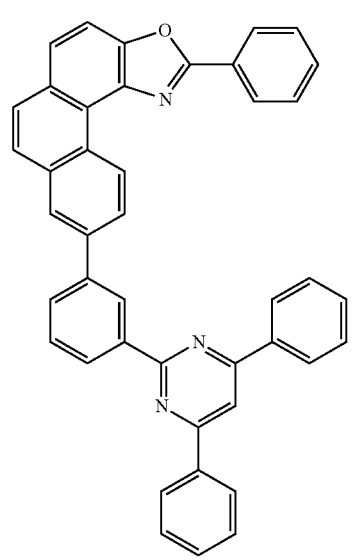
H2-51
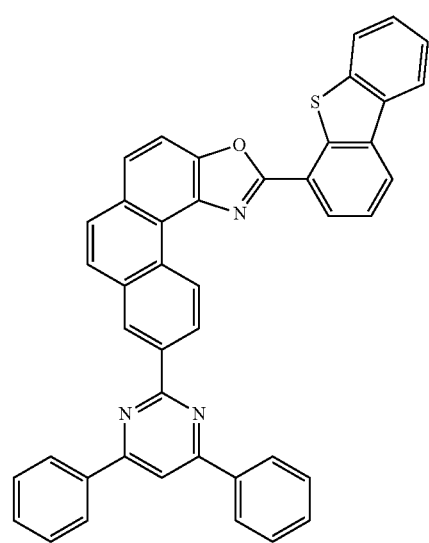
H2-52
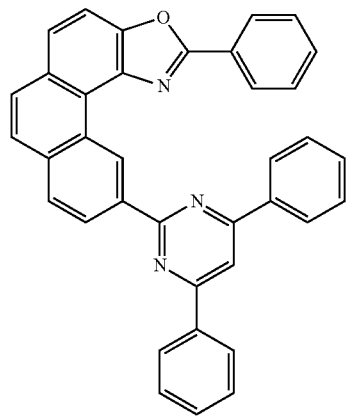
H2-53
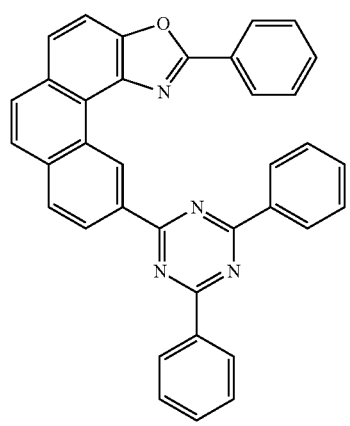
H2-54
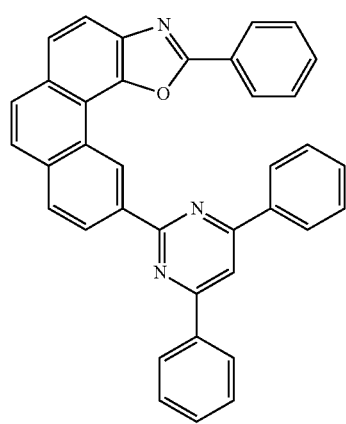
H2-55

H2-56
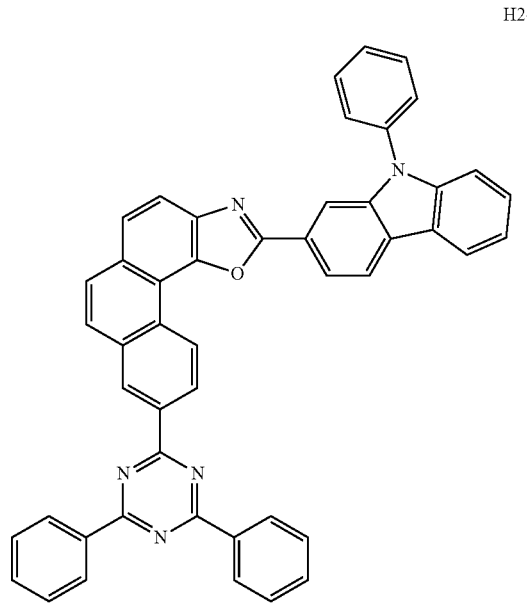
H2-57
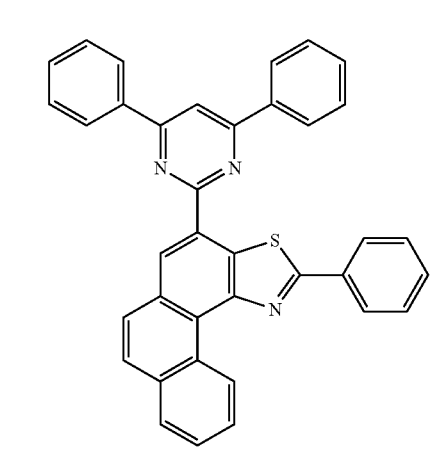
H2-58
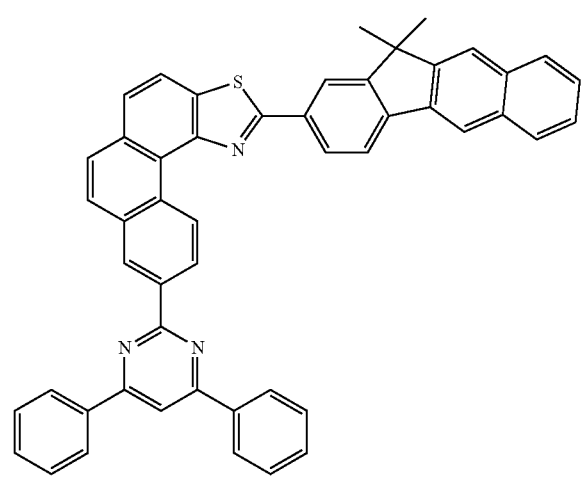
H2-59
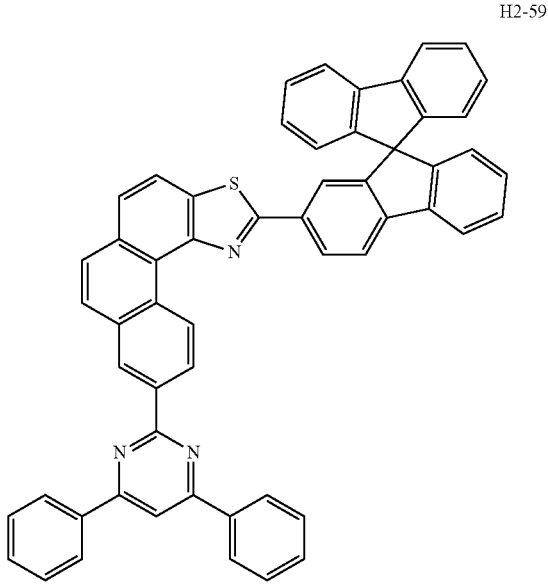
H2-60
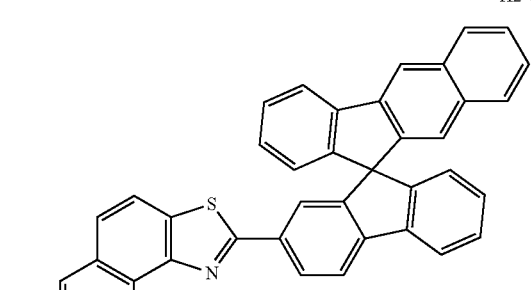
H2-61
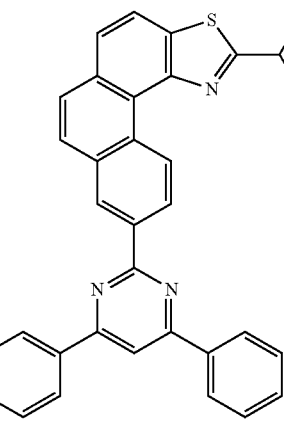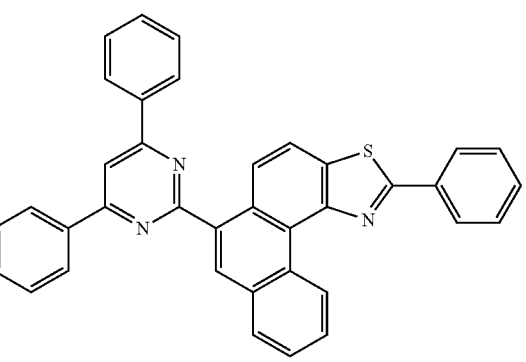

H2-62
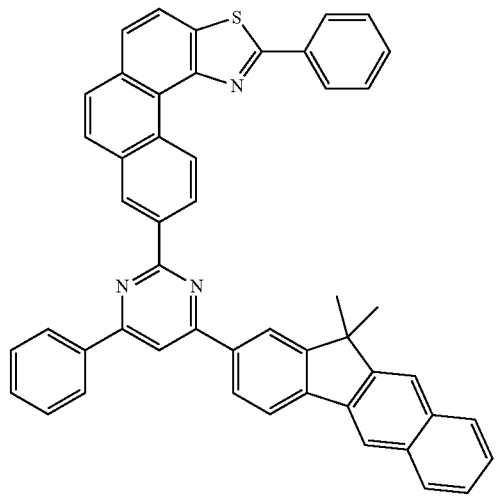
H2-63
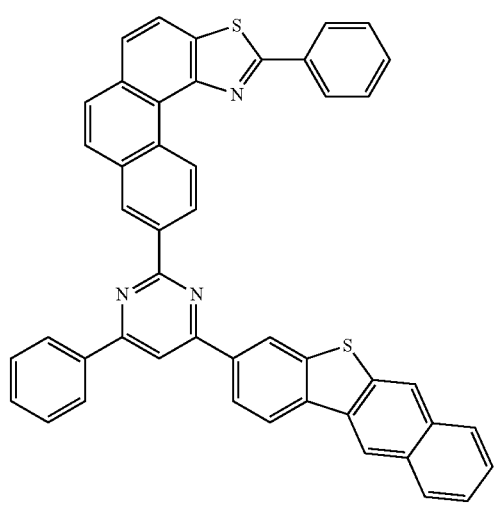
H2-64
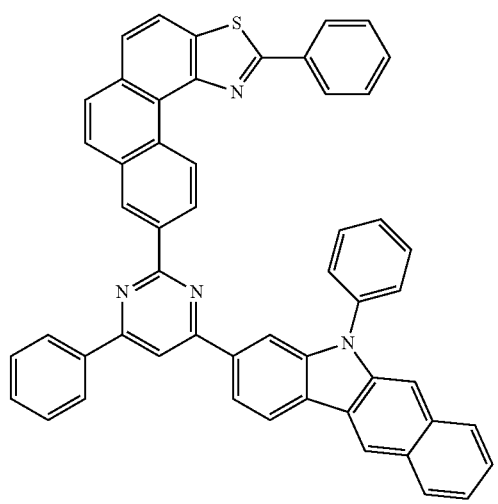
H2-65
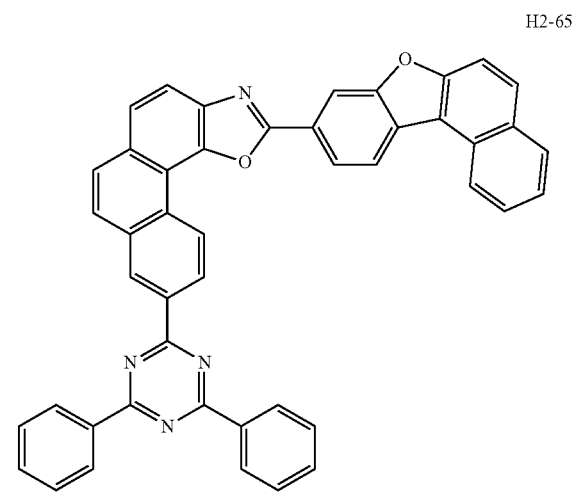
H2-66
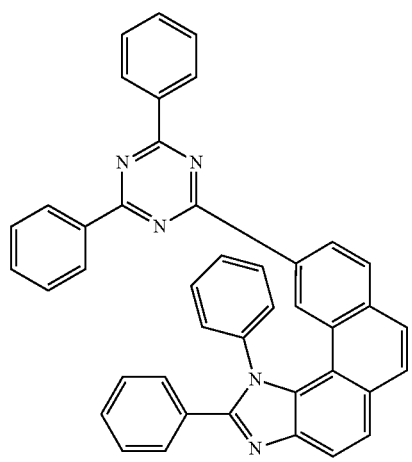
H2-67
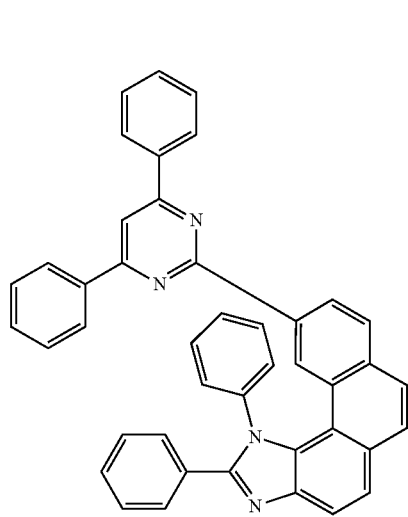

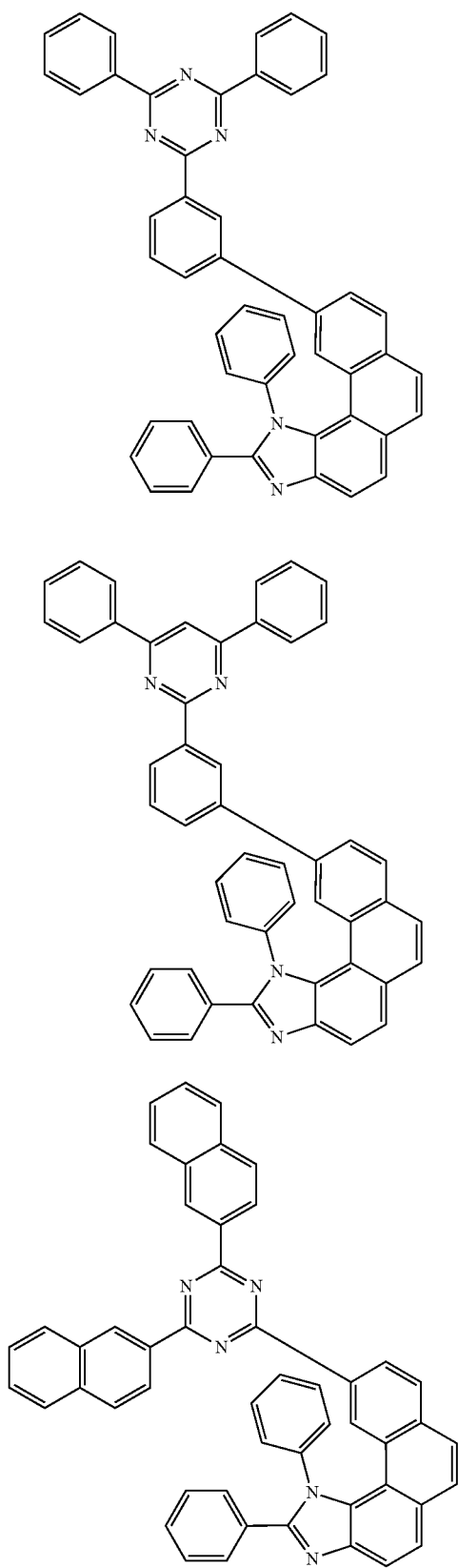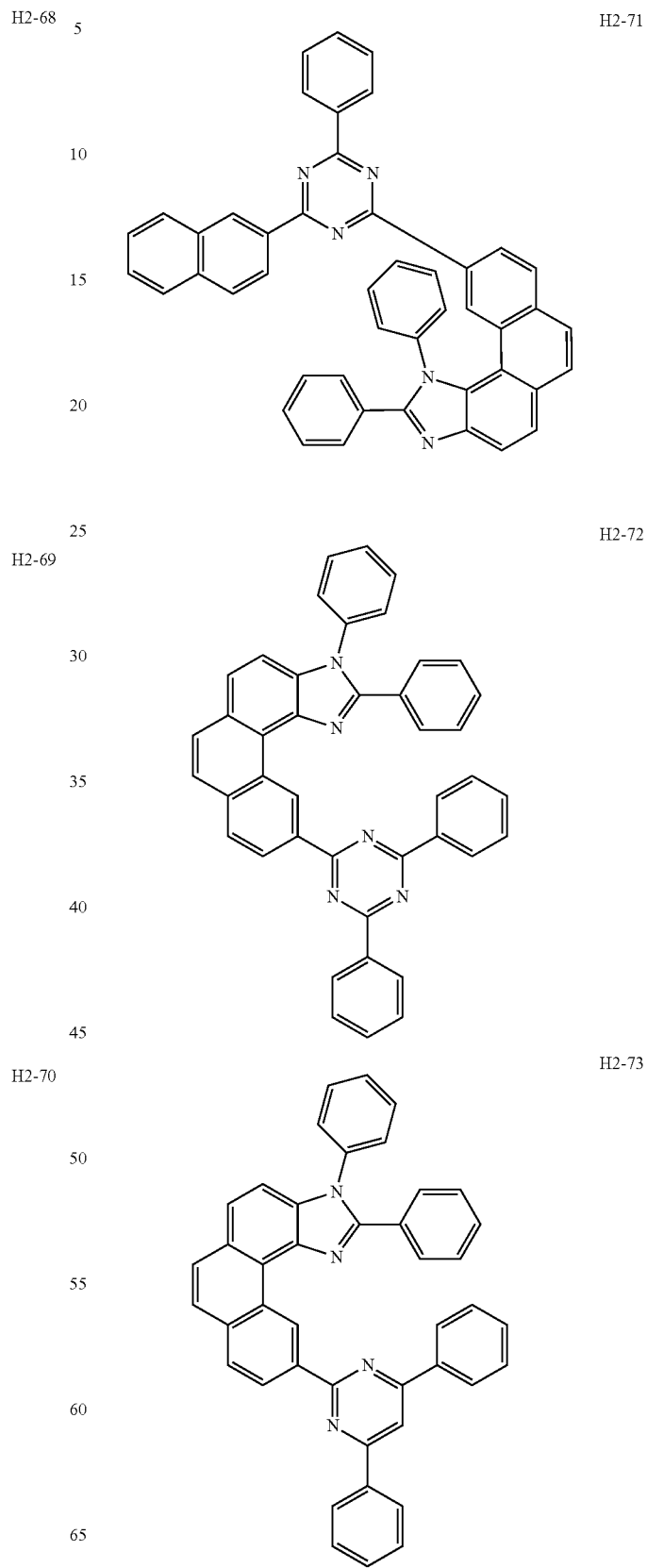

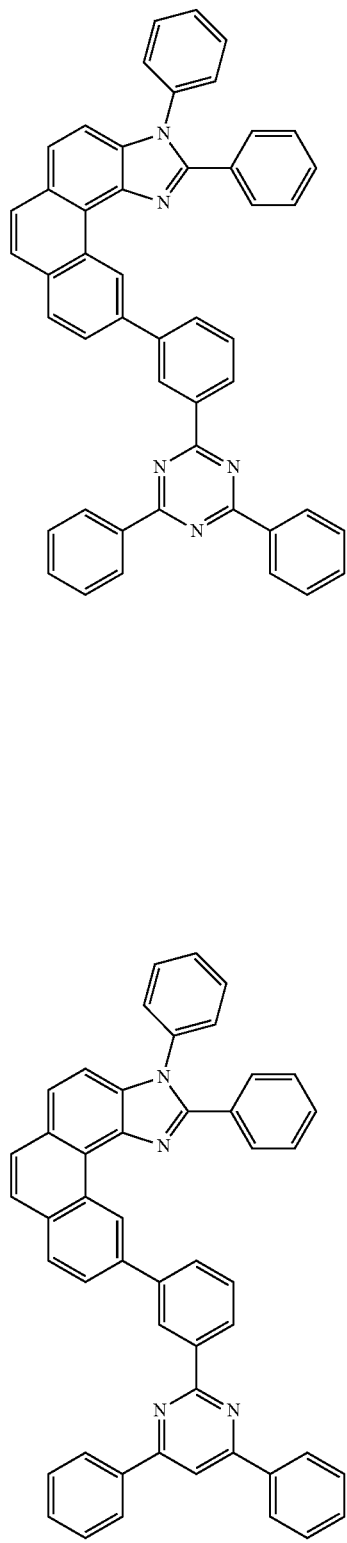
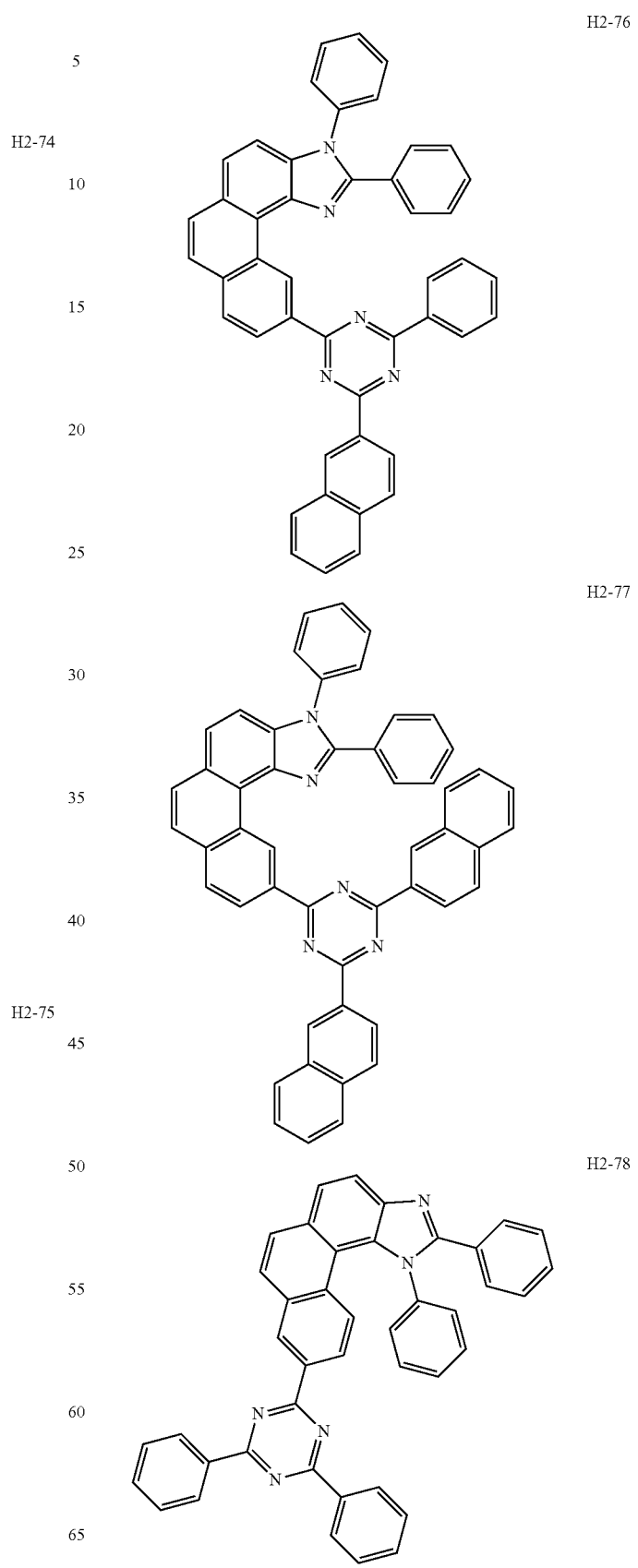

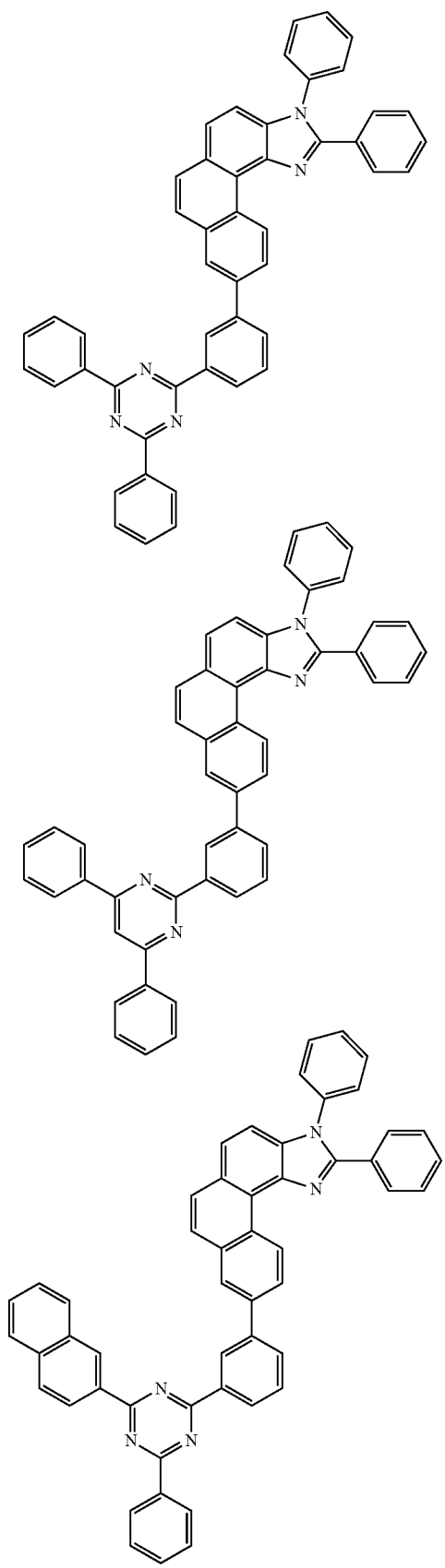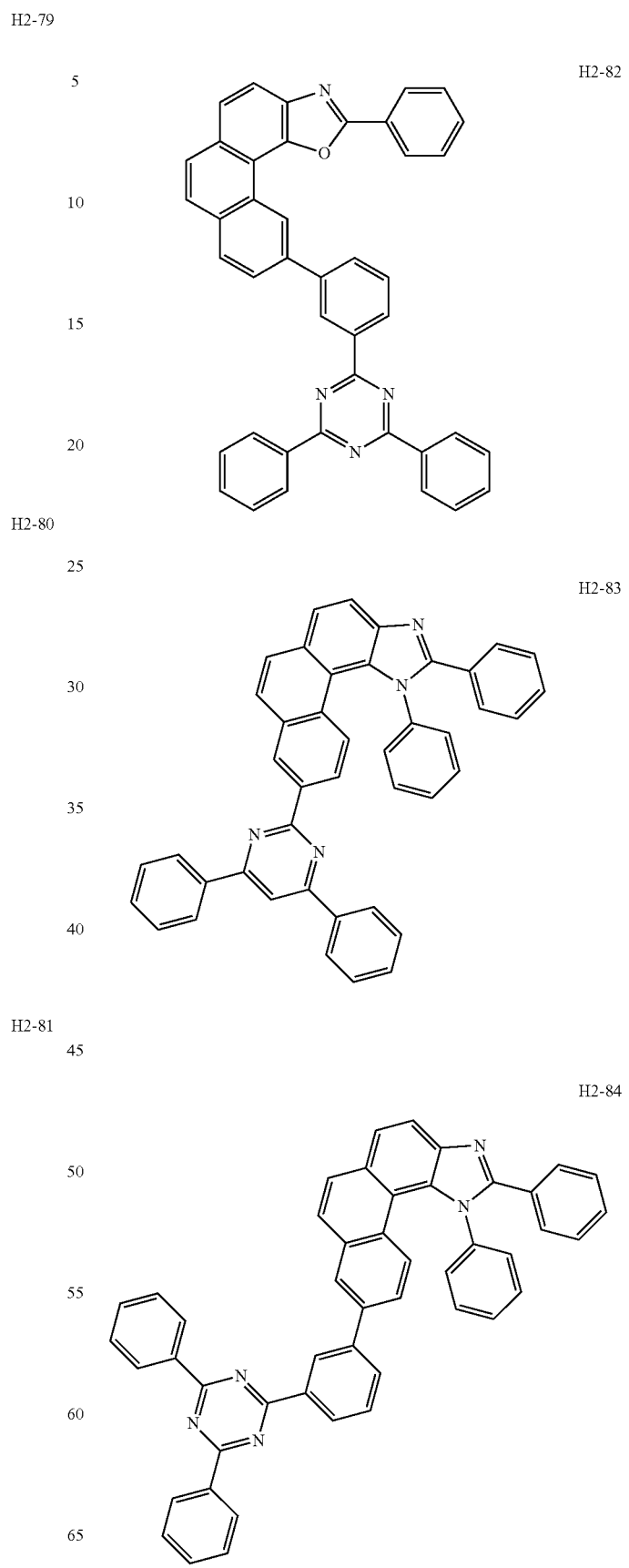

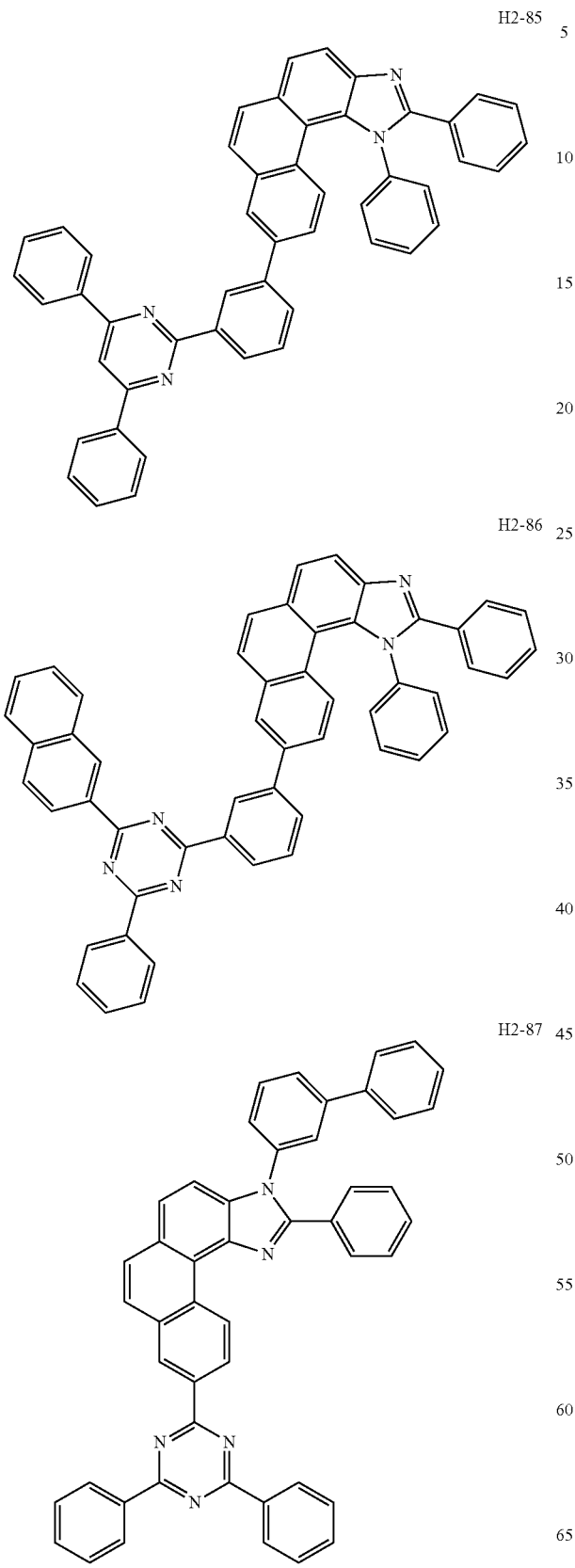

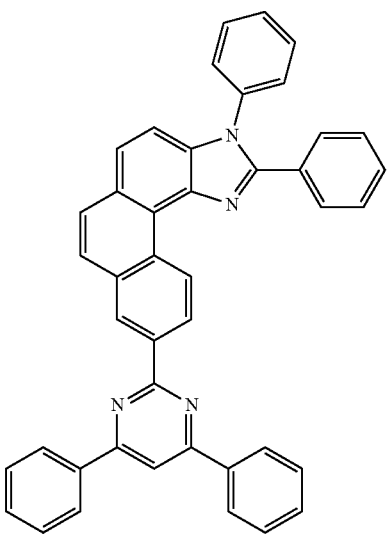

The organic electroluminescent device according to the present disclosure comprises an anode; a cathode; and at least one organic layer between the anode and the cathode. The organic layer comprises a light-emitting layer comprising a host and a phosphorescent dopant. The host comprises a plurality of host compounds, at least a first host compound of the plurality of host compounds is represented by formula 1 or 2 above, and a second host compound is represented by formula 3 above.

In the present disclosure, the light-emitting layer is a layer from which light is emitted, and can be a single layer or a multi-layer of which two or more layers are stacked. In the light-emitting layer, it is preferable that the doping concentration of the dopant compound based on the host compound is less than 20 wt %.

The organic layer may comprise a light-emitting layer, and may further comprise at least one layer selected from a hole injection layer, a hole transport layer, an electron transport layer, an electron injection layer, an interlayer, a hole blocking layer, and an electron blocking layer.

In the organic electroluminescent device of the present disclosure, the weight ratio of the first host compound to the second host compound is in the range of 1:99 to 99:1.

The dopant comprised in the organic electroluminescent device according to the present disclosure is preferably at least one phosphorescent dopant. The phosphorescent dopant material comprised in the organic electroluminescent device according to the present disclosure is not particularly limited, but may be preferably selected from metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescence device of the present disclosure may comprise the compound represented by the following Formula 101, but is not limited thereto:

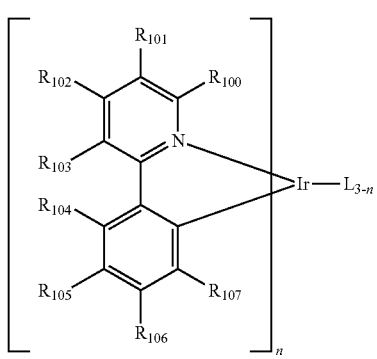

(101)

wherein, L is selected from the following structure 1 or 2:

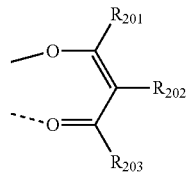

structure (1)

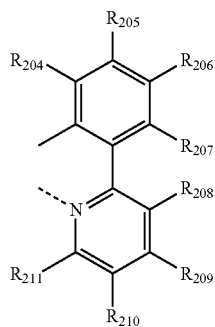

structure (2)

$R_{100}$ to $R_{103}$ each independently represent hydrogen, deuterium, halogen, a halogen-substituted or unsubstituted (C1-C30)alkyl, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or $R_{100}$ to $R_{103}$ may be linked to adjacent substituents to form a substituted or unsubstituted fused ring, e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline; $R_{104}$ to $R_{107}$ each independently represent hydrogen, deuterium, halogen, a halogen-substituted or unsubstituted (C1-C30)alkyl, a substituted or unsubstituted (C3-C30)cycloalkyl, a substituted or unsubstituted (C6-C30)aryl, a substituted or unsubstituted (3- to 30-membered)heteroaryl, cyano, or a substituted or unsubstituted (C1-C30)alkoxy; or $R_{104}$ to $R_{107}$ may be linked to adjacent substituents to form a substituted or unsubstituted fused ring, e.g., a substituted or unsubstituted naphthyl, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine; $R_{201}$ to $R_{211}$ each independently represent hydrogen, deuterium, halogen, a halogen-substituted or unsubstituted (C1-C30)alkyl, a substituted or unsubstituted (C3-C30)cycloalkyl, a substituted or unsubstituted (C6-C30)aryl; or $R_{201}$ to $R_{211}$ may be linked to adjacent substituents to form a substituted or unsubstituted fused ring; n represents an integer of 1 to 3.

The specific examples of the dopant material include the following:

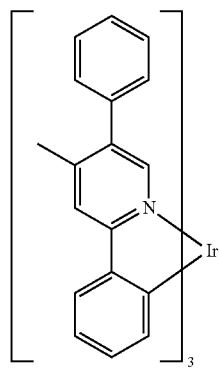

D-1

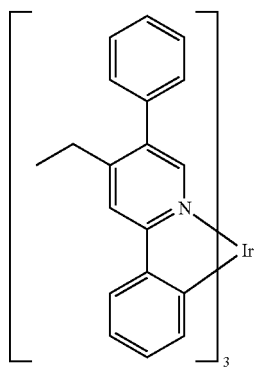

D-2

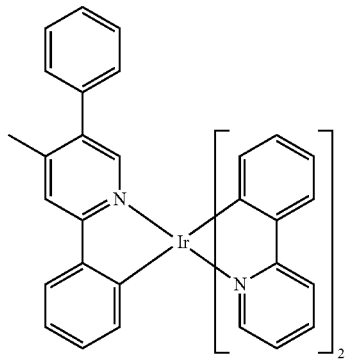

D-3

D-4
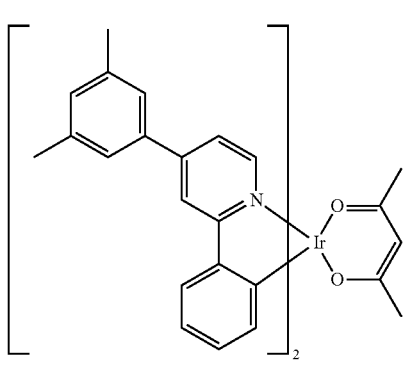
D-5
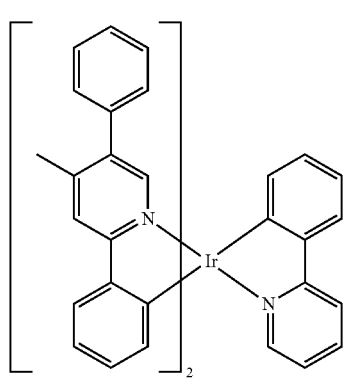
D-6
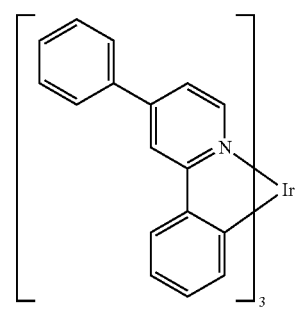
D-7
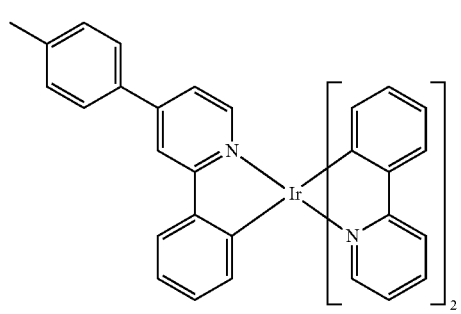
D-8
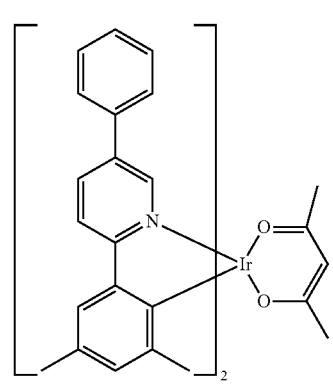
D-9
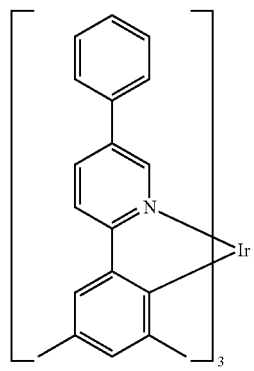
D-10
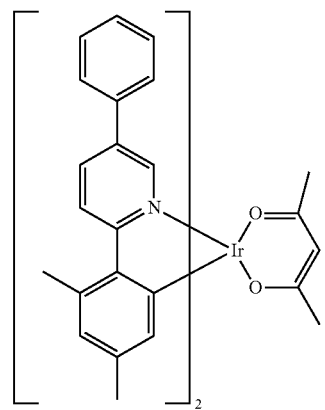
D-11
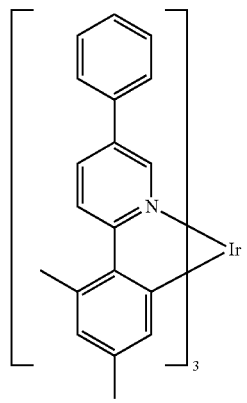

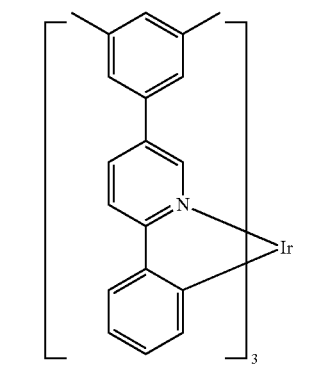
D-12
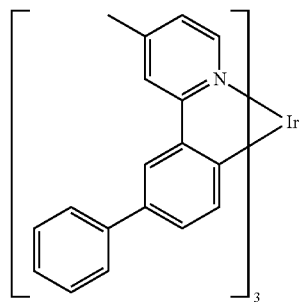
D-16
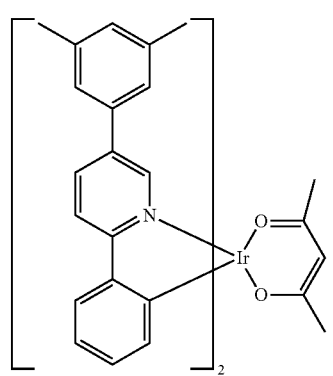
D-13
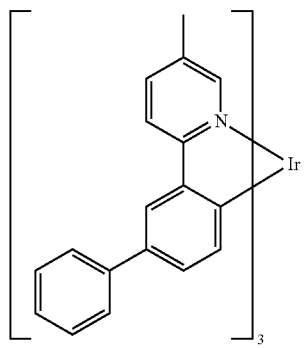
D-17
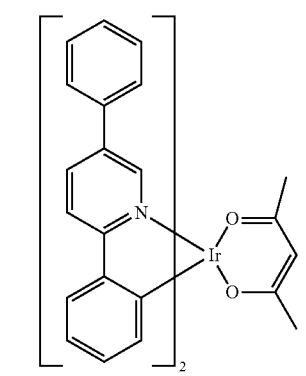
D-14
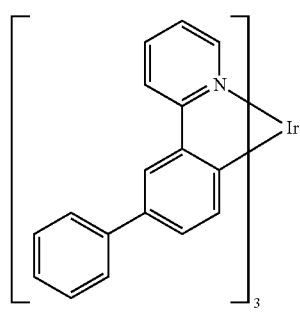
D-18
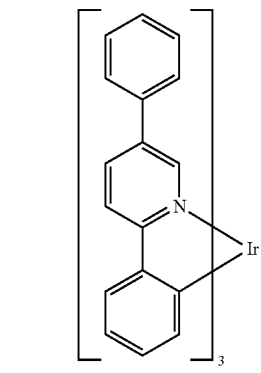
D-15
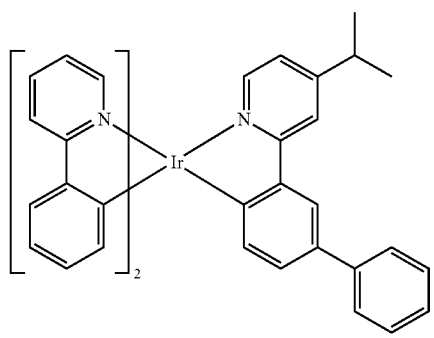
D-19
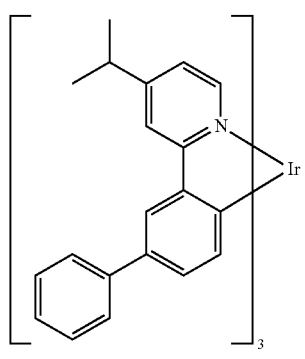
D-20

-continued
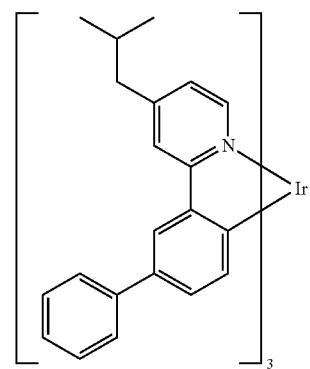
D-21
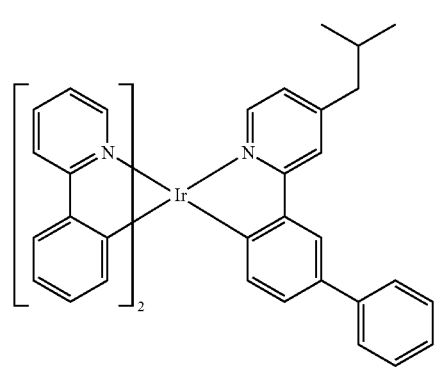
D-22
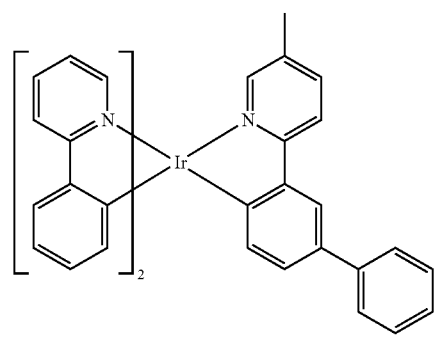
D-23
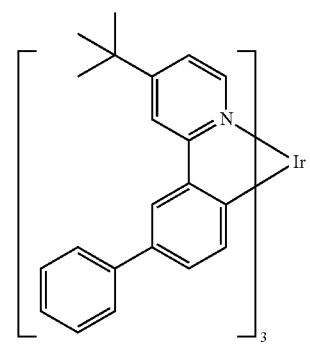
D-24
-continued
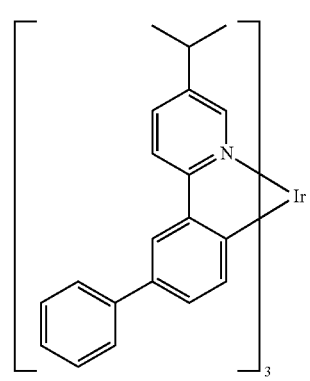
D-25
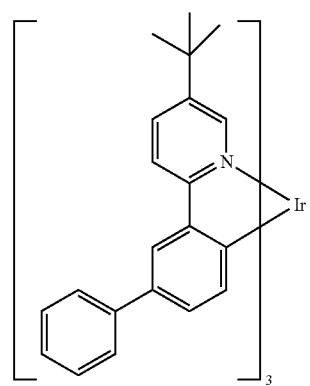
D-26
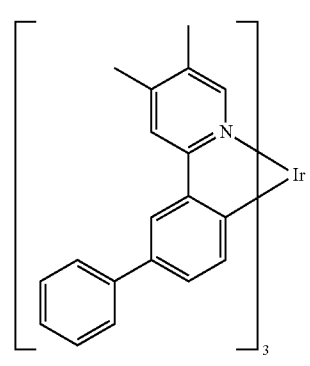
D-27
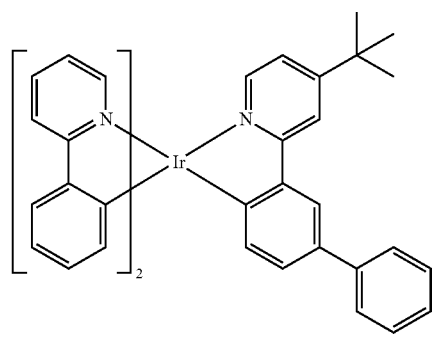
D-28

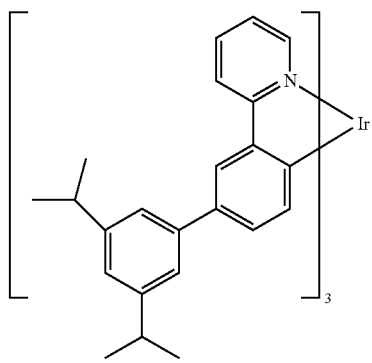 D-29
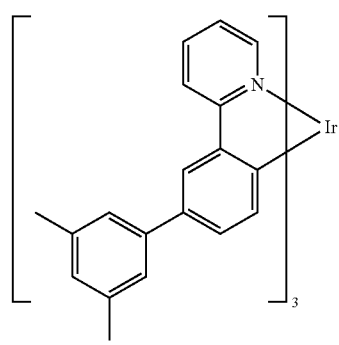 D-30
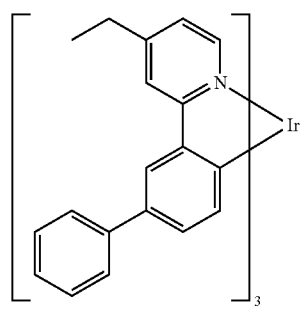 D-31
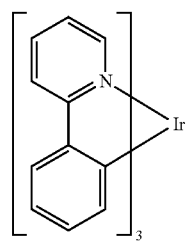 D-32
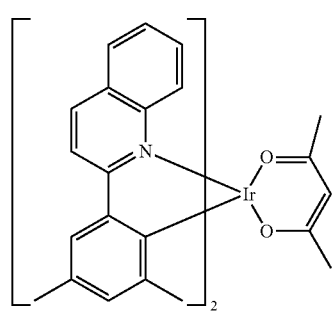 D-33
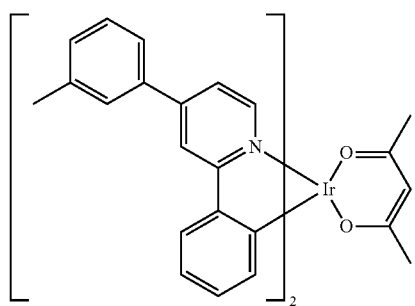 D-34
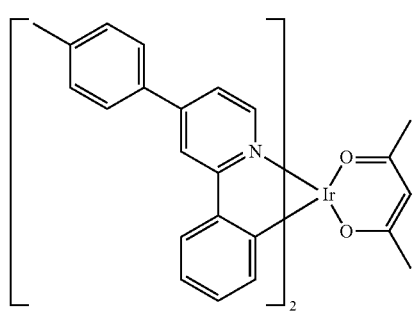 D-35
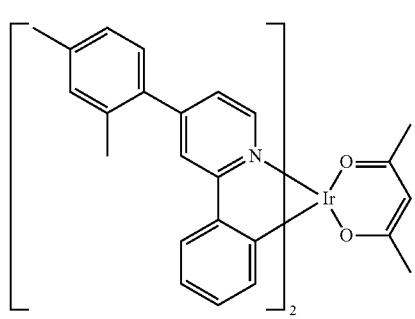 D-36
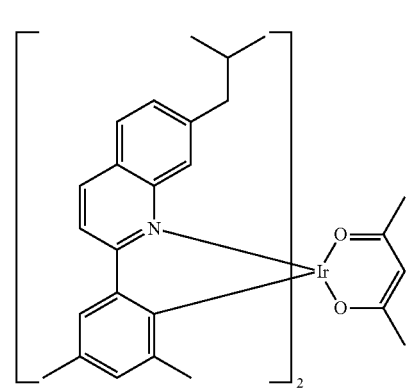 D-37
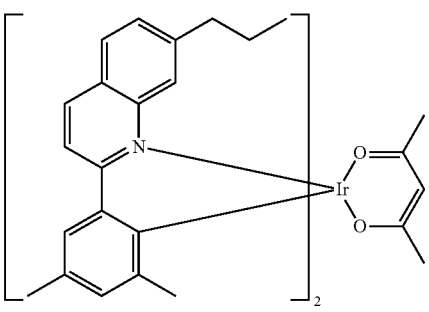 D-38

-continued
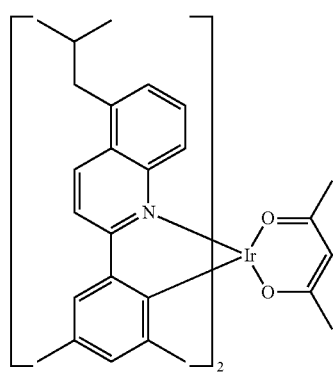
D-39
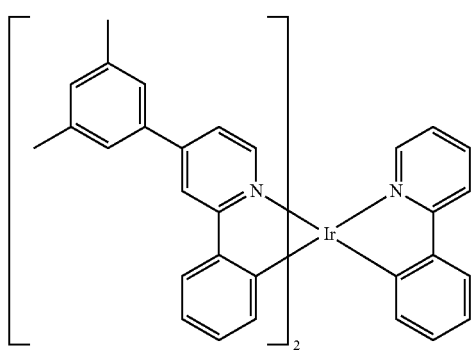
D-40
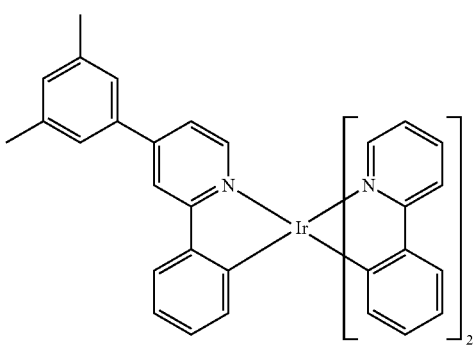
D-41
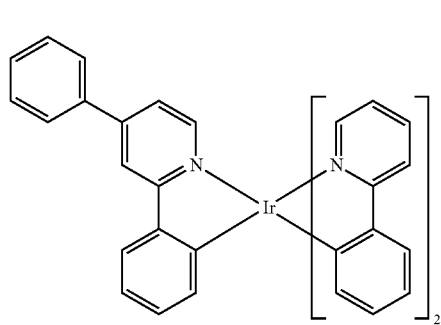
D-42
-continued
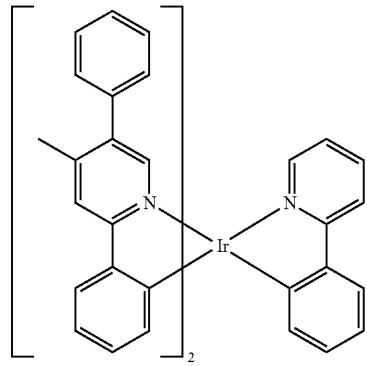
D-43
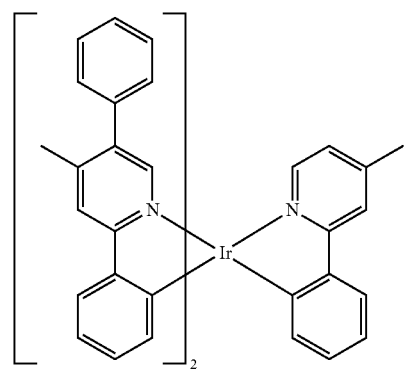
D-44
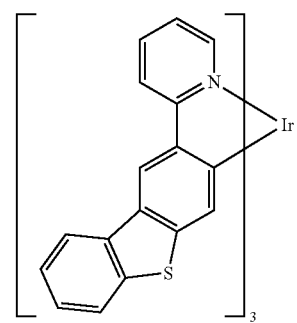
D-45
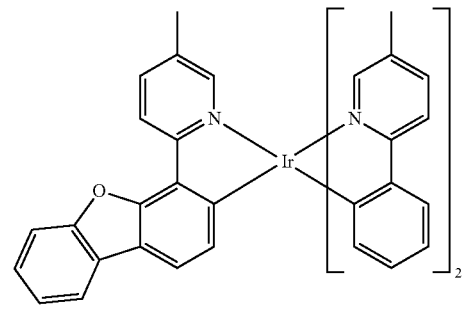
D-46

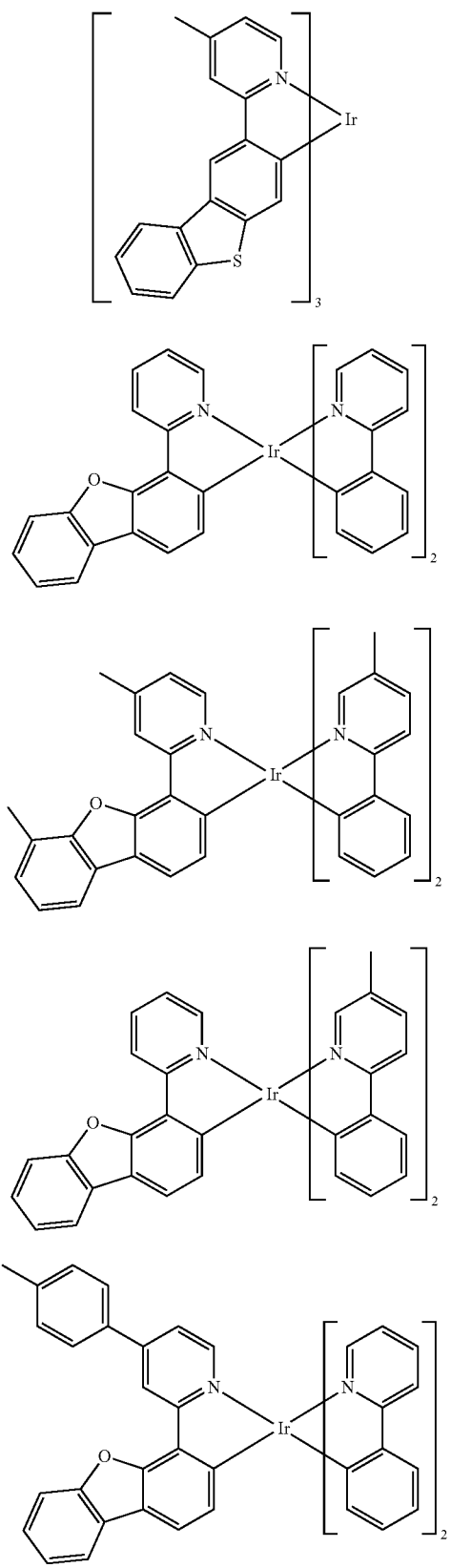
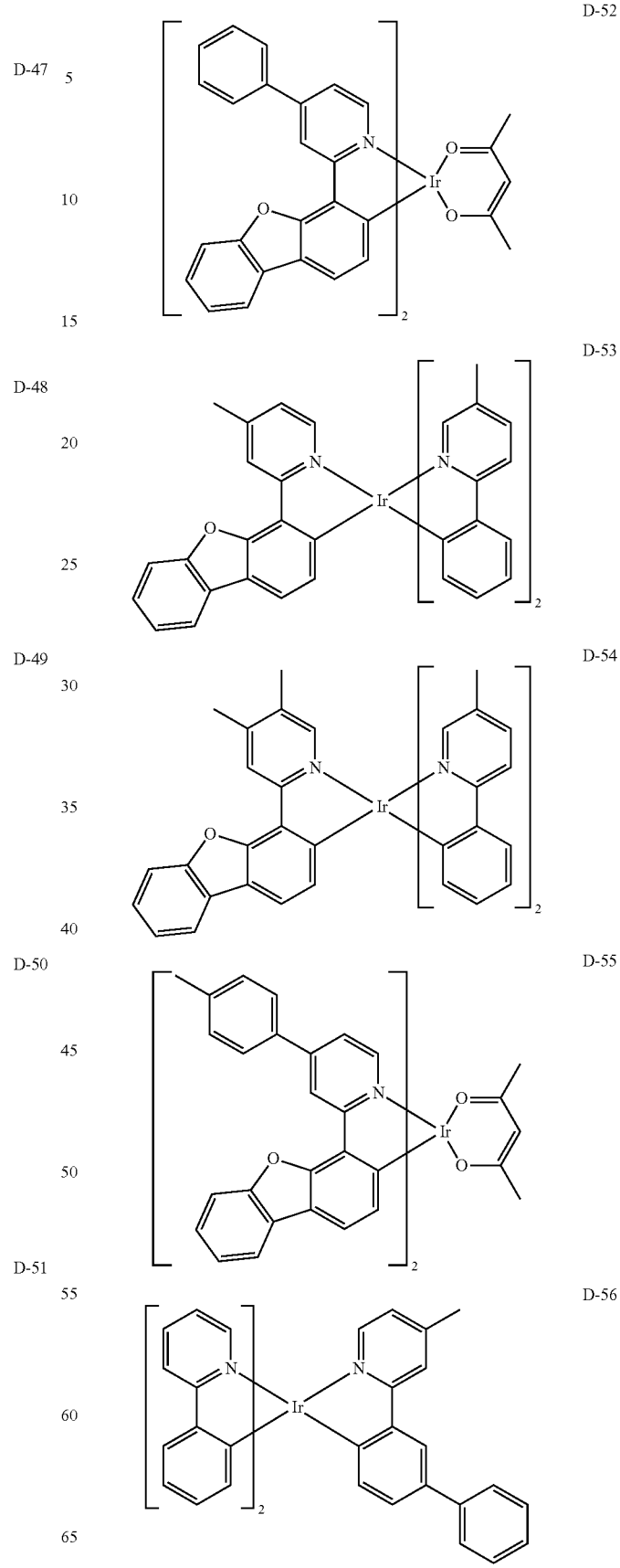

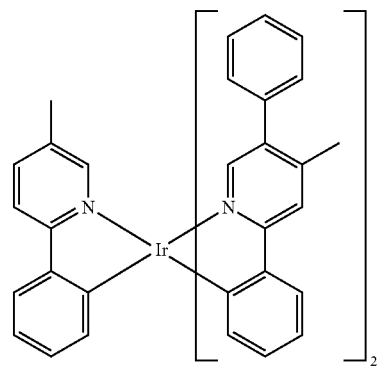
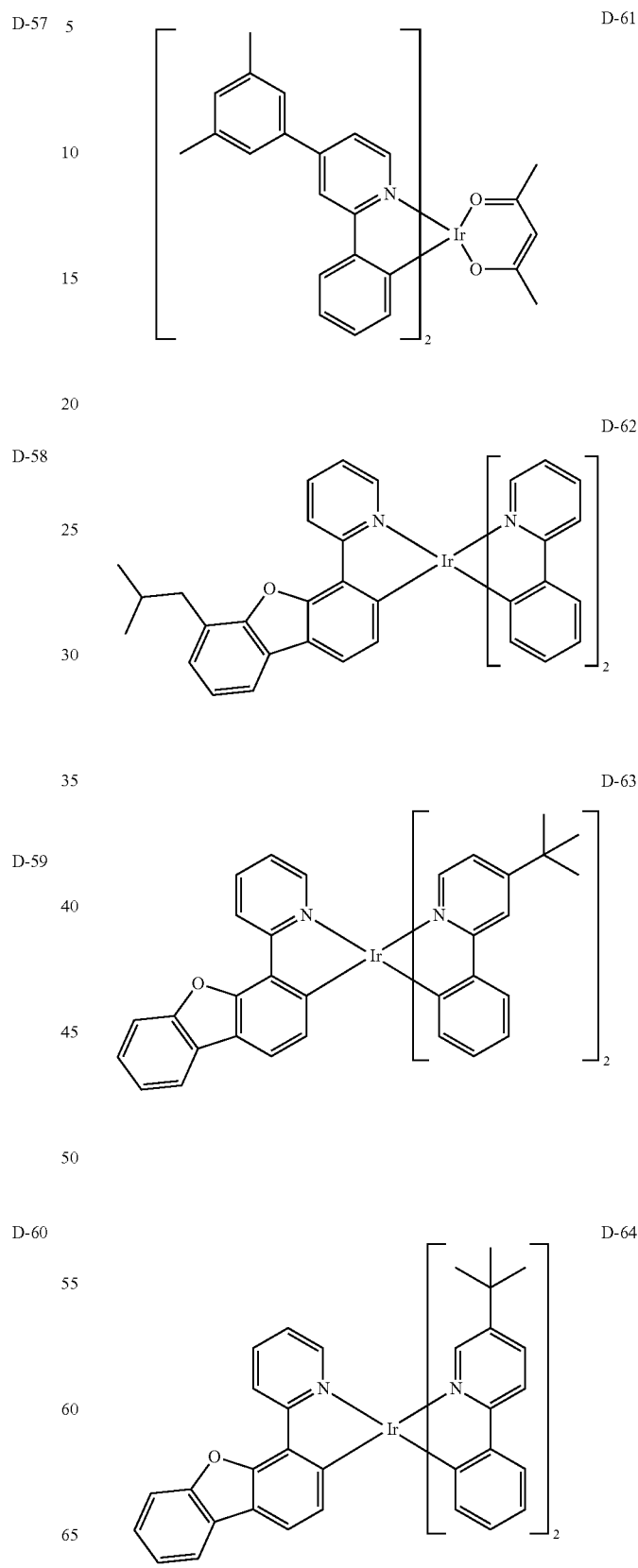

D-65
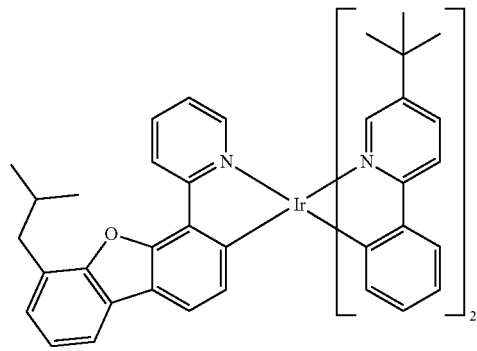
D-66
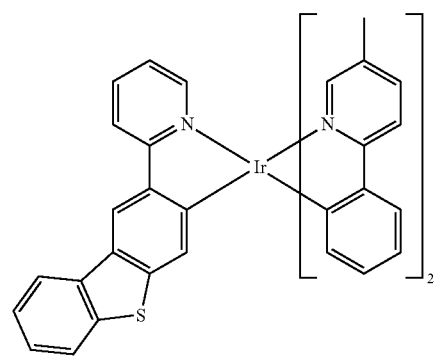
D-67
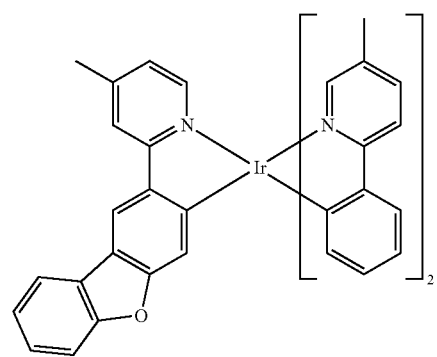
D-68
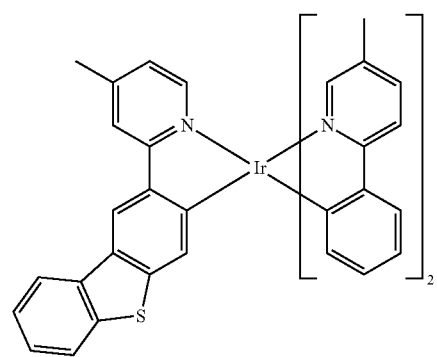
D-69
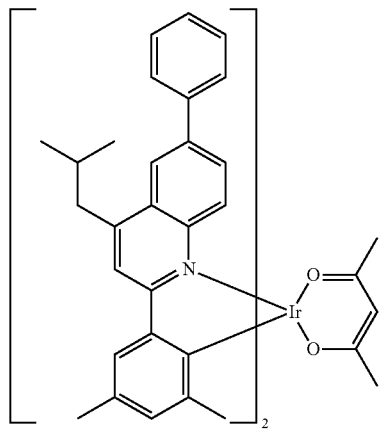
D-70
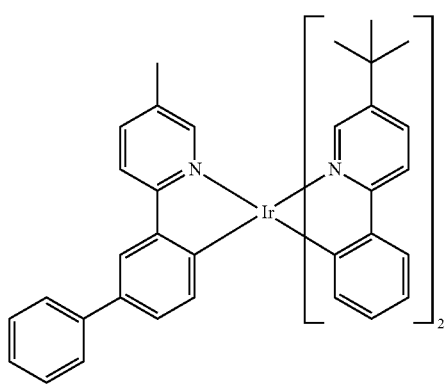
D-71
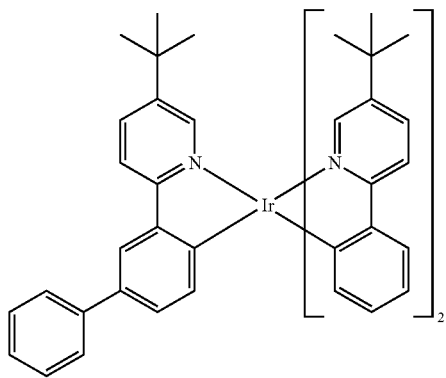
D-72
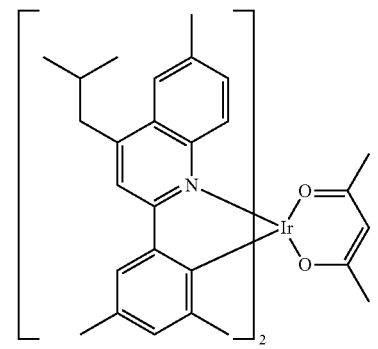

D-73
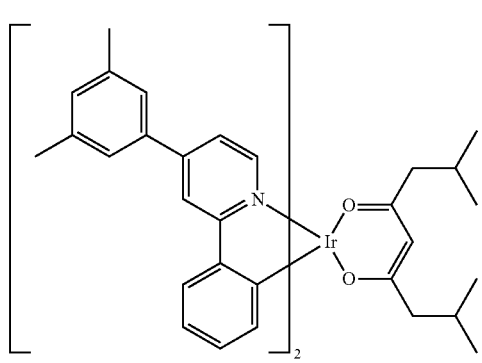
D-75
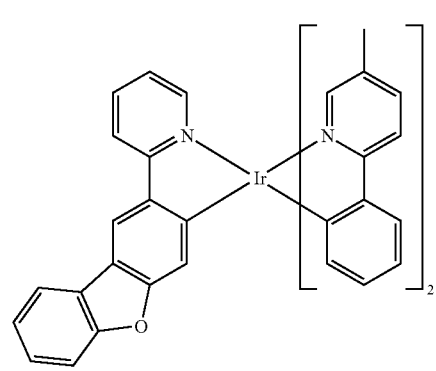
D-76
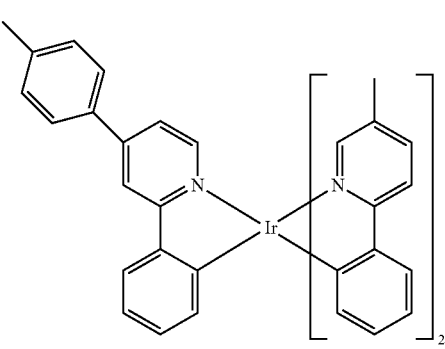
D-77
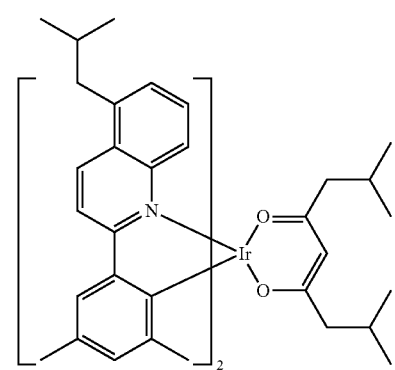
D-78
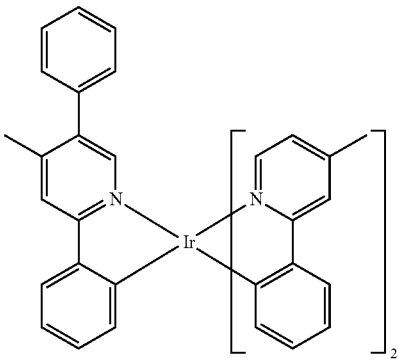
D-79
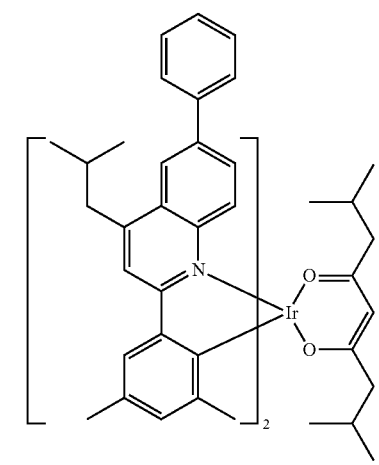
D-80
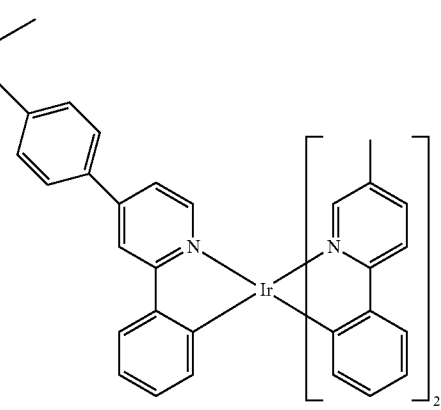
D-81
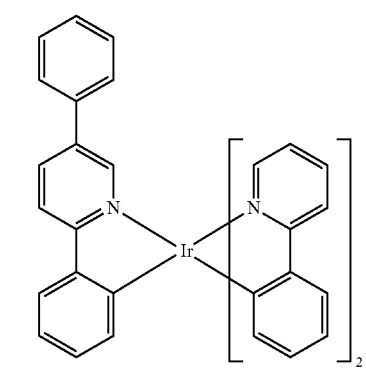

D-82
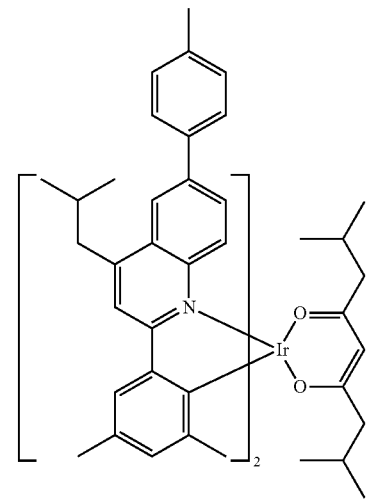
D-83
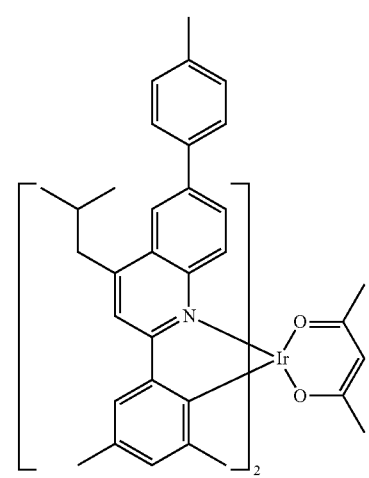
D-84
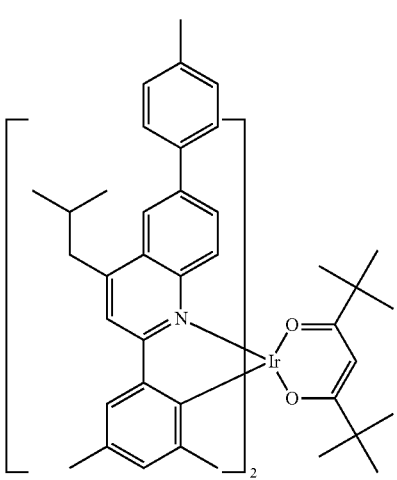
D-85
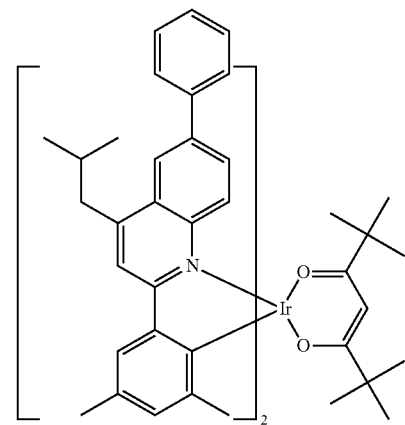
D-86
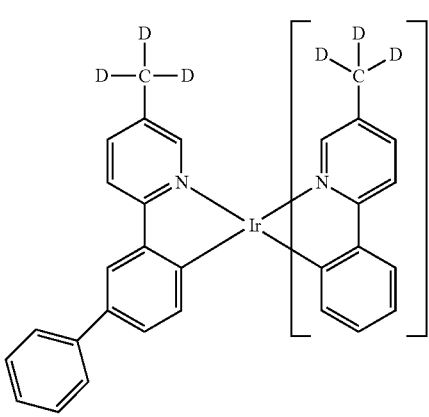
D-87
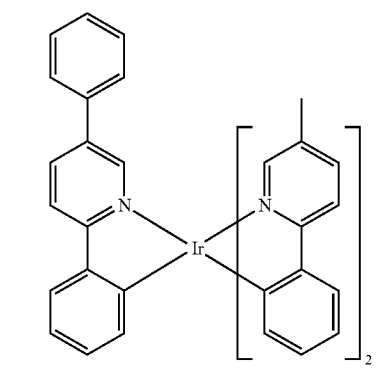
D-88
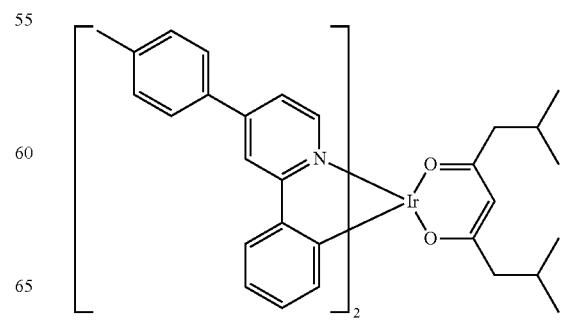

-continued
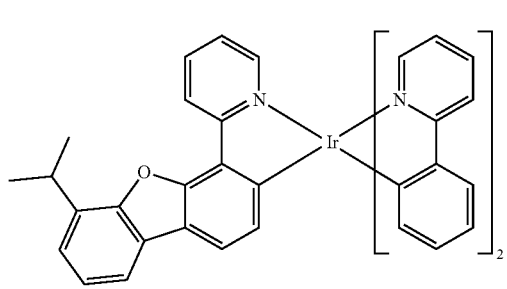
D-89
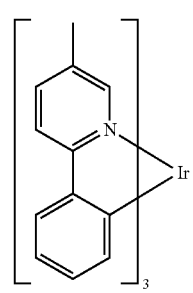
D-90
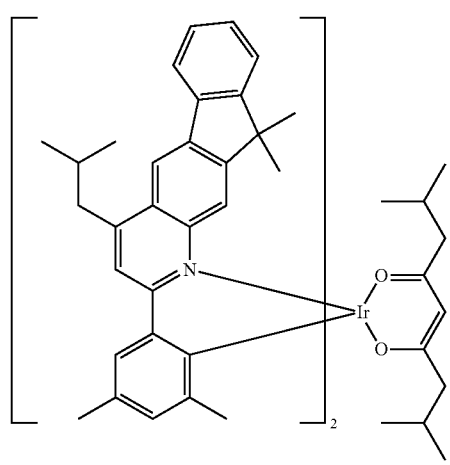
D-91
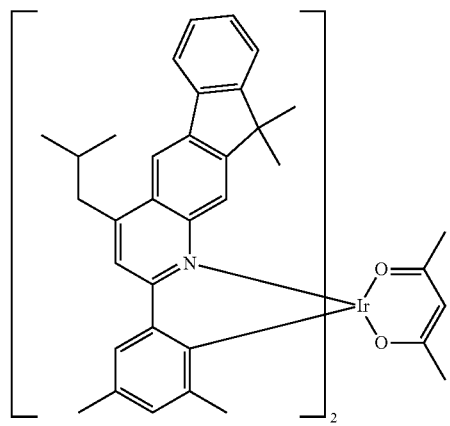
D-92
-continued
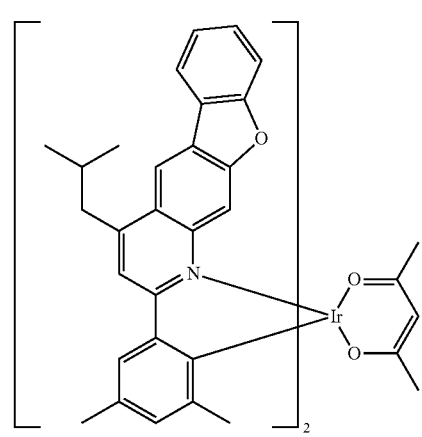
D-93
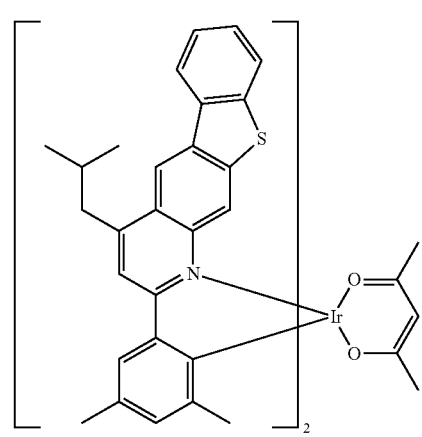
D-94
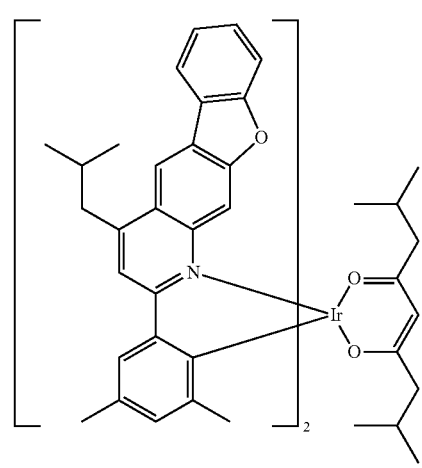
D-95

D-96
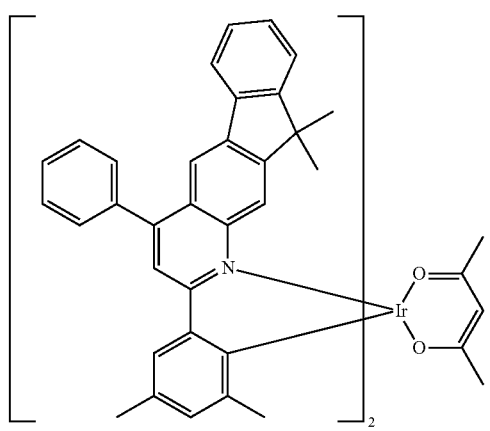
D-97
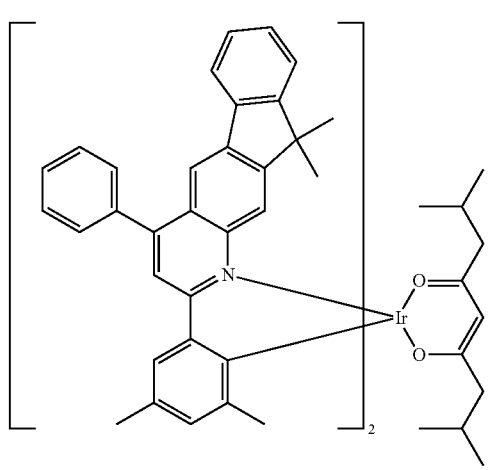
D-98
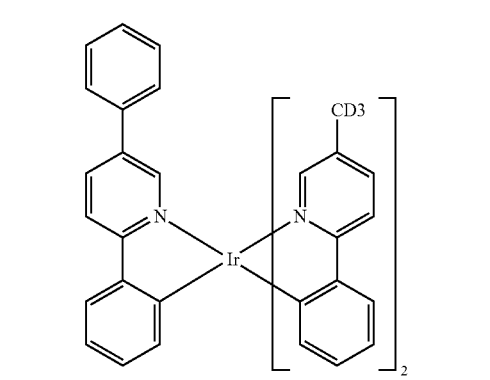
D-99
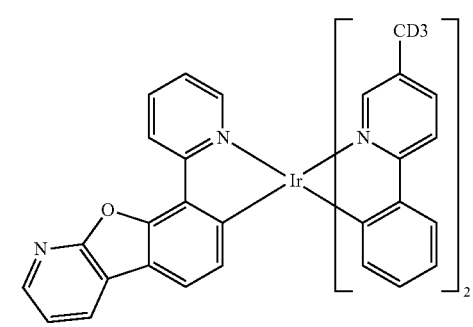
D-100
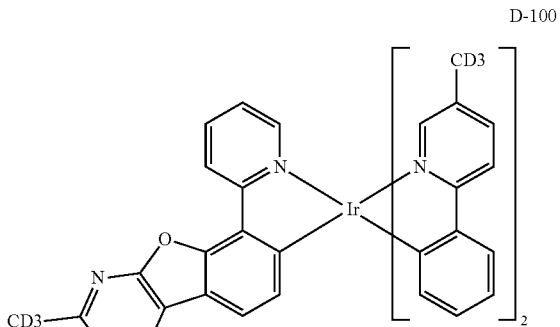
D-101
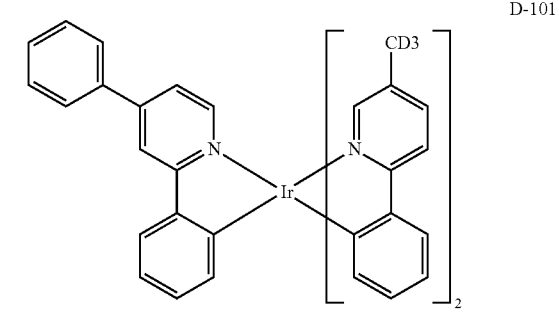
D-102
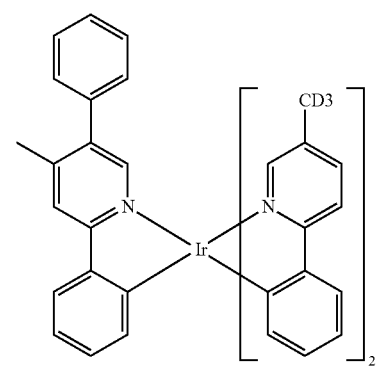
D-103
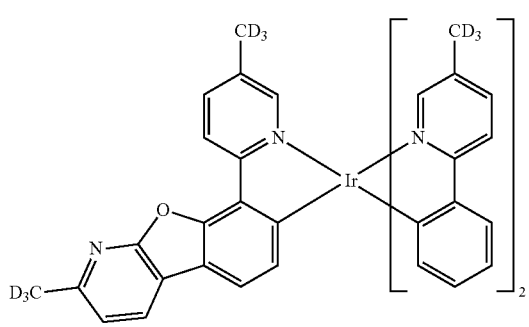

D-104
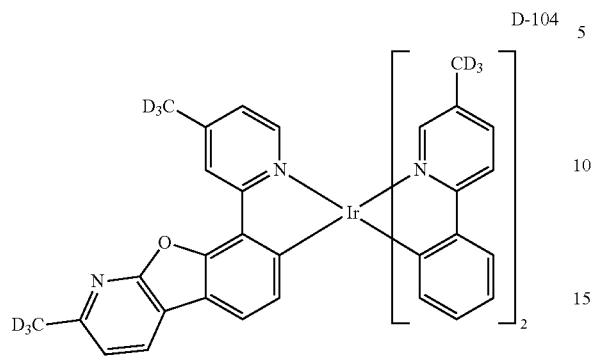
D-108
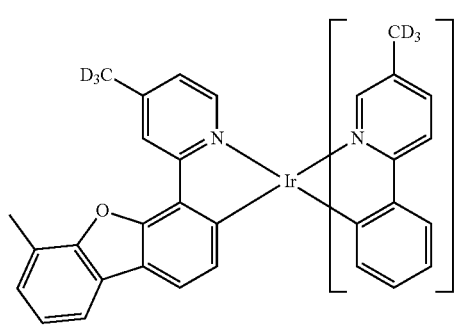
D-105
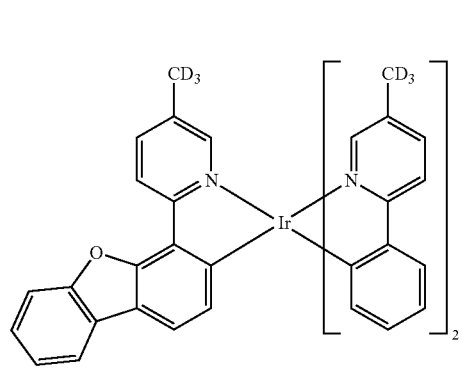
D-109
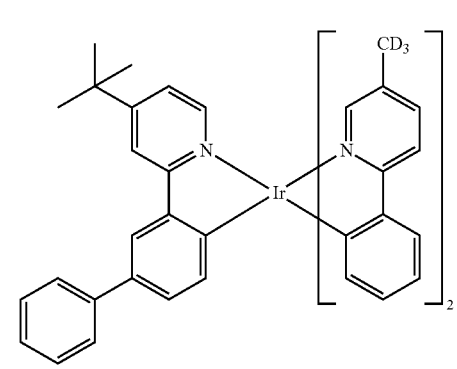
D-106
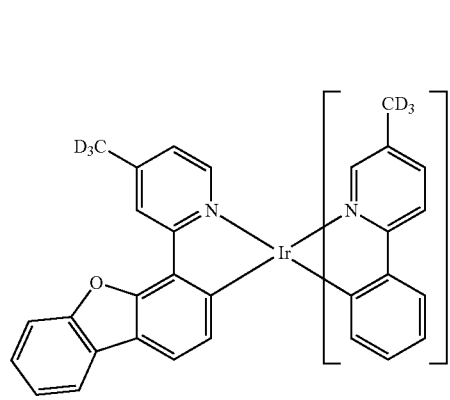
D-110
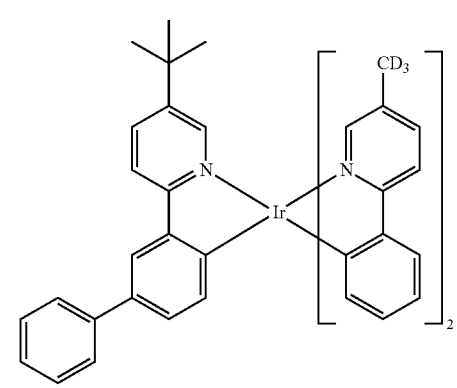
D-107
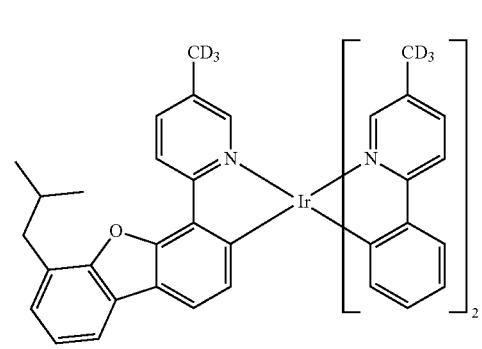
D-111
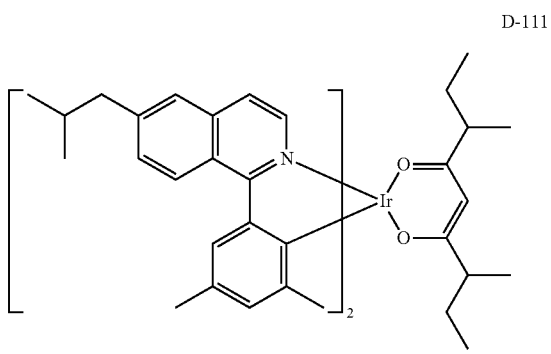

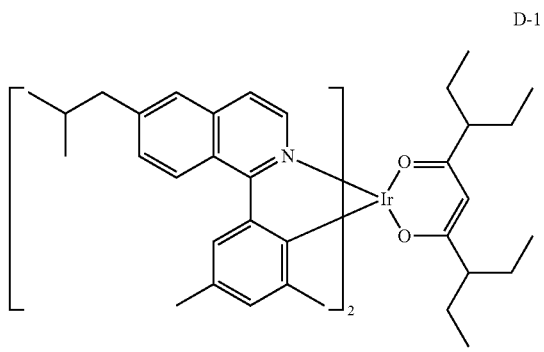

D-112

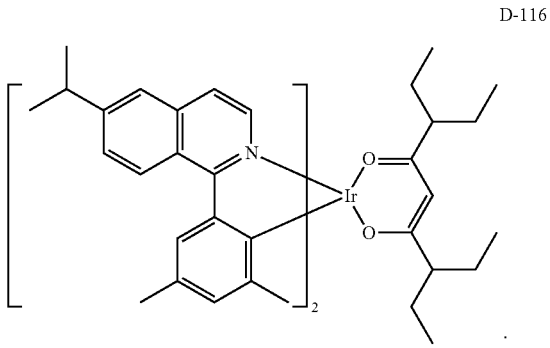

D-116

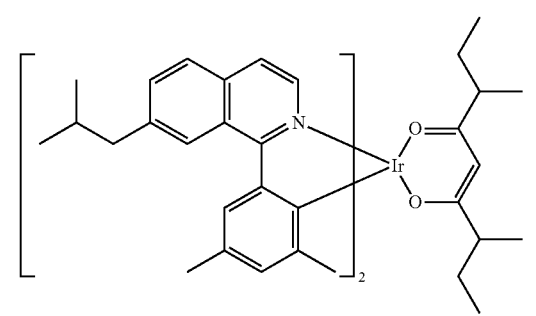

D-113

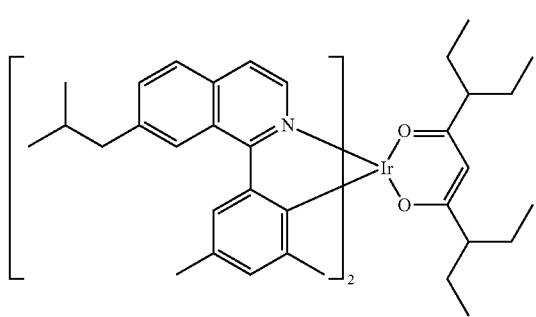

D-114

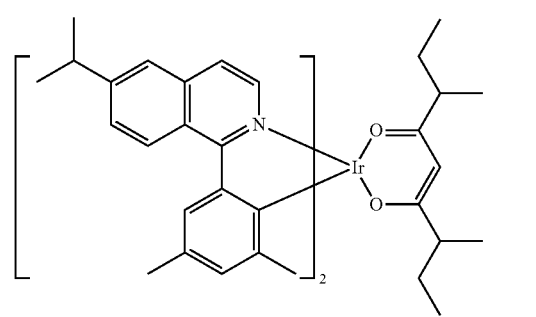

D-115

The organic electroluminescent device of the present disclosure may further comprise at least one compound selected from the group consisting of arylamine-based compounds and styrylarylamine-based compounds in the organic layer.

In addition, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

In the organic electroluminescent device of the present disclosure, at least one layer (hereinafter, "a surface layer") selected from a chalcogenide layer, a metal halide layer and a metal oxide layer may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer may provide operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; said metal halide includes LiF, $MgF_2$, $CaF_2$, a rare earth metal fluoride, etc.; and said metal oxide includes $Cs_2O$, $Li_2O$, MgO, SrO, BaO, CaO, etc.

Between the anode and the light-emitting layer, a layer selected from a hole injection layer, a hole transport layer, or an electron blocking layer, or a combination thereof may be used. The hole injection layer may be formed of multi-layers in order to lower the hole injection barrier (or hole injection voltage) from the anode to the hole transport layer or the electron blocking layer. Two compounds can be simultaneously used in each layer. The hole transport layer or the electron blocking layer may also be formed of multi-layers.

Between the light-emitting layer and the cathode, a layer selected from an electron buffer layer, a hole blocking layer, an electron transport layer, or an electron injection layer, or a combination thereof may be used. The electron buffer layer may be formed of multi-layers in order to control the injection of the electrons and enhance the interfacial characteristics between the light-emitting layer and the electron injection layer. Two compounds may be simultaneously used in each layer. The hole blocking layer or the electron transport layer may also be formed of multi-layers, and each layer can comprise two or more compounds.

In addition, in the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an organic electroluminescent device having two or more light-emitting layers and emitting white light.

In order to form each layer of the organic electroluminescent device of the present disclosure, dry film-forming methods such as vacuum evaporation, sputtering, plasma and ion plating, etc., or wet film-forming methods such as ink jet printing, nozzle printing, slot coating, spin coating, dip coating, and flow coating, etc., may be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Also, the first and second host compounds of the present disclosure may be co-evaporated or mixture-evaporated.

By using the organic electroluminescent device of the present disclosure, a display system or a lighting system can be produced.

Hereinafter, an organic electroluminescent compound according to the present disclosure, the preparation method thereof, and the luminescent characteristics of an organic electroluminescent device comprising the same will be explained in detail with reference to the representative compounds of the present disclosure in order to understand the present disclosure in detail.

Example 1: Preparation of Compound H1-1

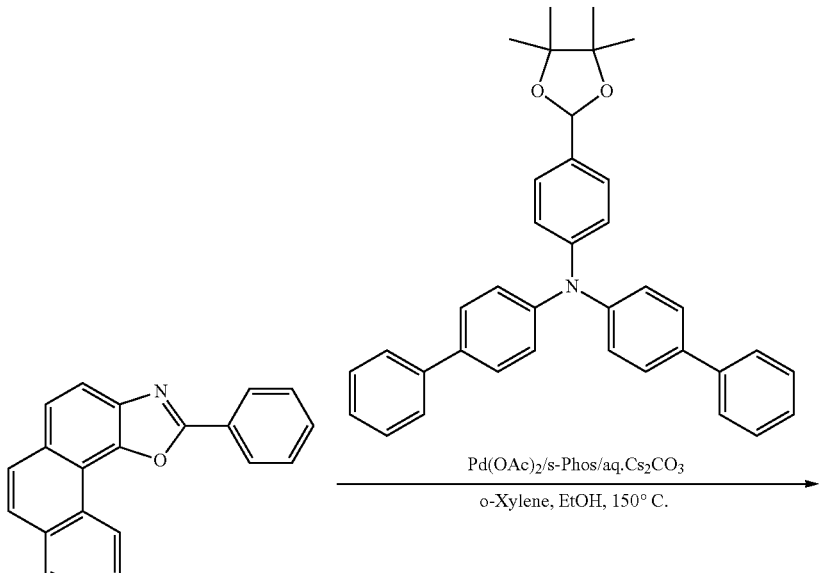

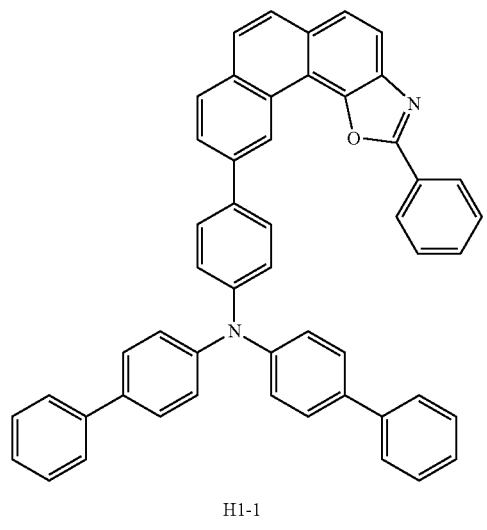

H1-1

Compound 1-1 (4 g, 12 mmol), bis(biphenyl-4-yl)[4-(4,4,5,5-tetramethyl-[1,3,2]-dioxaboran-2-yl)phenyl]amine (6.8 g, 13 mmol), palladium(II) acetate (0.3 g, 1 mmol), 2-dicyclohexylphosphino-2',6'-dimethoxybiphenyl (0.9 g, 2 mmol), cesium carbonate (11.5 g, 35 mmol), 60 mL of o-xylene, 15 mL of ethanol, and 15 mL of distilled water were added into a reaction vessel and refluxed for 3 hours. After completion of the reaction, the organic layer was washed with distilled water and extracted with ethyl acetate. The organic layer was then dried with magnesium sulfate. The solvent was removed with a rotary evaporator, and the resulting product was purified by column chromatography to obtain compound H1-1 (2.2 g, yield: 27%).

|   | MW | UV | PL | M.P |
|---|---|---|---|---|
| H1-1 | 690.85 | 406 nm | 427 nm | 271° C. |

Example 2: Preparation of Compound H1-42

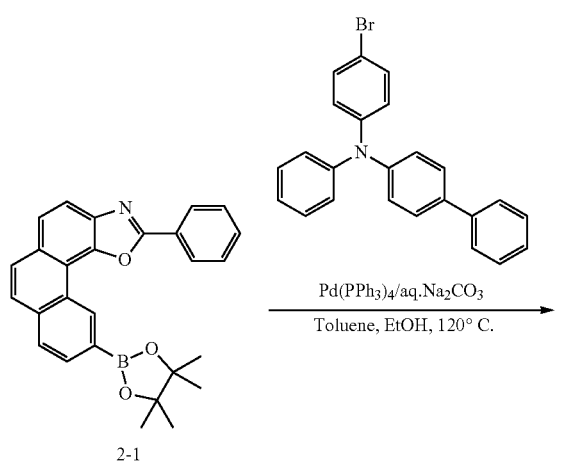

2-1

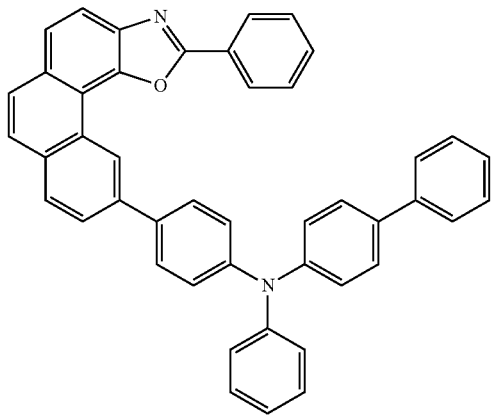

H1-42

Compound 2-1 (4.8 g, 11.34 mmol), N-(4-bromophenyl)-N-phenyl-[1,1'-biphenyl]-4-amine (5 g, 12.47 mmol), tetrakis(triphenylphosphine)palladium (0.4 g, 0.34 mmol), sodium carbonate (3.0 g, 28.35 mmol), 57 mL of toluene, 14 mL of ethanol, and 14 mL of distilled water were added into a reaction vessel and stirred at 120° C. for 4 hours. After completion of the reaction, methanol was added dropwise to the mixture, and the resulting solid was filtered. The resulting solid was purified to recrystallization by column chromatography to obtain the compound H1-42 (1.4 g, yield: 20.0%).

|   | MW | M.P |
|---|---|---|
| H1-42 | 614.73 | 230° C. |

Example 3: Preparation of Compound H1-27

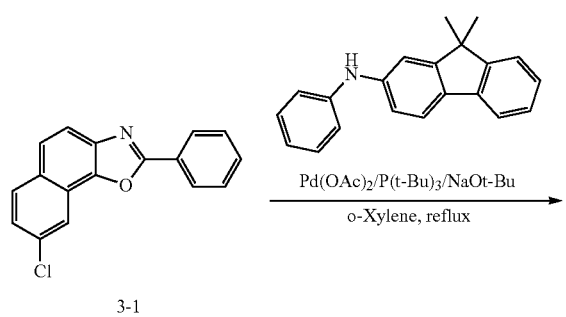

3-1

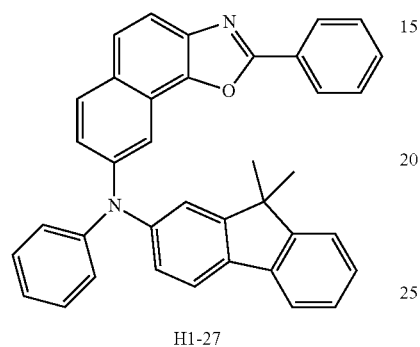

H1-27

Compound 3-1 (4.5 g, 16.09 mmol), 9,9-dimethyl-N-phenyl-9H-fluoren-2-amine (5.5 g, 19.31 mmol), palladium (II) acetate (0.2 g, 0.80 mmol), tri-t-butylphosphine (0.8 mL, 1.60 mmol), sodium tert-butoxide (2.3 g, 24.14 mmol), and 80 mL of o-xylene were added into a reaction vessel and refluxed at 120° C. for 2 hours. After completion of the reaction, the mixture was cooled to room temperature, and the resulting solid was filtered and washed with ethyl acetate. The filtrate was distilled under reduced pressure, and the resulting solid was purified to recrystallization by column chromatography to obtain the compound H1-27 (2.4 g, yield: 28%).

|   | MW | M.P |
|---|---|---|
| H1-27 | 528.64 | 209° C. |

Example 4: Preparation of Compound H2-1

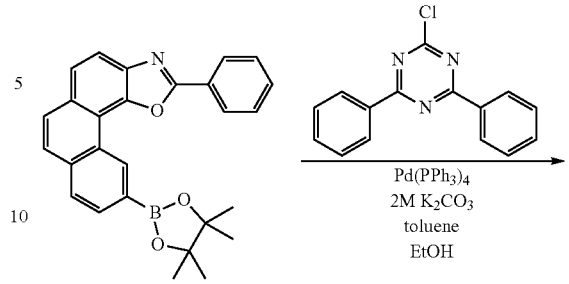

2-1

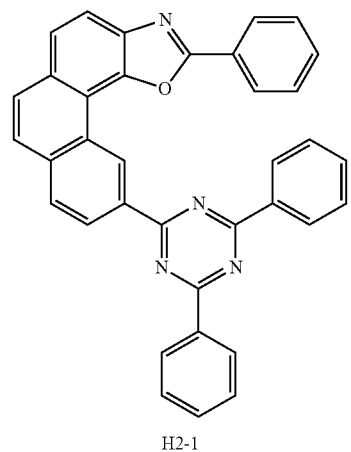

H2-1

Compound 2-1 (10 g, 23.7 mmol), 2-chloro-4,6-diphenyltriazine (CAS: 3842-55-5, 5.8 g, 21.6 mmol), tetrakis(triphenylphosphine)palladium (1.2 g, 1.0 mmol), potassium carbonate (7.5 g, 59 mmol), 90 mL of toluene, 30 mL of ethanol, and 30 mL of distilled water were added into a reaction vessel and stirred at 120° C. for 4 hours. After completion of the reaction, methanol was added dropwise to the mixture, and the resulting solid was filtered. The resulting solid was purified to recrystallization by column chromatography to obtain the compound H2-1 (5.7 g, yield: 50%).

|   | MW | UV | PL | M.P |
|---|---|---|---|---|
| H2-1 | 526.18 | 290 nm | 427 nm | 291° C. |

Example 5: Preparation of Compound H2-2

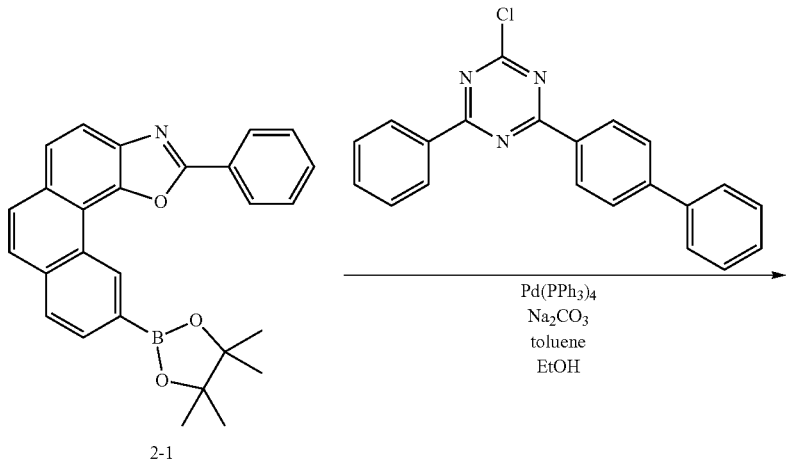

2-1

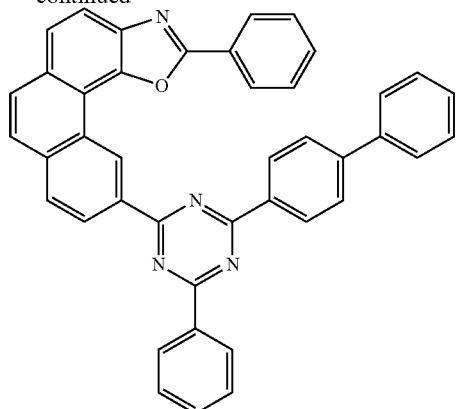

H2-2

Compound 2-1 (3.48 g, 8.3 mmol), 2-([1,1'-biphenyl]-4-yl)-4-chloro-6-phenyl-1,3,5-triazine (CAS: 1472062-94-4, 3.53 g, 9.1 mmol), tetrakis(triphenyl phosphine)palladium (0.48 g, 0.41 mmol), sodium carbonate (2.2 g, 20.7 mmol), 28 mL of toluene, 7 mL of ethanol, and 7 mL of distilled water were added into a reaction vessel and stirred at 120° C. for 5 hours. After completion of the reaction, methanol was added dropwise to the mixture, and the resulting solid was filtered. The resulting solid was purified to recrystallization by column chromatography to obtain the compound H2-2 (3.7 g, yield: 74%).

|      | MW     | UV     | PL     | M.P    |
|------|--------|--------|--------|--------|
| H2-2 | 602.21 | 324 nm | 429 nm | 299° C.|

LUMO (Lowest Unoccupied Molecular Orbital) energy, HOMO (Highest Occupied Molecular Orbital) energy, and triplet energy of the compounds H1-1 and H1-27 synthesized in Examples 1 and 3 above were calculated using Density Functional Theory (DFT) at B3LYP/6-31 g(d) level, and are shown in the following Table 1.

Basically, LUMO and HOMO energy values measured as described above have negative values; however, for convenience, are expressed in absolute values. In addition, when comparing the degree of LUMO/HOMO energy values, it compares absolute values thereof.

TABLE 1

| Compound | Structure | Calculation value B3LYP/6-31g* | | |
|----------|-----------|-----------|-----------|-------------|
|          |           | LUMO (eV) | HOMO (eV) | Triplet (eV)|
| H1-1     | 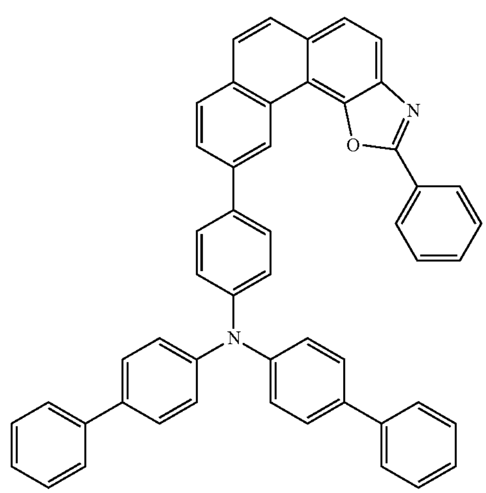 [SMILES: c1ccc(-c2ccc(N(c3ccc(-c4ccccc4)cc3)c3ccc(-c4ccc5ccc6ccc7nc(-c8ccccc8)oc7c6c5c4)cc3)cc2)cc1]          | 1.62      | 4.91      | 2.4         |

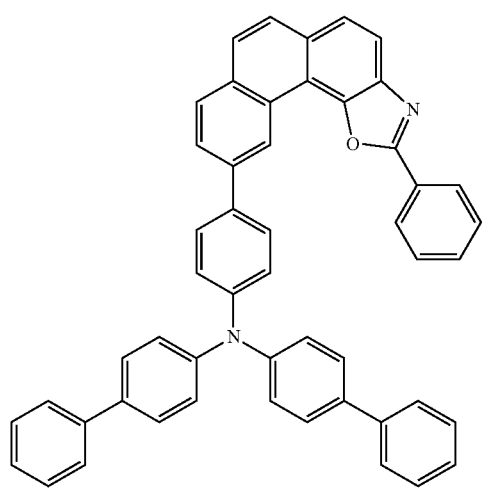

TABLE 1-continued

| Compound | Structure | Calculation value B3LYP/6-31g* | | |
|---|---|---|---|---|
| | | LUMO (eV) | HOMO (eV) | Triplet (eV) |
| H1-27 | 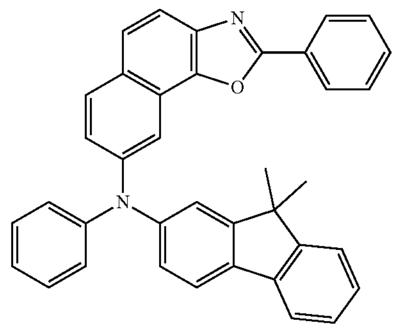 [SMILES: CC1(C)c2ccccc2-c2ccc(N(c3ccccc3)c3ccc4ccc5nc(-c6ccccc6)oc5c4c3)cc21] | 1.37 | 4.90 | 2.5 |

Referring to Table 1 above, the device characteristics of the first host compound according to one embodiment, i.e., compound H1-1 represented by formula 1, and compound H1-27 represented by formula 2, can be compared and predicted. Specifically, compound H1-27 has a similar HOMO energy value to compound H1-1, and has a lower LUMO energy value than compound H1-1. Thus, it is predicted that the electron carrier is sufficiently confined when compound H1-27 is used. In addition, when host compounds H1-1 and H1-27 are combined with a host having a strong electron current characteristic, it can be confirmed that the energy value thereof has no problem in exciplex formation. Further, triplet energy values of compounds H1-1 and H1-27 are 2.4 eV, and 2.5 eV, respectively, which are sufficient to block triplet energy of a dopant. That is, when using compound H1-1 or H1-27 as the first host compound according to one embodiment, it can be predicted that the device including one of them will exhibit similar device characteristics to the device including the other.

Thus, in the following Device Example, an organic electroluminescent device is produced by using only compounds H1-1 and H1-42 represented by formula 1 as the representative first host compound, and the characteristics of device thereof will be described.

Comparative Example 1: Producing a Red Light-Emitting Organic Electroluminescent Device not According to the Present Disclosure An OLED device not according to the present disclosure was produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropanol. Next, the ITO substrate was mounted on a substrate holder of a vacuum vapor deposition apparatus. Compound HI-1 was introduced into a cell of the vacuum vapor deposition apparatus, and the pressure in the chamber of the apparatus was then controlled to 10-torr. Thereafter, an electric current was applied to the cell to evaporate the introduced material, thereby forming a first hole injection layer having a thickness of 80 nm on the ITO substrate. Compound HI-2 was then introduced into another cell of the vacuum vapor deposition apparatus, and an electric current was applied to the cell to evaporate the introduced material, thereby forming a second hole injection layer having a thickness of 5 nm on the first hole injection layer. Next, compound HT-1 was introduced into another cell of the vacuum vapor deposition apparatus. Thereafter, an electric current was applied to the cell to evaporate the introduced material, thereby forming a first hole transport layer having a thickness of 10 nm on the second hole injection layer. Compound HT-2 was then introduced into another cell of the vacuum vapor deposition apparatus, and an electric current was applied to the cell to evaporate the introduced material, thereby forming a second hole transport layer having a thickness of 60 nm on the first hole transport layer. After forming the hole injection layers and the hole transport layers, a light-emitting layer was then deposited as follows. Compound H1-1 as a host was introduced into one cell of the vacuum vapor deposition apparatus and compound D-39 as a dopant was introduced into another cell of the apparatus. The two materials were evaporated at a different rate and the dopant was deposited in a doping amount of 3 wt %, based on the total weight of the host and dopant, to form a light-emitting layer having a thickness of 40 nm on the second hole transport layer. Next, compounds ETL-1 and EIL-1 as an electron transport material in a weight ratio of 50:50 were deposited on the light-emitting layer, to form an electron transport layer having a thickness of 35 nm. Next, compound EIL-1 as an electron injection layer having a thickness of 2 nm was deposited on the electron transport layer, and an Al cathode having a thickness of 80 nm was deposited on the electron injection layer by another vacuum vapor deposition apparatus. Thus, an OLED device was produced. All the materials used for producing the OLED device were purified by vacuum sublimation at $10^{-6}$ torr.

Comparative Example 2: Producing a Red Light-Emitting Organic Electroluminescent Device not According to the Present Disclosure An OLED device was produced in the same manner as in Comparative Example 1, except that compound H2-2 instead of H1-1 as a light-emitting material was used.

Comparative Example 3: Producing a Red Light-Emitting Organic Electroluminescent Device not According to the Present Disclosure An OLED device was produced in the same manner as in Comparative Example 1, except that compound H2-1 instead of H1-1 as a light-emitting material was used.

Device Examples 1 to 3: Producing a Red Light-Emitting Organic Electroluminescent Device According to the Present Disclosure In Device Examples 1 to 3, OLED device were produced in the same manner as in Comparative Example 1, except that each of a first host compound and a second host compound described in the following Table 2 as a host were introduced into one cell of the vacuum vapor deposition apparatus, and compound D-39 as a dopant was introduced into another cell of the apparatus. The two host materials were evaporated at the same rate of 1:1 and at the same time, the dopant was evaporated at a different rate in a doping amount of 3 wt %, based on the total weight of the host and dopant, to form a light-emitting layer having a thickness of 40 nm.

The driving voltage, the luminous efficiency, and the CIE color coordinates at a luminance of 1,000 nits and the time taken for the light-emission to be reduced from 100% to 90% at a luminance of 5,000 nit (lifespan; T90) of the organic electroluminescent device of Comparative Examples 1 to 3 and Device Examples 1 to 3 produced as above are shown in the following Table 2. In addition, the current efficiency according to the luminance of the organic electroluminescent device produced in Comparative Example 2 and Device Example 1 is shown in FIGURE.

TABLE 2

| | First Host | Second Host | Driving Voltage (V) | Luminous Efficiency (cd/A) | Color Coordinate x | Color Coordinate y | Lifespan (T90, hr) |
|---|---|---|---|---|---|---|---|
| Comparative Example 1 | H1-1 | — | 4.5 | 9.3 | 0.659 | 0.336 | 28.5 |
| Comparative Example 2 | — | H2-2 | 3.1 | 23.4 | 0.670 | 0.330 | 122.0 |
| Comparative Example 3 | — | H2-1 | 3.1 | 24.5 | 0.669 | 0.330 | 99.3 |
| Device Example 1 | H1-1 | H2-2 | 3.2 | 26.6 | 0.671 | 0.329 | 601.1 |
| Device Example 2 | H1-1 | H2-1 | 3.3 | 26.4 | 0.670 | 0.330 | 623.1 |
| Device Example 3 | H1-42 | H2-2 | 3.1 | 28.1 | 0.671 | 0.329 | 683 |

From Device Examples 1 to 3 above, it was confirmed that the combination of the compounds of the present disclosure can greatly improve the efficiency and lifespan characteristics while maintaining a driving voltage similar to that of the Comparative Example. Specifically, referring to FIGURE, the combination of light-emitting layer as the organic electroluminescent device according to one embodiment exhibits great effect on the roll-off improvement compared with the Comparative Example, which is the combination of the single light-emitting layer.

The compounds used in the Comparative Examples and Device Examples are shown in Table 3 below.

TABLE 3

| Hole Injection Layer/Hole Transport Layer | |
|---|---|

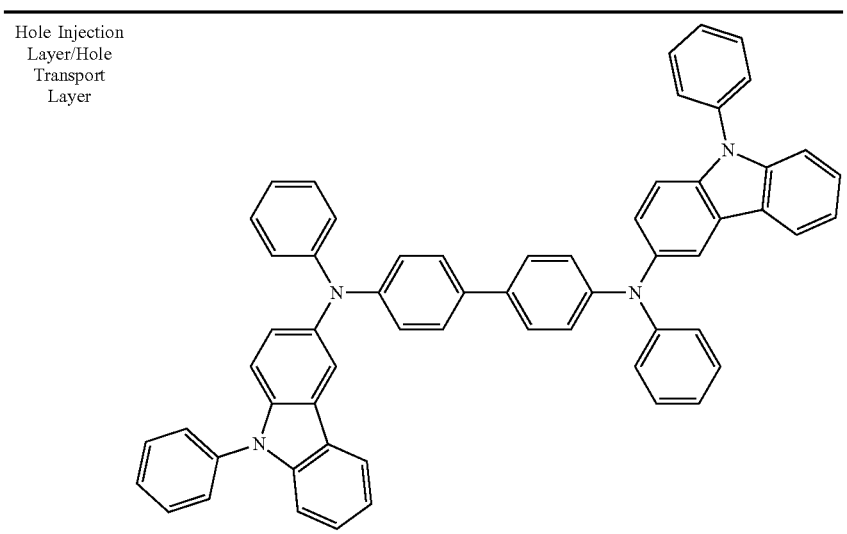

HI-1

TABLE 3-continued
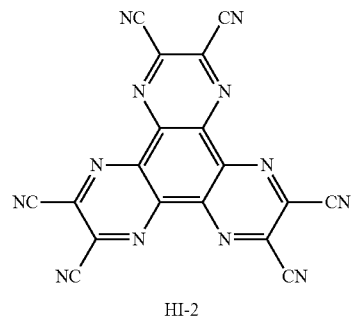 [SMILES: N#Cc1nc2c3nc(C#N)c(C#N)nc3c3nc(C#N)c(C#N)nc3c2nc1C#N]
HI-2
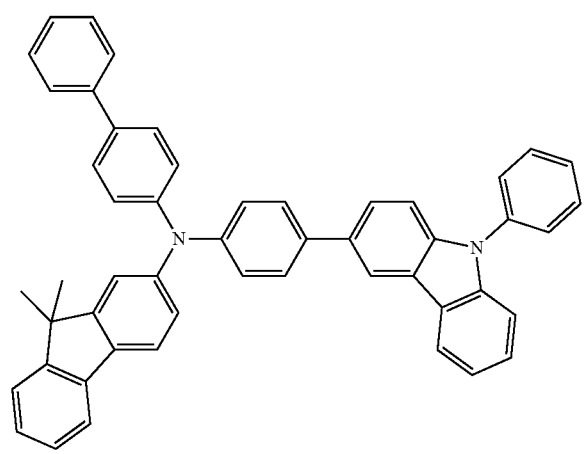
HT-1
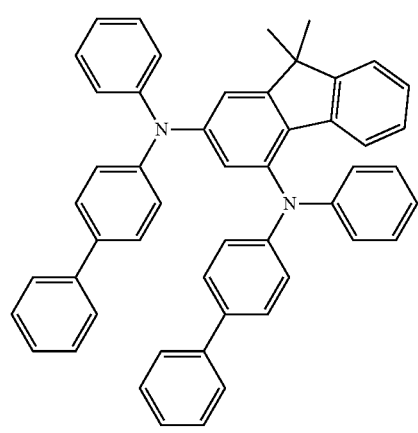
HT-2

TABLE 3-continued
Light-Emitting Layer
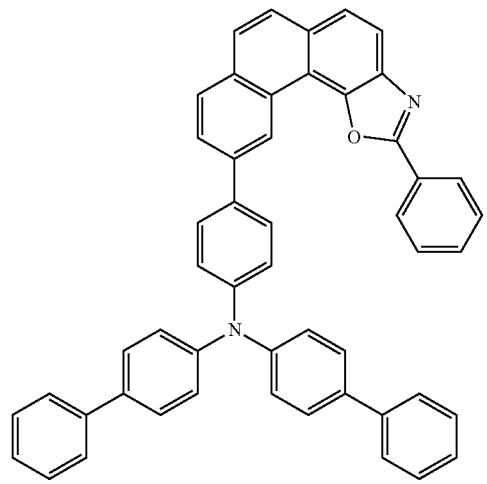
H1-1
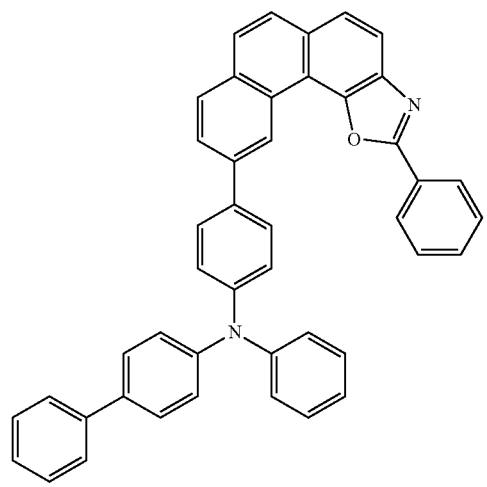
H1-42
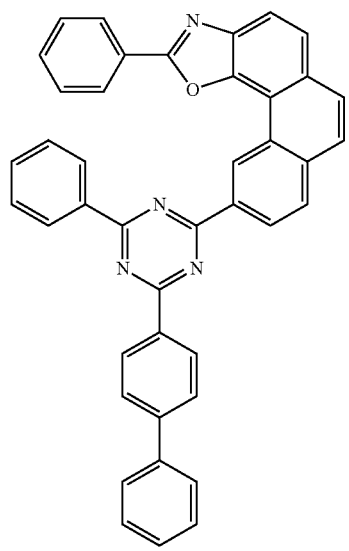
H2-2

TABLE 3-continued
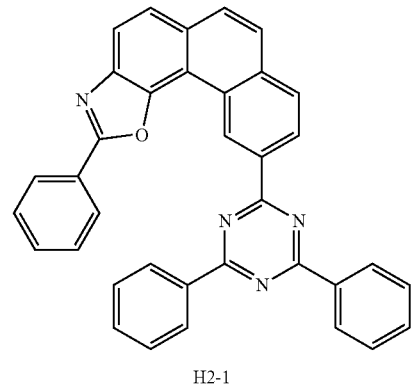 [SMILES: c1ccc(-c2nc(-c3ccccc3)nc(-c3ccc4ccc5ccc6nc(-c7ccccc7)oc6c5c4c3)n2)cc1]
H2-1
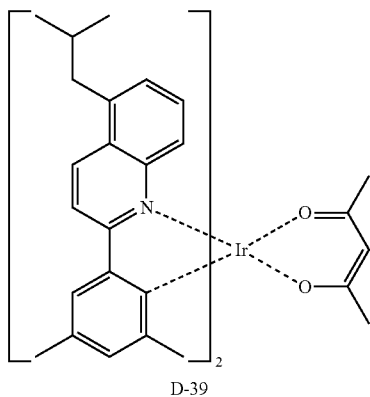
D-39
Electron
Transport
Layer/Electron
Injection
Layer
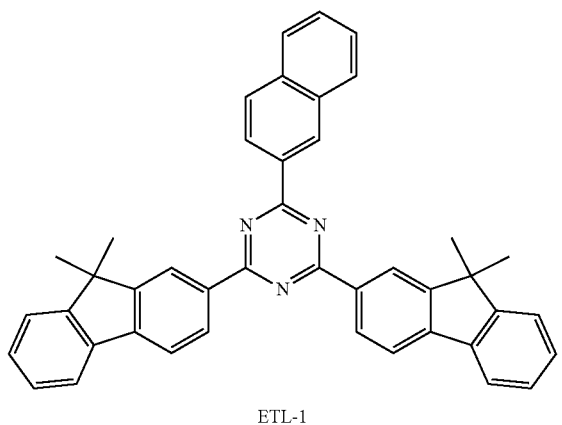 [SMILES: CC1(C)c2ccccc2-c2ccc(-c3nc(-c4ccc5c(c4)C(C)(C)c4ccccc4-5)nc(-c4ccc5ccccc5c4)n3)cc21]
ETL-1
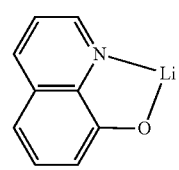
EIL-1

The invention claimed is:

1. A plurality of host materials comprising at least one of a first host compound and at least one of a second host compound, wherein the first host compound is represented by the following formula 2, and the second host compound is represented by the following formula 3:

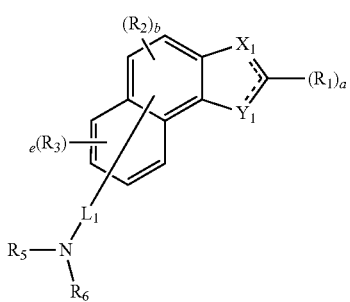

(2)

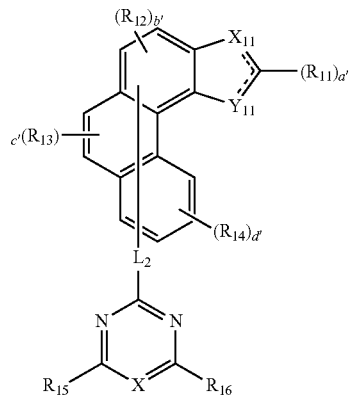

(3)

wherein, $X_1$ represents —N=, —NR$_7$—, —O— or —S—, $Y_1$ represents —N=, —NR$_8$—, —O— or —S—, provided that when $X_1$ represents —N=, $Y_1$ represents —NR$_8$—, —O— or —S—, and when $X_1$ represents —NR$_7$—, $Y_1$ represents —N=, —O— or —S—, $R_1$ represents a substituted or unsubstituted (C6-C30)aryl, or a substituted or unsubstituted (3- to 30-membered) heteroaryl, $R_2$, $R_3$ and $R_5$ to $R_8$ each independently represent hydrogen, deuterium, halogen, cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C6-C30)arylamino, or a substituted or unsubstituted (C1-C30)alkyl (C6-C30)arylamino, or may be linked to an adjacent substituent to form a substituted or unsubstituted, (C3-C30) mono- or polycyclic, alicyclic, or aromatic ring, whose carbon atom may be replaced with at least one heteroatom selected from nitrogen, oxygen, and sulfur, $L_1$ represents a single bond, a substituted or unsubstituted (C6-C30)arylene, or a substituted or unsubstituted (3- to 30-membered)heteroarylene, a represents 1, b represents 1 or 2, and e represents an integer of 1 to 4, the heteroaryl(ene) contains at least one heteroatom selected from B, N, O, S, Si, and P;

$X_{11}$ represents —N=, —NR$_{17}$—, —O— or —S—, $Y_{11}$ represents —N=, —NR$_{18}$—, —O— or —S—, provided that when $X_{11}$ represents —N=, $Y_{11}$ represents —NR$_{18}$—, —O— or —S—, and when $X_{11}$ represents —NR$_{17}$—, $Y_{11}$ represents —N=, —O— or —S—, X represents N, $R_{11}$ represents a substituted or unsubstituted (C6-C30) aryl, or a substituted or unsubstituted (3- to 30-membered)heteroaryl, $R_{12}$ to $R_{18}$ each independently represent hydrogen, deuterium, halogen, cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C6-C30)arylamino, or a substituted or unsubstituted (C1-C30)alkyl (C6-C30)arylamino, or may be linked to an adjacent substituent to form a substituted or unsubstituted, (C3-C30) mono- or polycyclic, alicyclic, or aromatic ring, whose carbon atom may be replaced with at least one heteroatom selected from nitrogen, oxygen, and sulfur, $L_2$ represents a single bond, a substituted or unsubstituted (C6-C30)arylene, or a substituted or unsubstituted (3- to 30-membered)heteroarylene, a' represents 1, b' and c' each independently represent 1 or 2, d' represents an integer of 1 to 4, the heteroaryl(ene) contains at least one heteroatom selected from B, N, O, S, Si, and P.

2. The host materials according to claim 1, wherein the formula 2 is represented by any one of the following formulae 1-4 to 1-5:

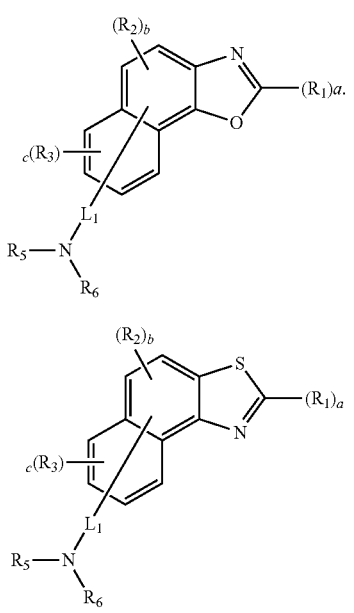
(1-4)
(1-5)
wherein,
R₁ to R₃, R₅ and R₆, L₁ and a, b, and e are as defined in claim 1.
3. The host materials according to claim 1, wherein the formula 3 is represented by any one of the following formulae 3-1 to 3-6:
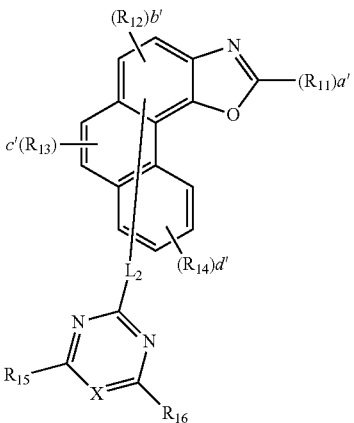
(3-1)
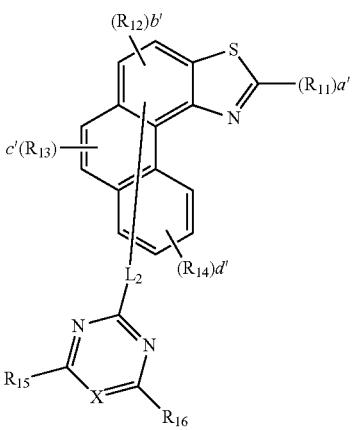
(3-2)
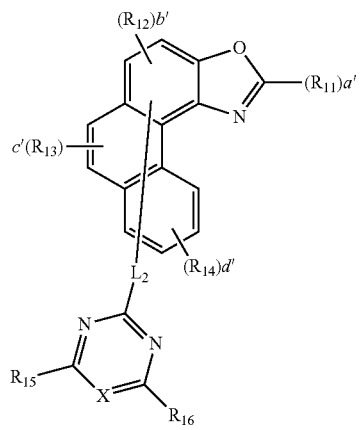
(3-3)
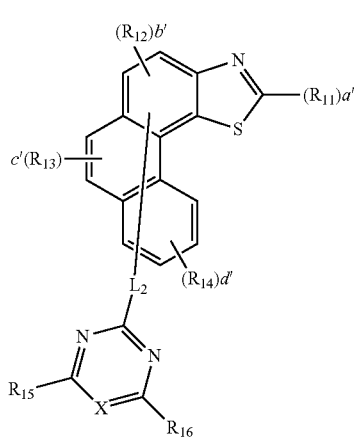
(3-4)
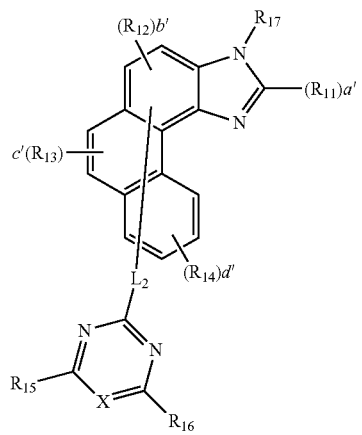
(3-5)

-continued

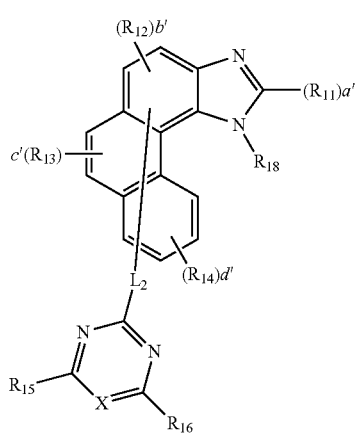

(3-6)

wherein, $R_{11}$ to $R_{18}$, $L_2$, X and a' to d' are as defined in claim 1.

4. The host materials according to claim 1, wherein the substituents of the substituted alkyl, the substituted alkoxy, the substituted cycloalkyl, the substituted aryl(ene), the substituted heteroaryl(ene), the substituted trialkylsilyl, the substituted triarylsilyl, the substituted dialkylarylsilyl, the substituted alkyldiarylsilyl, the substituted triarylsilyl, the substituted mono- or di- alkylamino, the substituted mono- or di- arylamino, the substituted alkylarylamino, and the substituted mono- or polycyclic, alicyclic, or aromatic ring, in $R_1$ to $R_3$, $R_5$ to $R_8$, $R_{11}$ to $R_{18}$, $L_1$ and $L_2$, are each independently at least one selected from the group consisting of deuterium; halogen; cyano; carboxyl; nitro; hydroxyl; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (3- to 7-membered)heterocycloalkyl; (C6-C30)aryloxy; (C6-C30)arylthio; (C6-C30)aryl- or di(C6-C30)arylamino-substituted or unsubstituted (3- to 30-membered)heteroaryl; cyano-, (3-to 30-membered)heteroaryl- or tri(C6-C30)arylsilyl-substituted or unsubstituted (C6-C30)aryl; tri(C1-C30)alkylsilyl; tri(C6-C30)arylsilyl; di(C1-C30)alkyl(C6-C30)arylsilyl; (C1-C30)alkyldi(C6-C30)arylsilyl; amino; a mono- or di- (C1-C30)alkylamino; a mono- or di- (C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl.

5. The host materials according to claim 1, wherein the compound represented by formula 2 is selected from the group consisting of:

H1-27

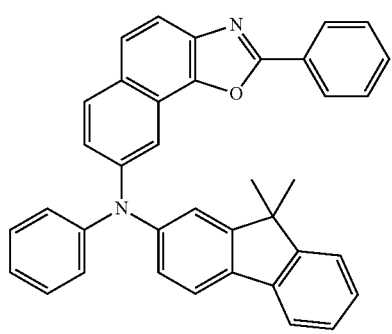

H1-28

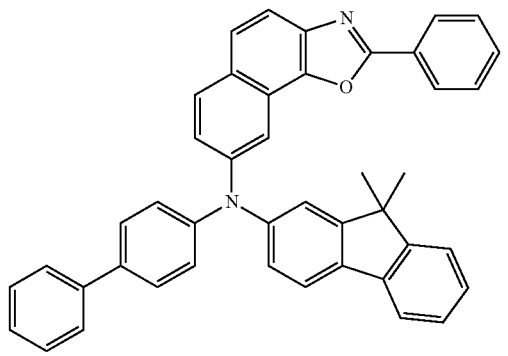

H1-29

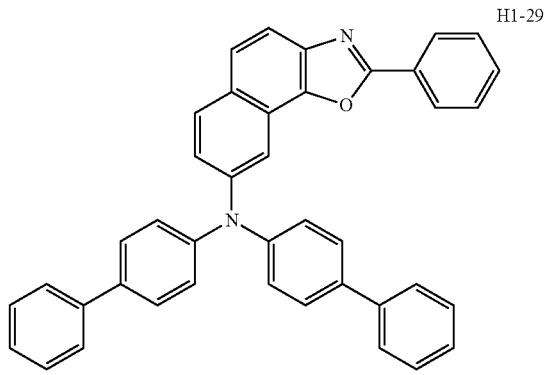

H1-30

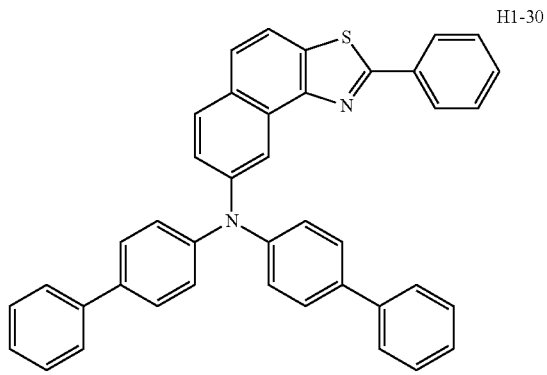

H1-31

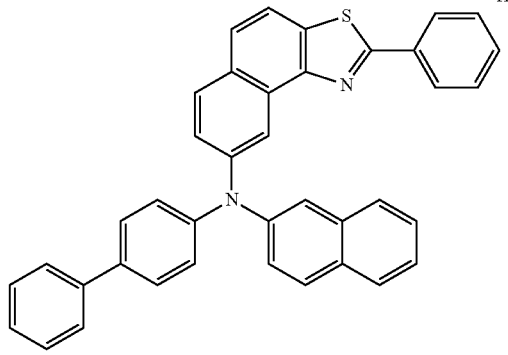

H1-32
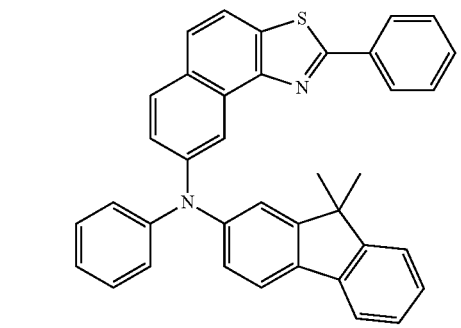
H1-33
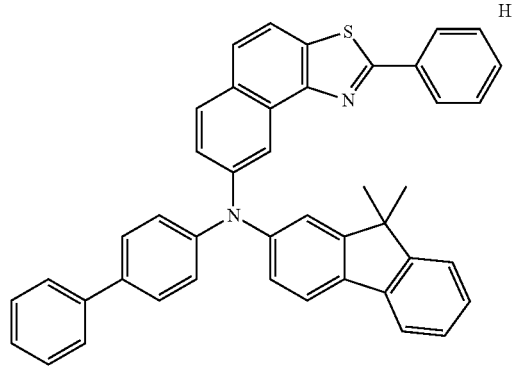
H1-34
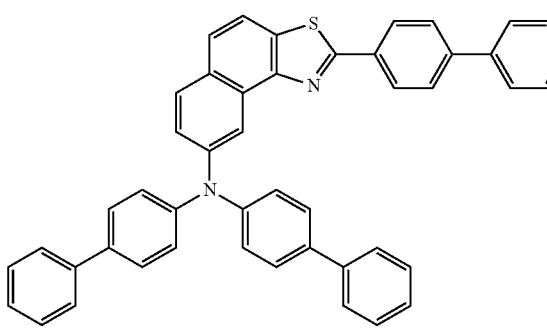
H1-35
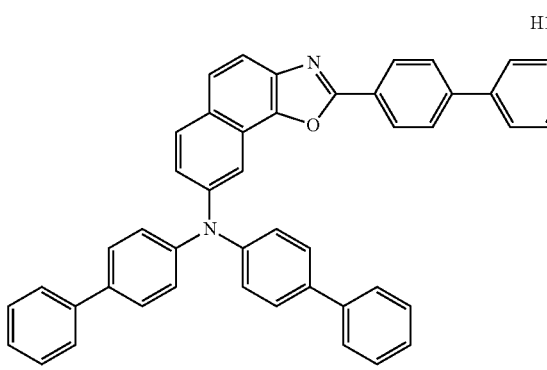
H1-36
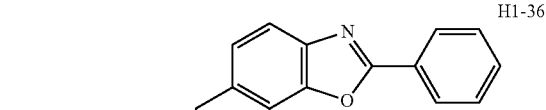
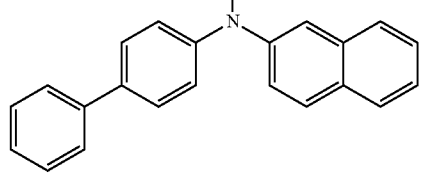
H1-37
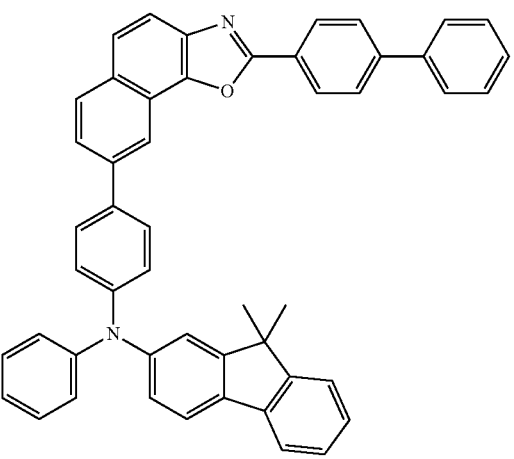
H1-38
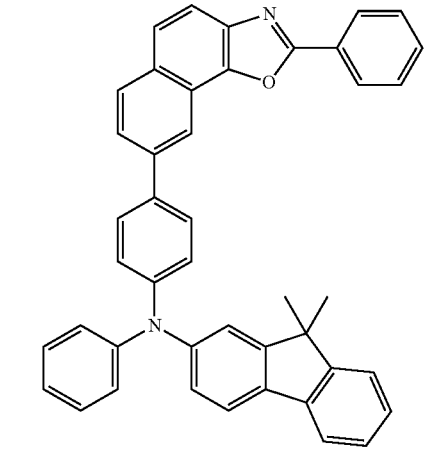
H1-39
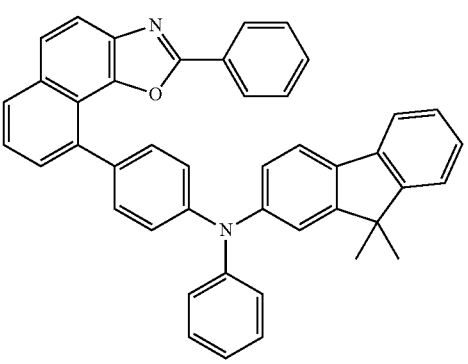

113
-continued
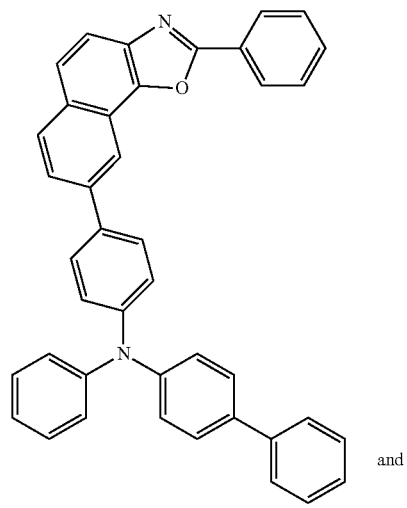
H1-40
and
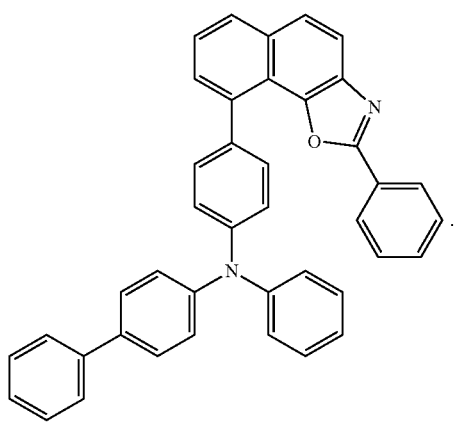
H1-41
114
-continued
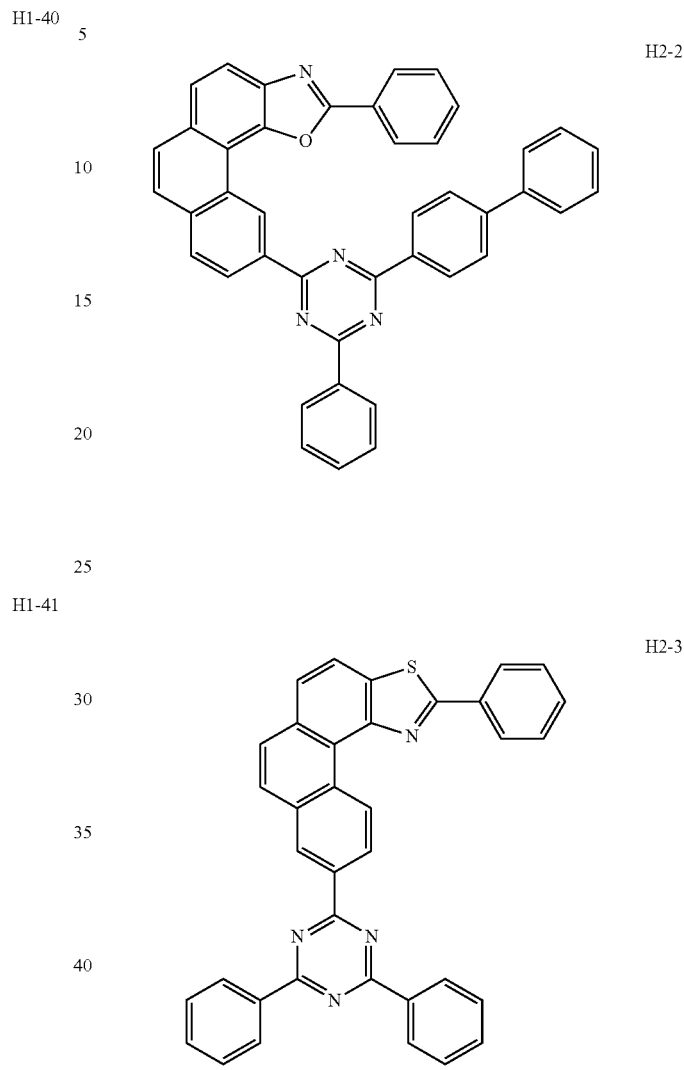
H2-2
H2-3
6. The host materials according to claim 1, wherein the compound represented by formula 3 is selected from the group consisting of:
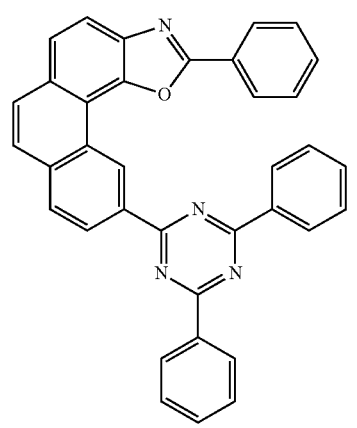
H2-1
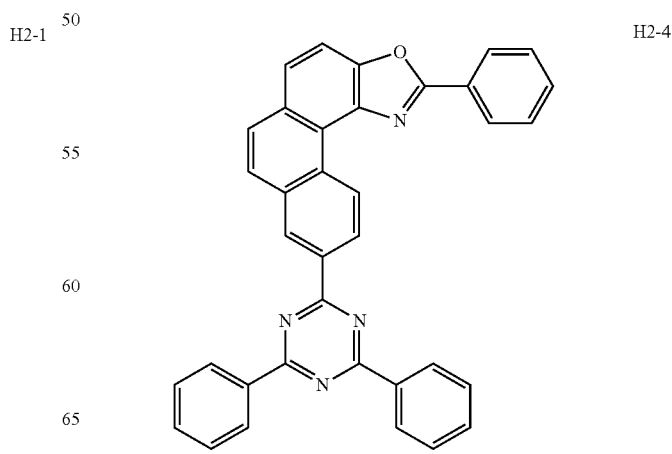
H2-4

115
-continued
116
-continued
H2-6
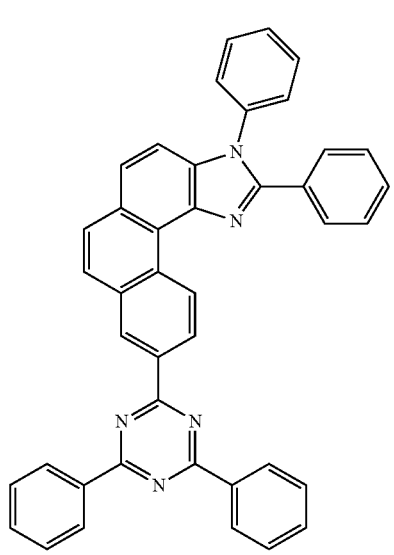
H2-7
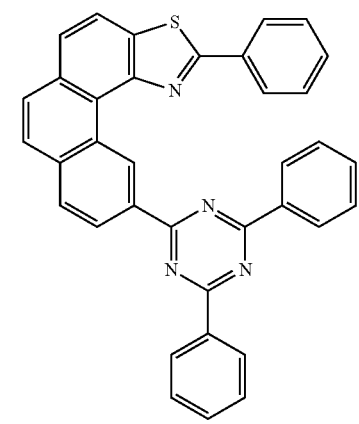
H2-8
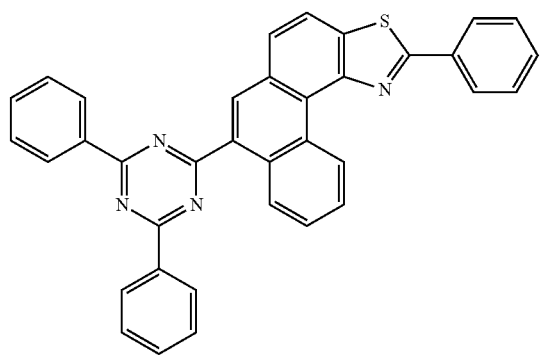
H2-9
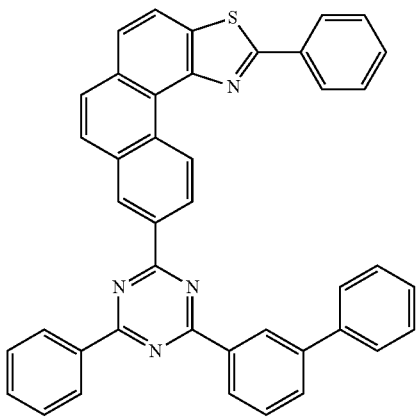
H2-10
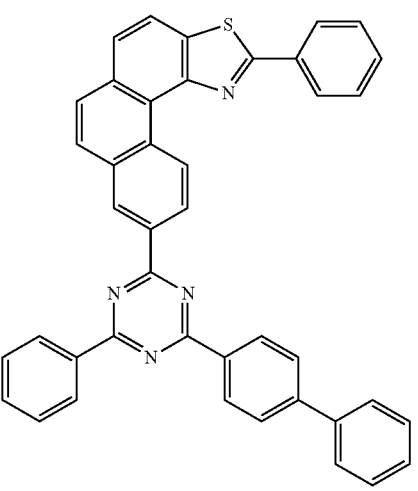
H2-11
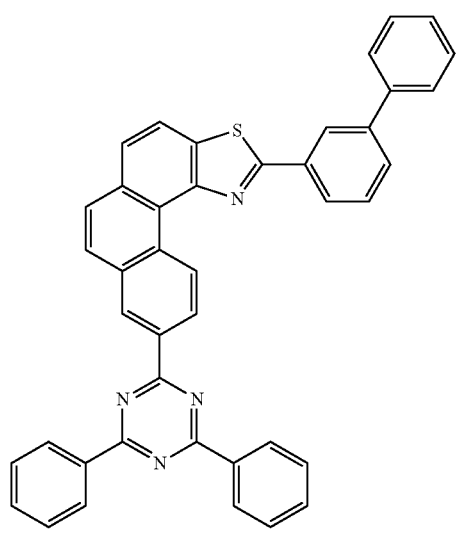

H2-12
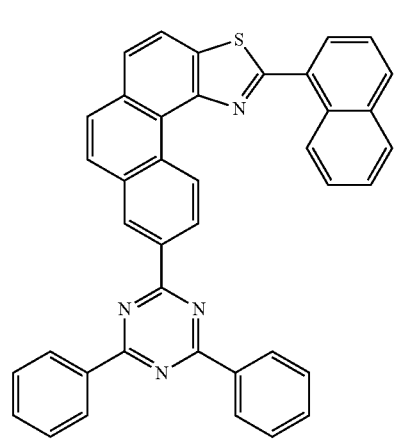
H2-13
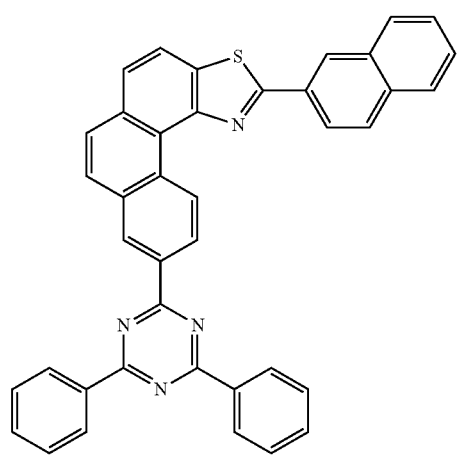
H2-14
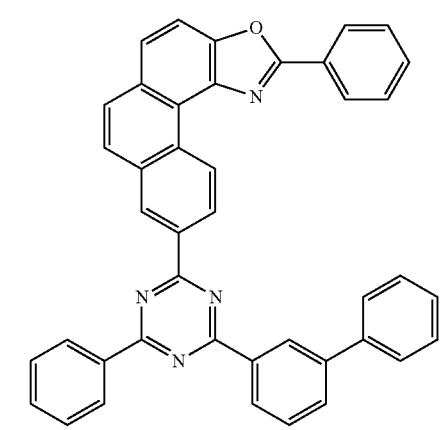
H2-17
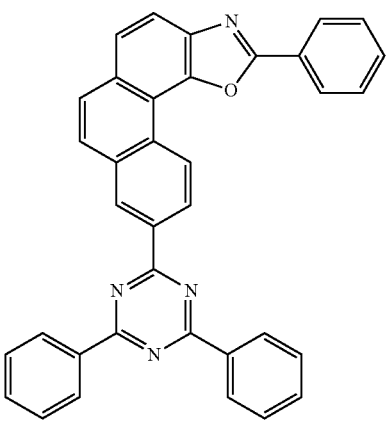
H2-19
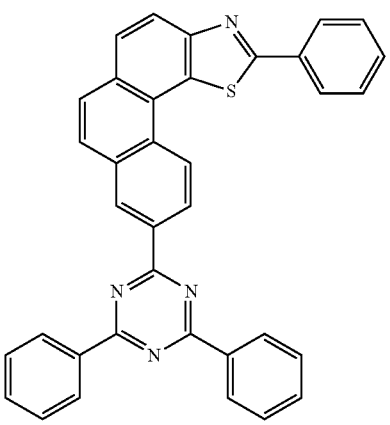
H2-20
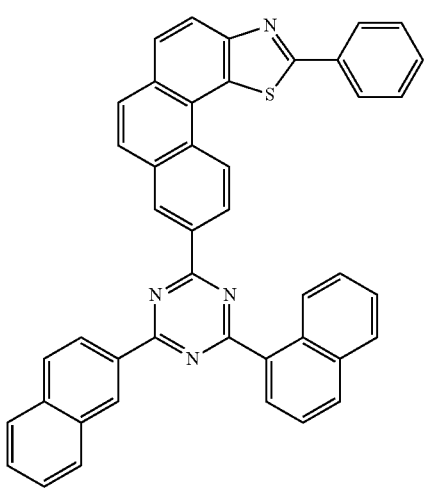

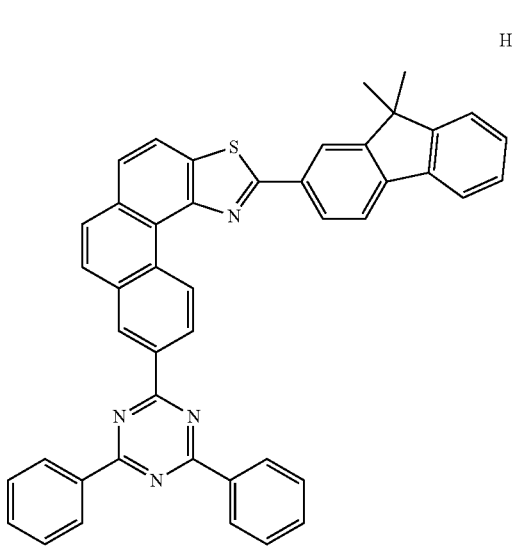
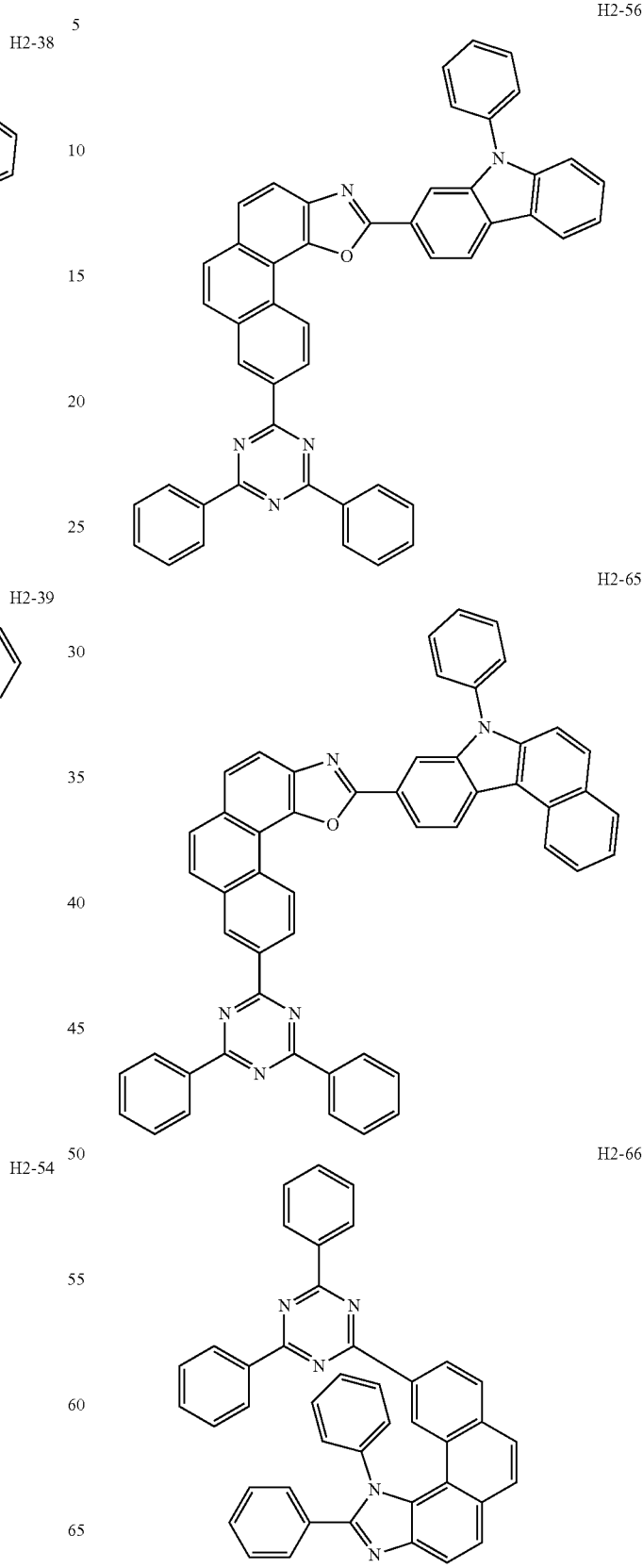

H2-68
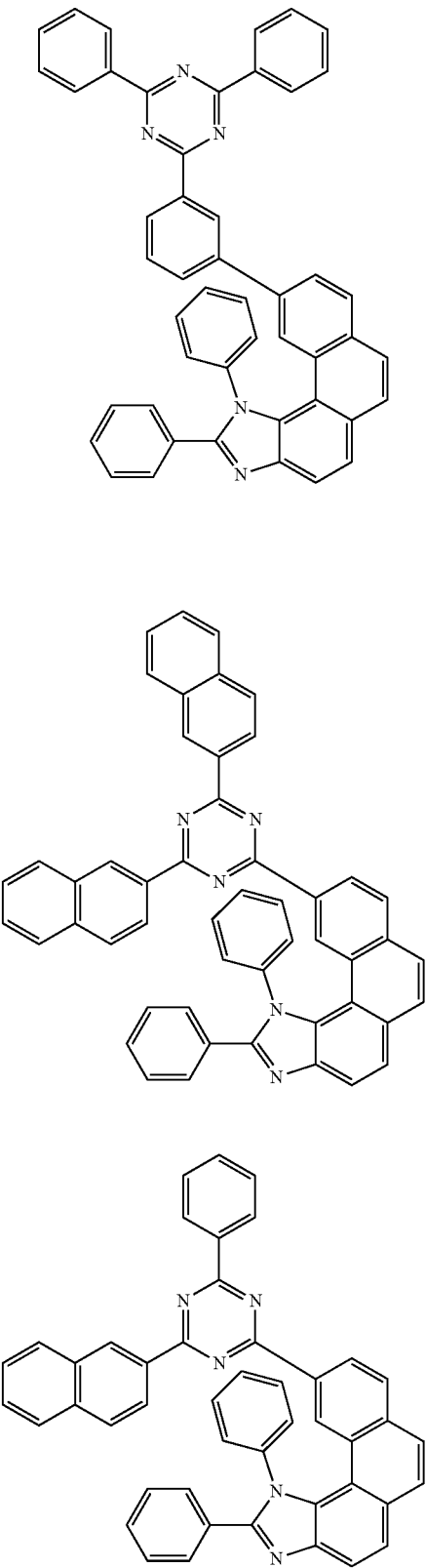
H2-70
H2-71
H2-72
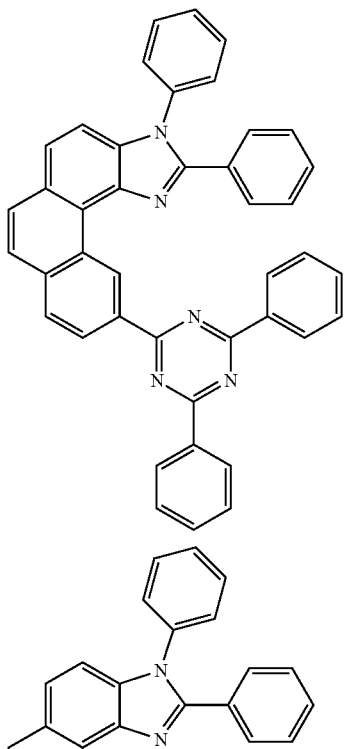
H2-74
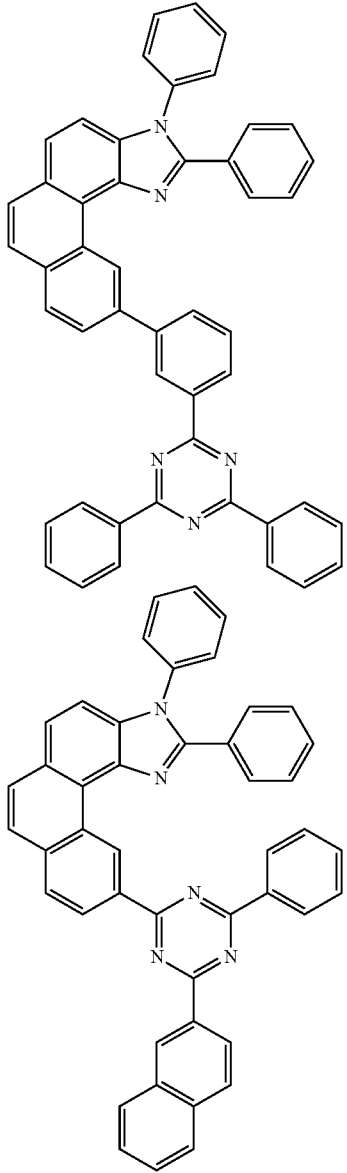
H2-76

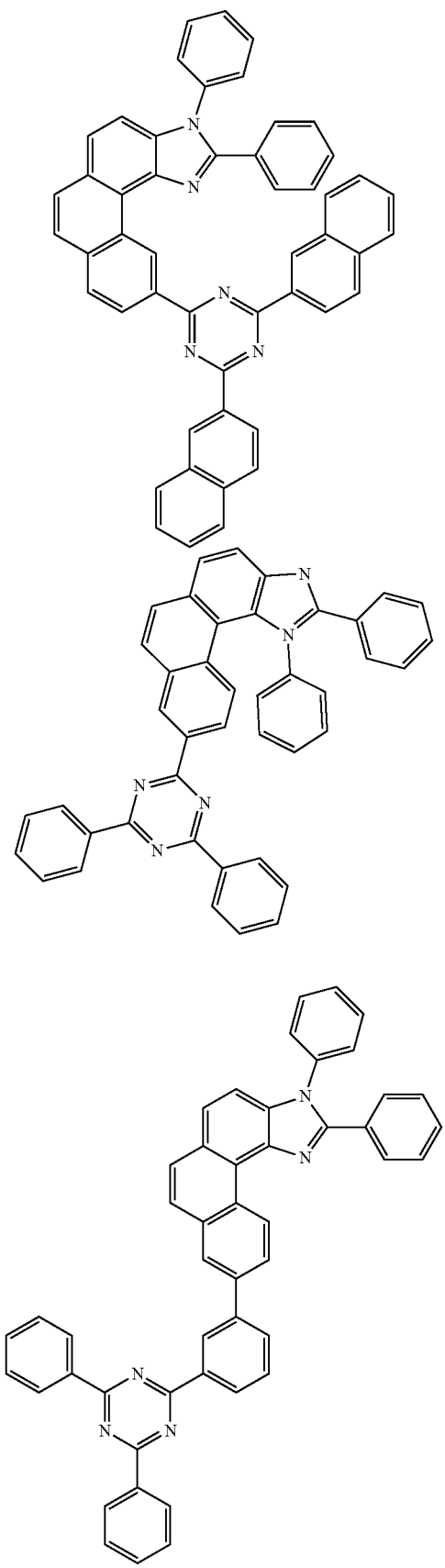
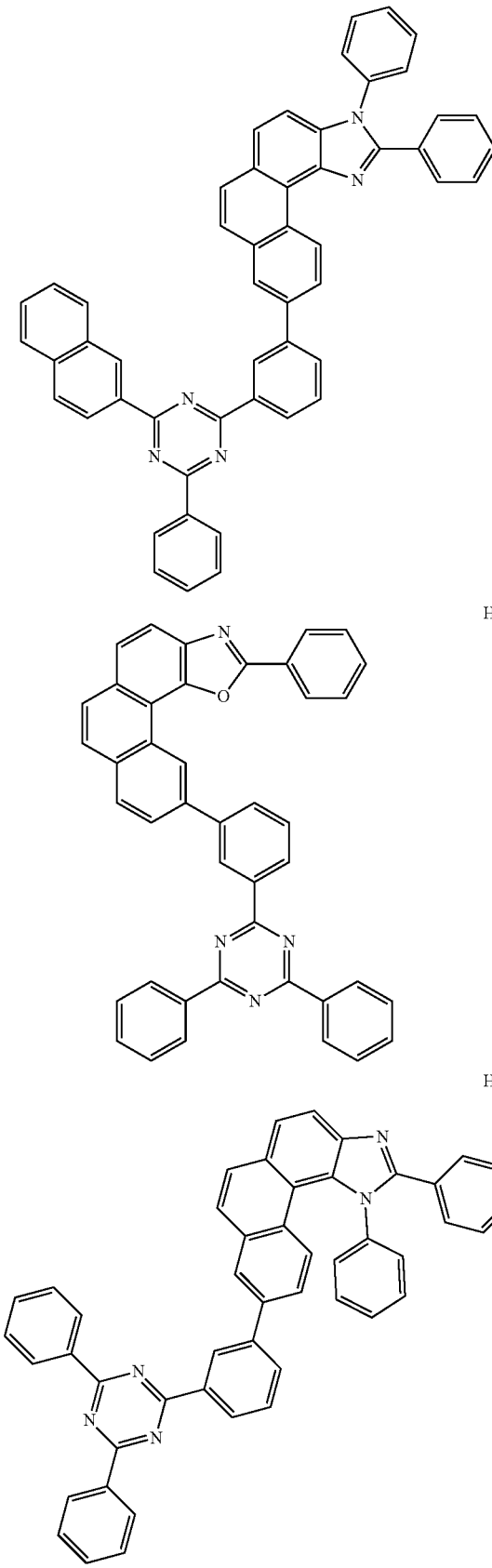

H2-86
H2-87
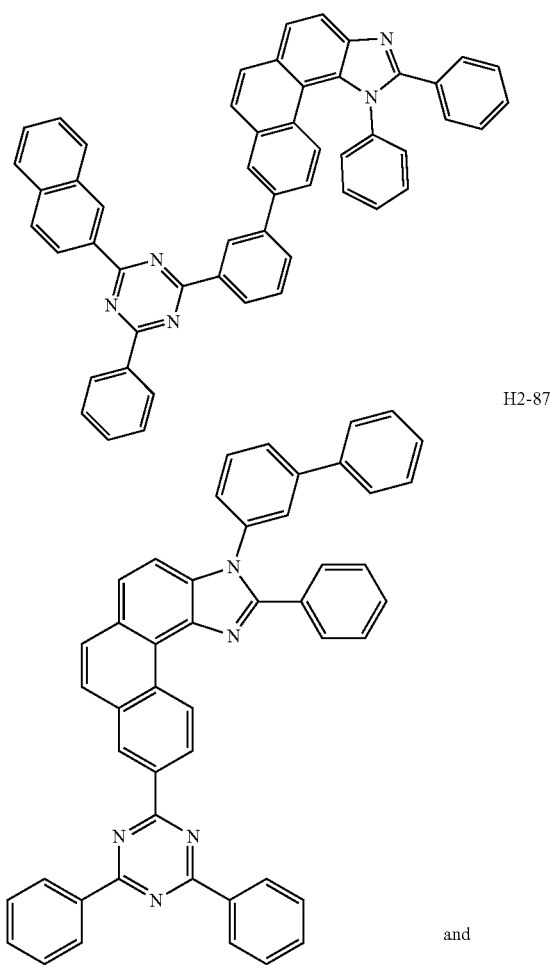
and
H2-88
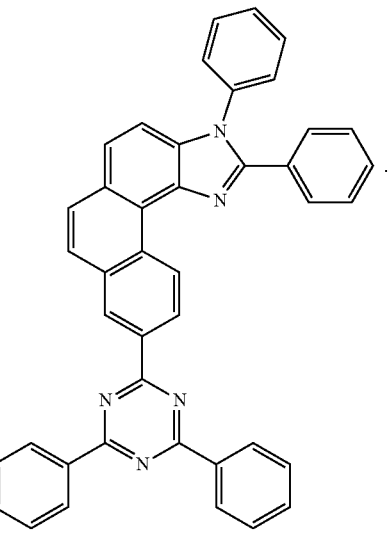
.
7. An organic electroluminescent device comprising: an anode, a cathode, and at least one light-emitting layer between the anode and the cathode, wherein the light-emitting layer comprises a host and a phosphorescent dopant, wherein the host comprises the host materials according to claim 1.
* * * * *

UNITED STATES PATENT AND TRADEMARK OFFICE
CERTIFICATE OF CORRECTION

PATENT NO. : 11,737,353 B2
APPLICATION NO. : 17/670572
DATED : August 22, 2023
INVENTOR(S) : Sang-Hee Cho Page 1 of 1

It is certified that error appears in the above-identified patent and that said Letters Patent is hereby corrected as shown below:

In the Claims

In Claim 3, the numbering of formula 3 at Column 108, Line 27:
"(394)" should be "(3-4)".

Signed and Sealed this
Twenty-fourth Day of October, 2023

Katherine Kelly Vidal
*Director of the United States Patent and Trademark Office*